(12) United States Patent
Kanamaru et al.

(10) Patent No.: US 6,414,003 B1
(45) Date of Patent: *Jul. 2, 2002

(54) **OXAZOLONE DERIVATIVES AND THEIR USE AS ANTI-*HELICOBACTER PYLORI* AGENTS**

(75) Inventors: Tsuneo Kanamaru, Osaka; Masafumi Nakao, Nara; Hiroyuki Tawada; Keiji Kamiyama, both of Osaka, all of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/708,542

(22) Filed: Nov. 9, 2000

Related U.S. Application Data

(62) Division of application No. 09/142,506, filed as application No. PCT/JP97/02157 on Jun. 24, 1997, now Pat. No. 6,169,102.

(30) Foreign Application Priority Data

Jun. 25, 1996 (JP) ............................................. 8-164854
Feb. 7, 1997 (JP) ............................................. 9-025162

(51) Int. Cl.$^7$ ........................................... A61K 31/422
(52) U.S. Cl. ...................................... 514/376; 514/340
(58) Field of Search .................................. 514/376, 340

(56) References Cited

U.S. PATENT DOCUMENTS

| | | |
|---|---|---|
| 2,712,517 A | 7/1955 | Gourevitch et al. ......... 195/114 |
| 2,944,061 A | 7/1960 | Jacob et al. ................. 260/309 |
| 3,173,923 A | 3/1965 | Rao et al. |
| 3,192,198 A | 6/1965 | Nayler et al. ............ 260/239.1 |
| 3,320,282 A | 5/1967 | Schach von Wittenau et al. |
| 4,049,816 A | 9/1977 | Harnden et al. ............. 424/270 |
| 4,584,385 A | 4/1986 | Dirlam ........................ 548/225 |
| 4,769,232 A | 9/1988 | Chappel et al. ............... 424/80 |
| 6,169,102 B1 * | 1/2001 | Kanamaru et al. .......... 514/376 |

FOREIGN PATENT DOCUMENTS

| | | |
|---|---|---|
| GB | 862685 | 3/1961 |
| WO | WO 96/01821 | 1/1996 |

OTHER PUBLICATIONS

VanHoof et al., Infection 1986, 14: 294–298.
McNulty et al., Antimicrob. Agents Chemother., 1985, 28: 837–838.
Ozeki et al., J. Clin. Microbiol, 1997, 35: 2315–2319.
Oie et al. Biol Pharm. Bull., 1997, 20: 584–585.
Traub et al., J. Antimicrob. Chemother., 1995, 35: 149–154.
Goodwin et al., J. Antimicrob. Chemother., 1986, 17: 309–314.
J. Antibiotics, 1983, 36: 1421–1424.
Nakao et al., J. Antimicrob. Chemother., 1986, 17: 433–439.
McNulty et al., Eur. J. Clin. Microbiol. Infect. Dis., 1988, 7: 566–569.
Georgopapadakou et al., Antimicrob. Agents Chemother., 1991, 35: 2645–2648.
Nakao et al. Eur. J. Clin. Microbiol. Infect. Dis., 1995, 14: 391–399.
Washington II, Mayo Clin. Proc., 1969, 44: 811–824.
Glupczynski, Zbl. Bakt., 1993, 280: 227–238.
Glupcynski, Eur. J. Epidemiol., 1988, 4: 154–157.
Jpn. J. Chemother., 1995, 43(S–1): 314–318.
Jpn. J. Chemother., 1995, 43(S–1): 74–90.
Jpn. J. Chemother., 1996, 44(S–1): 393–399.
Jpn. J. Chemother., 1987, 35(S–2): 1–16.
Jpn. J. Chemother., 1987, 35(S–2): 79–97.
Jpn, J. Chemother., 1987, 35(S–2): 104–145.
Witty et al., Bioorganic & Medicinal Chemistry Letters, vol. 6, Issue 12, Jun. 18, 1996, pp. 1375–1380.
Werner et al., CA 95: 78399, 1981.
Krepelka et al., CA 99: 122397, 1983.
Chemical Abstracts, vol. 95, No. 9, Aug. 31, 1981, Abstract No. 78399t.
Agric. Biol. Chem. 42(1), 147–151, 1978.

\* cited by examiner

*Primary Examiner*—Laura L. Stockton
(74) *Attorney, Agent, or Firm*—Fitzpatrick, Cella, Harper & Scinto

(57) ABSTRACT

An anti-*Helicobacter pylori* agent comprising a compound represented by the formula:

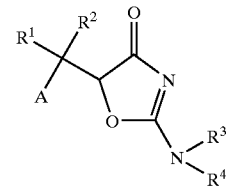

wherein A represents an aromatic ring group which may be substituted; $R^1$ and $R^2$, whether identical or not, each represent a hydrogen atom or a hydrocarbon group which may be substituted; $R^3$ and $R^4$, whether identical or not, each represent a hydrogen atom, a hydrocarbon group which may be substituted, an acyl group, a carbamoyl group which may be substituted, or a carboxyl group which may be esterified; or a salt thereof.

2 Claims, No Drawings

US 6,414,003 B1

OXAZOLONE DERIVATIVES AND THEIR USE AS ANTI-HELICOBACTER PYLORI AGENTS

This application is a division of application Ser. No. 09/142,506 filed Sep. 10, 1998, now U.S. Pat. No. 6,169,102, which is a of 371 PCT/JP97/02157 filed Jun. 24, 1997.

TECHNICAL FIELD

The present invention relates to an anti-*Helicobacter pylori* agent comprising an oxazolin-4-one derivative useful as a therapeutic agent for gastric and duodenal ulcer etc.

BACKGROUND ART

As therapeutic agents for ulcer, there have been developed antacids, anticholinergic agents, antigastrin agents, gastrointestinal hormones, antipepsine agents, histamine $H_2$ receptor antagonists, tissue repairing agents, mucosa-protecting agents, microcirculation-improving agents, proton pump inhibitors etc. The development of histamine $H_2$ receptor antagonists and proton pump inhibitors, both possessing potent acid secretion-suppressing activity, in particular, has facilitated ulcer treatment.

However, these therapeutic agents for ulcer are unsatisfactory in terms of suppressing effect on recurrent ulcer. On the other hand, *Helicobacter pylori*, a gram-negative microaerophilic bacterium belonging to the genus Helicobacter, has been suggested as a potential major cause of recurrence of gastritis, duodenal ulcer, gastric ulcer etc. Although many antibacterial agents readily inhibit the proliferation of the-respective microorganisms belonging to the genus Helicobacter in vitro, their efficacy in humans and animal experiments is very low when administered singly in vivo.

Various diseases caused by *Helicobacter pylori* as such are treated by chemotherapies such as double chemotherapy with a bismuth preparation and an antibiotic, and triple chemotherapy with a bismuth preparation, metronidazole (U.S. Pat. No. 2,944,061) and either tetracycline (e.g., U.S. Pat. No. 2,712,517) or amoxicillin (U.S. Pat. No. 3,192,198). Metronidazole, an imidazole derivative possessing anti-*Helicobacter pylori* activity is used in combination with antibiotics. These bismuth preparations, antibiotics, metronidazole etc. are administered orally. Also, clinical studies have shown that eradication of this microorganism results in healing and decreased recurrence rates in ulcer.

However, these bismuth preparations, antibiotics, metronidazole etc. must be administered at high daily doses to maintain sufficient concentrations to inhibit *Helicobacter pylori* proliferation at the sites of their proliferation, resulting in many problems, including adverse effects such as vomiting and diarrhea.

There have been developed various compounds possessing anti-*Helicobacter pylori* activity. For example, Japanese Patent Unexamined Publication No. 117268/1993 discloses a pyridine derivative possessing anti-*Helicobacter pylori* activity, and European Patent EPO 535528A1 discloses an imidazole derivative possessing anti-*Helicobacter pylori* activity.

DISCLOSURE OF INFORMATION

After extensive investigation in view of the above problems, the present inventors found that a particular oxazolin-4-one derivative exhibits very specific and excellent antibacterial activity against the bacteria of the genus Helicobacter, represented by *Helicobacter pylori*. The inventors conducted further investigation based on this finding, and developed the present invention.

Accordingly, the present invention relates to (1) an anti-*Helicobacter pylori* composition comprising a compound of the formula:

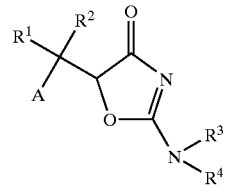

(I)

wherein A represents an aromatic group which may be substituted, $R^1$ and $R^2$ independently represent a hydrogen atom or a hydrocarbon group which may be substituted, $R^3$ and $R^4$ independently represent a hydrogen atom, a hydrocarbon group which may be substituted, an acyl group, a carbamoyl group which may be substituted, or a carboxyl group which may be esterified, or a salt thereof, and a pharmacologically acceptable diluent, excipient or carrier, (2) the anti-*Helicobacter pylori* composition according to the description in (1) above, wherein A is an aromatic heterocyclic group which may be substituted, (3) the anti-*Helicobacter pylori* composition according to the description in (1) above, wherein A is a group represented by the formula:

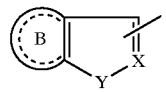

(II)

wherein ring B is a 6-membered aromatic ring which may be substituted, x represents CH or N, Y represents O, S or —N—$R^5$ ($R^5$ represents a hydrogen atom or a hydrocarbon group which may be substituted), (4) the anti-*Helicobacter pylori* composition according to the description in (1) above, wherein A is a group represented by the formula:

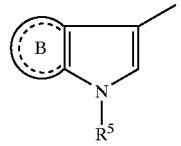

(II-1)

wherein ring B is a 6-membered aromatic ring which may be substituted, $R^5$ represents a hydrogen atom or a hydrocarbon group which may be substituted, (5) the anti-*Helicobacter pylori* composition according to the description in (1) above, wherein A represented indolyl which may be substituted by 1 to 3 substituents selected from the group consisting of hydroxyl, halogen, nitro, cyano, lower alkyl which may be substituted by 1 to 5 halogens and lower alkoxy which may be substituted by 1 to 5 halogens, $R^1$ and $R^2$ independently represent hydrogen or lower alkyl which may be substituted by 1 to 5 halogens, $R^3$ and $R^4$ independently represent hydrogen or lower alkyl, (6) the anti-*Helicobacter pylori* composition according to the description in (5) above, wherein A is indolyl, $R^1$ and $R^3$ are hydrogen, and $R^2$ and $R^4$ are $C_{1-7}$ alkyl, (7) the anti-*Helicobacter pylori* composition according to the description in (6) above, wherein A is 3-indolyl, $R^2$ and $R^4$ are methyl, (8) the anti-*Helicobacter pylori* composition according to the description in (1) above, wherein the compound is indolmycin, (9) the anti-*Helicobacter pylori* composition according to the description in (1) above, as an agent for prevention or treatment of a disease associated with *Helicobacter pylori* infection,

(10) the anti-*Helicobacter pylori* composition according to the description in (9) above, wherein the disease associated with *Helicobacter pylori* infection is gastric or duodenal ulcer, gastritis or gastric cancer,

(11) the anti-*Helicobacter pylori* composition according to the description in (1) above, which is used in combination with an antibacterial agent,

(12) the anti-*Helicobacter pylori* composition according to the description in (1) above, which is used in combination with antiulcer agent,

(13) the anti-*Helicobacter pylori* composition according to the description in (1) above, which is used in combination with antibacterial agent and antiulcer agent,

(14) use of compound of the formula:

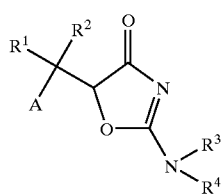

(I)

wherein A represents an aromatic group which may be substituted, $R^1$ and $R^2$ independently represent a hydrogen atom or a hydrocarbon group which may be substituted, $R^3$ and $R^4$ independently represent a hydrogen atom, a hydrocarbon group which may be substituted, an acyl group a carbamoyl group which may be substituted, or a carboxyl group which may be esterified, or a salt thereof for the preparation of an anti-*Helicobacter pylori* agent,

(15) a method for prevention or treatment of a disease associated with *Helicobacter pylori* infection in a mammal which comprises administering to a subject in need an effective amount of a compound of the formula (I):

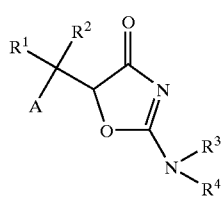

(I)

wherein A represents an aromatic group which may be substituted, $R^1$ and $R^2$ independently represent a hydrogen atom or a hydrocarbon group which may be substituted, $R^3$ and $R^4$ independently represent a hydrogen atom, a hydrocarbon group which may be substituted, an acyl group, a carbamoyl group which may be substituted, or a carboxyl group which may be esterified, or a salt thereof,

(16) a method for producing an anti-*Helicobacter pylori* composition comprising mixing a compound of the formula (I):

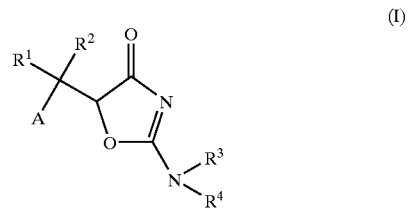

(I)

wherein A represents an aromatic group which may be substituted, $R^1$ and $R^2$ independently represent a hydrogen atom or a hydrocarbon group which may be substituted, $R^3$ and $R^4$ independently represent a hydrogen atom, a hydrocarbon group which may be substituted, an acyl group, a carbamoyl group which may be substituted, or a carboxyl group which may be esterified, or a salt thereof with a pharmacologically acceptable diluent, excipient or/and carrier,

(17) a compound of the formula:

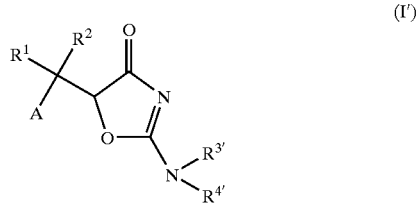

(I')

wherein A represents an aromatic group which may be substituted, $R^1$ and $R^2$ independently represent a hydrogen atom or a hydrocarbon group which may be substituted, $R^{3'}$ and $R^{4'}$ independently represent a hydrogen atom or a hydrocarbon group which may be substituted, or a salt thereof, provided that (1) when A is 3-indolyl, $R^1$ and $R^{3'}$ are hydrogen and $R^2$ is methyl, $R^{4'}$ is neither $C_{3-6}$ cycloalkyl nor mono-substituted $C_{1-4}$ alkyl wherein said substituent is selected from halogen, hydroxyl, lower alkoxy, lower thioalkyl, aryl, or an unsaturated 2–4 carbon atoms side-chain and (2) when A is 3-indolyl, $R^1$ and $R^{3'}$ are hydrogen and $R^2$ is $C_{1-3}$ alkyl, $R^{4'}$ is not selected from hydrogen, phenyl, anisyl, toluidyl and $C_{1-4}$ alkyl,

(18) a compound of the formula:

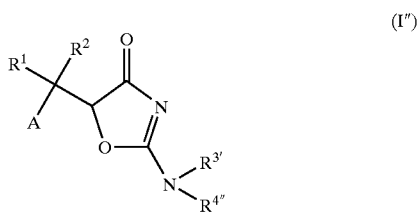

(I'')

wherein A represents an aromatic group which may be substituted, $R^1$ and $R^2$ independently represent a hydrogen atom or a hydrocarbon group which may be substituted, $R^{3'}$ is a hydrogen atom or a hydrocarbon group which may be substituted, $R^{4'''}$ is an acyl group or a carbamoyl group which may be substituted or a salt thereof, provided that when A is 3-indolyl, $R^1$ is hydrogen and $R^2$ and $R^{3'}$ are methyl, $R^{4'''}$ is neither a $C_{2-5}$ alkanoyl or an mono-substituted $C_{2-5}$ alkanoyl wherein said substituent is selected from amino, halogen, phenyl, p-hydroxyphenyl, or lower alkoxy, nor a carbamoyl group substituted by $C_{1-4}$ alkyl, $C_{3-6}$ cycloalkyl or phenyl,

(19) a compound of the formula:

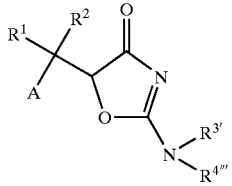

(I''')

wherein A represents an aromatic group which may be substituted, $R^1$ and $R^2$ independently represent a hydrogen atom or a hydrocarbon group which may be substituted, $R^{3'}$ is a hydrogen atom or a hydrocarbon group which may be substituted, $R^{4'''}$ is a carboxyl group which may be esterified, or a salt thereof,

(20) the compound according to the description in (19) above, wherein A is indolyl, $R^1$ and $R^2$ independently represent a hydrogen atom or methyl, $R^{3'}$ is methyl and $R^{4'''}$ is a carboxyl group which is esterified,

(21) a method of producing indolmycin by culturing the Streptomyces sp. HC-21 strain in a medium to produce and accumulate indolmycin in the culture broth, and harvesting the indolmycin, and

(22) the Streptomyces sp. HC-21 strain which assimilates L-rhamnose and whose spores have a spiny surface.

The "aromatic ring group which may be substituted" represented by A in formula (I) is exemplified by monocyclic or condensed polycyclic aromatic hydrocarbon groups or aromatic heterocyclic groups. Such aromatic hydrocarbon groups include, for example, phenyl, naphthyl, anthryl, phenanthryl and acenaphthylenyl, with preference given to phenyl, 1-naphthyl, 2-naphthyl etc.

The aromatic heterocyclic groups include, for example, aromatic monocyclic heterocyclic groups such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl and triazinyl; and aromatic condensed heterocyclic groups such as benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl and 1,2,4-triazolo[4,3-b]pyridazinyl. Among aromatic condensed heterocyclic group, indolyl is preferable and 3-indolyl is more preferable.

Substituents for the "aromatic ring group or aromatic heterocyclic group which may be substituted" represented by A in formula (I) include, for example, hydroxyl group, halogens (e.g., fluorine, chlorine, bromine, iodine), nitro, cyano, lower alkyls that may be substituted by 1 to 5 halogens (e.g., fluorine, chlorine, bromine, iodine), lower alkoxys that may be substituted by 1 to 5 halogens (e.g., fluorine, chlorine, bromine, iodine) benzyloxy and $C_{1-4}$ alkoxy carbonyl (e.g. methoxy carbonyl, ethoxy carbony, propoxy carbonyl, butoxy carbonyl). Such lower alkyls include, for example, alkyl groups having 1 to 4 carbon atoms, such as methyl, ethyl, n-propyl, isopropyl, n-butyl, isobutyl, sec-butyl and tert-butyl, with preference given to methyl and ethyl. Such lower alkoxys include alkoxy groups having 1 to 4 carbon atoms, such as methoxy, ethoxy, n-propoxy, isopropoxy, n-butoxy, isobutoxy, sec-butoxy and tert-butoxy, with preference given to methoxy and ethoxy. It is preferable that 1 to 3 (preferably 1 to 2) of these substituents, whether identical or not, be present. Substituents for the "aromatic ring group or aromatic heterocyclic group which may be substituted" represented by A also include alkylene dioxo such as methylene dioxo and ethylene dioxo.

The "hydrocarbon group which may be substituted" represented by $R^1$ or $R^2$ in formula (I) include aliphatic chain hydrocarbon groups, alicyclic hydrocarbon groups and aryl groups, with preference given to aliphatic chain hydrocarbon groups.

Such aliphatic chain hydrocarbon groups include linear or branched aliphatic hydrocarbon groups such as alkyl groups, alkenyl groups and alkynyl groups. Particularly preferred are lower alkyl groups, lower alkenyl groups, lower alkynyl groups etc. Such lower alkyls include, for example, $C_{1-7}$ alkyls such as methyl, ethyl, n-propyl, isopropyl, n-butyl, isobutyl, sec-butyl, tert-butyl, n-pentyl, isopentyl, neopentyl, 1-methylpropyl, n-hexyl, isohexyl, 1,1-dimethylbutyl, 2,2-dimethylbutyl, 3,3-dimethylbutyl, 3,3-dimethylpropyl, 2-ethylbutyl and n-heptyl. Preferred are $C_{1-3}$ alkyls such as methyl, ethyl and propyl, with greater preference given to $C_{1-2}$ alkyls such as methyl and ethyl. Such lower alkenyl groups include, for example, $C_{2-6}$ alkenyl groups such as vinyl, allyl, isopropenyl, 2-methylallyl, 1-propenyl, 2-methyl-1-propenyl, 2-methyl-2-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyll with preference given to $C_{2-5}$ alkenyls such as vinyl, allyl, isopropenyl, 2-methylallyl, 2-methyl-1-propenyl, 2-methyl-2-propenyl and 3-methyl-2-butenyl. Such lower alkynyl groups include, for example, $C_{2-6}$ alkynyls such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl, with preference given to $C_{2-4}$ alkynyls such as ethynyl, 1-propynyl and 2-propynyl.

Such alicyclic hydrocarbon groups include saturated or unsaturated alicyclic hydrocarbon groups such as cycloalkyl groups, cycloalkenyl groups and cycloalkadienyl groups. Such cycloalkyl groups are preferably cycloalkyl groups having 3 to 9 carbon atoms, such as cyclopropyl, cyclobutyl, cyclopentyl, cyclohexyl, cycloheptyl, cyclooctyl and cyclononyl, with greater preference given to $C_{3-6}$ cycloalkyl groups such as cyclopropyl, cyclobutyl, cyclopentyl and cyclohexyl. Such cycloalkenyl groups include, for example, $C_{3-6}$ cycloalkenyls such as 2-cyclopenten-1-yl, 3-cyclopenten-1-yl, 2-cyclohexen-1-yl, 3-cyclohexen-1-yl, 1-cyclobuten-1-yl and 1-cyclopenten-1-yl. Such cycloalkadienyl groups include, for example, $C_{4-6}$ cycloalkadienyls such as 2,4-cyclopentadien-1-yl, 2,4-cyclohexadien-1-yl and 2,5-cyclohexadien-1-yl.

The aryl groups in the hydrocarbon groups include monocyclic or condensed polycyclic aromatic hydrocarbon groups such as phenyl, naphthyl, anthryl, phenanthryl and acenaphthylenyl, with preference given to phenyl, 1-naphthyl, 2-naphthyl etc.

Substituents for the "hydrocarbon group which may be substituted" represented by $R^1$ or $R^2$ in formula (I) include aryl groups which may be substituted, cycloalkyl or cycloalkenyl groups which may be substituted, heterocyclic groups that may be substituted, amino group that may be substituted, hydroxyl group which may be substituted, thiol group which may be substituted, and halogens (e.g., fluorine, chlorine, bromine, iodine). One to five (preferably 1 to 3) of these optionally chosen substituents may be present. Such aryl groups which may be substituted include phenyl, naphthyl, anthryl, phenanthryl and acenaphthylenyl, with preference given to phenyl, 1-naphthyl and 2-naphthyl. Substituents for such aryl groups which may be substituted include alkoxy groups having 1 to 3 carbon atoms (e.g., methoxy, ethoxy, propoxy), halogen atoms (e.g., fluorine, chlorine, bromine, iodine) and alkyl groups having 1 to 3 carbon atoms (e.g., methyl, ethyl, propyl); 1 to 2 of these optionally chosen substituents may be present. Such cycloalkyl groups which may be substituted include $C_{3-7}$ cycloalkyl groups such as cyclopropyl, cyclobutyl, cyclopentyl, cyclohexyl and cycloheptyl. The kinds and number of substituents for such cycloalkyl groups which may be substituted are the same as those for the substituents the above-described aryl group that may be substituted. Such cycloalkenyl groups which may be substituted include $C_{3-6}$ cycloalkenyl groups such as cyclopropanyl, cyclobutenyl, cyclopentenyl and cyclohexenyl. The kinds and number of substituents for such cycloalkenyl groups which may be substituted are the same as those for the substituents for the above-described aryl group that may be substituted. Such heterocyclic groups which may be substituted for include aromatic heterocyclic groups having at least 1 hetero atom selected from oxygen, sulfur or nitrogen as a ring-constituting atom (ring atom), and saturated or unsaturated non-aromatic heterocyclic groups (aliphatic heterocyclic groups), with preference given to aromatic heterocyclic groups. Such aromatic heterocyclic groups include aromatic monocyclic heterocyclic groups (e.g., furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl) and aromatic condensed heterocyclic groups (e.g., benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl), with preference given to furyl, thienyl, indolyl, isoindolyl, pyrazinyl, pyridyl, pyrimidinyl etc. Such non-aromatic heterocyclic groups include, for example, oxylanyl, azetidinyl, oxetanyl, thietanyl, pyrrolidinyl, tetrahydrofuryl, thiolanyl, piperidyl, tetrahydropyranyl, morpholinyl, thiomorpholinyl and piperazinyl. Substituents for such heterocyclic groups which may be substituted for include alkyl groups having 1 to 3 carbon atoms (e.g., methyl, ethyl, propyl). Substituents for such amino group which may be substituted for, hydroxyl group that may be substituted for, and thiol group that may be substituted for, include, for example, lower ($C_{1-3}$) alkyl groups (e.g., methyl, ethyl, propyl). When the "hydrocarbon group which may be a substituted" represented by $R^1$ or $R^2$ is an alicyclic hydrocarbon group or an aryl group, the substituent may also be an alkyl group having 1 to 3 carbon atoms (e.g., methyl, ethyl, propyl).

With respect to the formula (I), the preferable combination of $R^1$ and $R^2$ is that $R^1$ is hydrogen and $R^2$ is $C_{1-3}$ alkyl which may be substituted by 1 to 5 halogens.

The hydrocarbon group and the substituent in the "hydrocarbon group which may be substituted" represented by $R^3$ or $R^4$ in formula (I) and represented by $R^{3'}$ or $R^{4'}$ in formula (I') are exemplified by the same hydrocarbon groups and substituents mentioned to exemplify the hydrocarbon group and substituent for $R^1$ and $R^2$ above, respectively.

With respect to the formula (I), the preferable combination of $R^3$ and $R^4$ is that $R^3$ is hydrogen and $R^4$ is $C_{1-3}$ alkyl.

The acyl group represented by $R^3$ or $R^4$ in formula (I) is exemplified by aliphatic acyl groups such as alkanoyl groups, alkenoyl groups, cycloalkanecarbonyl groups and alkanesulfonyl groups; aromatic acyl groups such as aroyl groups, arylalkanoyl groups, arylalkenoyl groups and arenesulfonyl groups; heterocyclic aromatic acyl groups such as aromatic heterocyclic carbonyl groups and aromatic heterocyclic alkanoyl groups; and non-aromatic heterocyclic arbonyl groups (aliphatic heterocyclic carbonyl groups).

"Alkanoyl groups" mean alkylcarbonyl groups, preferable examples thereof including lower alkanoyl groups having 1 to 8 carbon atoms, such as formyl, acetyl, propionyl, butyryl, isobutyryl, valeryl, isovaleryl, pivaloyl and hexanoyl.

"Alkenoyl groups" mean alkenylcarbonyl groups, preferable examples thereof including $C_{3-6}$ alkenoyl groups such as acryloyl, methacryloyl, crotonoyl and isocrotonoyl.

"Cycloalkanecarbonyl groups" mean cycloalkylcarbonyl groups, preferable examples thereof including those having 4 to 7 carbon atoms, such as cyclopropanecarbonyl groups, cyclobutanecarbonyl groups, cyclopentanecarbonyl groups and cyclohexanecarbonyl groups.

"Alkanesulfonyl groups" mean alkylsulfonyl groups, preferable examples thereof including those having 1 to 4 carbon atoms, Such as mesyl, ethanesulfonyl and propanesulfonyl.

"Aroyl groups" mean arylcarbonyl groups, preferable examples thereof including those having 7 to 11 carbon atoms, such as benzoyl, p-toluoyl, 1-naphthoyl and 2-naphthoyl.

"Arylalkanoyl groups" mean alkylcarbonyl groups substituted for by an aryl group, preferable examples thereof including $C_{6-8}$ aryl-$C_{2-5}$ alkanoyl groups such as phenylacetyl, phenylpropionyl, hydroatropoyl and phenylbutyryl.

"Arylalkenoyl groups" mean alkenylcarbonyl groups substituted for by an aryl group, preferable examples thereof including $C_{6-8}$ aryl-$C_{3-5}$ alkenoyl groups such as cinnamoyl and atropoyl.

"Arenesulfonyl groups" mean arylsulfonyl groups, preferable examples thereof including those having 6 to 8 carbon atoms, such as benzenesulfonyl and p-toluenesulfonyl.

Preferable examples of "aromatic heterocyclic carbonyl groups" include furoyl, thenoyl, nicotinoyl, isonicotinoyl, pyrrolecarbonyl, oxazolecarbonyl, thiazolecarbonyl, imidazolecarbonyl and pyrazolecarbonyl.

"Aromatic heterocyclic alkanoyl groups" mean alkylcarbonyl groups substituted by an aromatic heterocyclic group, preferable examples thereof including aromatic heterocyclic ring-$C_{2-5}$ alkanoyl groups such as thienylacetyl, thienylpropanoyl, furylacetyl, thiazolylacetyl, 1,2,4-thiadiazolylacetyl and pyridylacetyl.

Preferable examples of "non-aromatic heterocyclic carbonyl groups" include aliphatic heterocyclic carbonyls such as azetidinylcarbonyl, pyrrolidinylcarbonyl and piperidinylcarbonyl.

The carbamoyl group which may be substituted represented by $R^3$ or $R^4$ in formula (I) and represented by $R_4'$ in formula (I'), is exemplified by "N-monosubstitutional carbamoyl groups" and "N,N-disubstitutional carbamoyl groups," as well as non-substitutional carbamoyl. An "N-monosubstitutional carbamoyl group" means a carbamoyl group having one substituent on nitrogen. Examples of said substituent include $C_{1-6}$ alkyls (e.g., methyl, ethyl, propyl, isopropyl, butyl, t-butyl, pentyl, hexyl), $C_{3-6}$ cycloalkyl groups (e.g., cyclopropyl, cyclobutyl, cyclopentyl, cyclohexyl), aryl groups (e.g., phenyl, 1-naphthyl, 2-naphthyl), aralkyl groups (e.g., benzyl, phenethyl) and heterocyclic groups (e.g., the "heterocyclic groups" mentioned to exemplify the "substituent" for the "hydrocarbon residue which may be substituted" represented by $R^1$ or $R^2$ above). Such aryl groups, aralkyl groups and heterocyclic groups may be substituted. Said substituent is exemplified by hydroxyl group, amino group which may substituted by 1 or 2 lower alkyls (e.g., those having 1 to 4 carbon atoms, such as methyl, ethyl, propyl, isopropyl and butyl) or acyl groups (e.g., formyl, acetyl, propionyl, benzoyl), halogens (e.g., fluorine, chlorine, bromine, iodine), nitro, cyano, lower alkyls which may be substituted by 1 to 5 halogens (e.g., fluorine, chlorine, bromine, iodine) and lower alkoxys which may be substituted by 1 to 5 halogens (e.g., fluorine, chlorine, bromine, iodine). Such lower alkyls include, for example, alkyl groups having 1 to 4 carbon atoms, such as methyl, ethyl, n-propyl, isopropyl, n-butyl, isobutyl, sec-butyl and tert-butyl, with preference given to methyl and ethyl. Such lower alkoxys include alkoxy groups having 1 to 4 carbon atoms, such as methoxy, ethoxy, n-propoxy, isopropoxy, n-butoxy, isobutoxy, sec-butoxy and tert-butoxy, with preference given to methoxy and ethoxy. It is preferable that 1 to 3 (preferably 1 to 2) of these substituents, whether identical or not, be present.

An "N,N-disubstitutional carbamoyl group" means a carbamoyl group having two substituents on a nitrogen atom. Examples of one of said substituents include the same substituents as those mentioned to exemplify the substituent for the "N-monosubstitutional carbamoyl group" above; examples of the other substituent include $C_{1-6}$ alkyl groups (e.g., methyl, ethyl, propyl, isopropyl, butyl, t-butyl, pentyl, hexyl), $C_{3-6}$ cycloalkyl groups (e.g., cyclopropyl, cyclobutyl, cyclopentyl, cyclohexyl) and $C_{6-10}$ aralkyl groups (e.g., benzyl, phenethyl). The two substituents may form a cyclic amino group in cooperation with the nitrogen atom. In this case, examples of cyclic aminocarbamoyl groups include 1-azetidinylcarbonyl, 1-pyrrolidinylcarbonyl, piperidinocarbonyl, morpholinocarbonyl, 1-piperazinylcarbonyl, and 1-piperazinylcarbonyl having a lower alkyl group such as $C_{1-6}$ alkyl (e.g., methyl, ethyl, propyl, isopropyl, butyl, t-butyl, pentyl, hexyl), an aralkyl group such as benzyl and phenethyll an aryl group such as phenyl, 1-naphthyl and 2-naphthyl, or the like, at the 4-position.

The "carboxyl group which may be esterified" represented by $R^3$ or $R^4$ in formula (I) and represented by $R^{4'''}$ in formula (I'''), is exemplified by "lower alkoxycarbonyl groups," "aryloxycarbonyl groups" and "aralkyloxycarbonyl groups," as well as free carboxyl group.

Preferable examples of "lower alkoxycarbonyl groups" include those having 2 to 8 carbon atoms, such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl and tert-pentyloxycarbonyl, with preference given to those having 2 to 4 carbon atoms, such as methoxycarbonyl, ethoxycarbonyl and propoxycarbonyl.

Preferable examples of "aryloxycarbonyl groups" include those having 7 to 12 carbon atoms, such as phenoxycarbonyl, 1-naphthoxycarbonyl and 2-naphthoxycarbonyl. Preferable examples of "aralkyloxycarbonyl groups" include those having 8 to 10 carbon atoms, such as benzyloxycarbonyl and phenethyloxycarbonyl. These aryloxycarbonyl groups and aralkyloxycarbonyl groups may be substituted; useful substituents are identical to those mentioned to exemplify the substituent for aryl groups and aralkyl groups in the case of N-monosubstitutional carbamoyl groups.

The "6-membered aromatic ring which may be substituted" represented by ring B in formula (II) is exemplified by benzene ring which may be substituted, and 6-membered aromatic heterocyclic ring that may be substituted. When ring B represents a benzene ring which may be substituted, formula (II) represents a group represented by the formula:

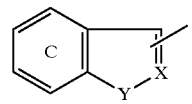

(II-a)

wherein ring C may be substituted; X and Y have the same definitions as those shown above. When ring B represents a 6-membered aromatic heterocyclic ring which may be substituted, the groups represented by formula (II) include, for example, those represented by the following formulas:

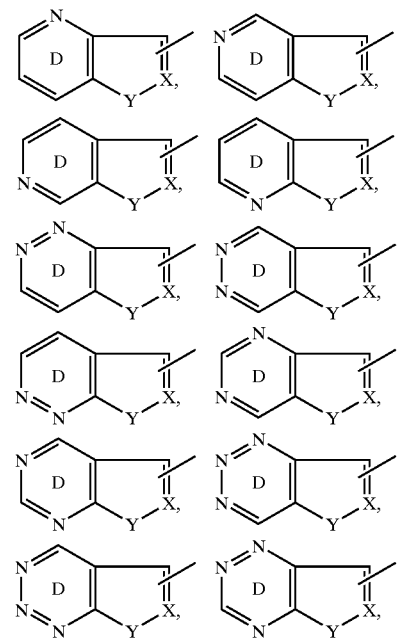

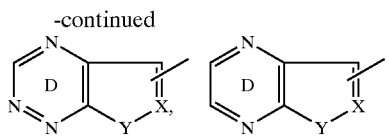

In these formulas, ring D may be substituted; X and Y have the same definitions as those shown above.

With respect to the above formulas, the substituents for rings C and D are identical to those mentioned to exemplify the "substituent" for the "aromatic ring group which may be substituted", represented by A. These substituents may bound to any carbon atom of rings C and D.

The "hydrocarbon group which may be substituted" represented by $R^5$ in formula (II-1) is exemplified by the same hydrocarbon groups as those mentioned to exemplify the hydrocarbon group represented by $R^1$ or $R^2$, which may be substituted.

With respect to the formula (I), the preferable combination of A, $R^1$, $R^2$, $R^3$ and $R^4$ is that A is indolyl, $R^1$ and $R^3$ are hydrogen, and $R^2$ and $R^4$ are $C_{1-3}$ alkyl. The specific examples of the above-described oxazolin-4-one derivative include indolmycin.

Salts of the compound represented by formula (I), (I'), (I'') or (I''') include pharmacologically acceptable acid addition salts; acids that form an acid addition salt include acetic acid, lactic acid, succinic acid, maleic acid, tartaric acid, citric acid, gluconic acid, ascorbic acid, benzoic acid, methanesulfonic acid, p-toluenesulfonic acid, cinnamic acid, fumaric acid, phosphonic acid, hydrochloric acid, hydrogen bromide, hydrogen iodide, sulfamic acid and sulfonic acid.

Examples of the compound represented by the formula (I) are given below.

-continued

[Structure: oxazoline core with substituents A-CR¹R²- at 5-position, C=O at 4-position, and NR³R⁴ at 2-position]

| Compound Number | A | R¹ | R² | R³ | R⁴ |
|---|---|---|---|---|---|
| 8) | 3-indolyl (NH) | H | CH₃ | H | H |
| 9) | 3-indolyl (NH) | H | CH₃ | H | CH₃ |
| 10) | 3-indolyl (NH) | H | CH₃ | H | CH₂CH₃ |
| 11) | 3-indolyl (NH) | H | CH₃ | H | (CH₂)₂CH₃ |
| 12) | 3-indolyl (NH) | H | CH₃ | H | CH(CH₃)₂ |
| 13) | 3-indolyl (NH) | H | CH₃ | H | cyclopropyl |
| 14) | 3-indolyl (NH) | H | CH₃ | H | (CH₂)₃CH₃ |
| 15) | 3-indolyl (NH) | H | CH₃ | H | CH₂CH(CH₃)₂ |
| 16) | 3-indolyl (NH) | H | CH₃ | H | phenyl |
| 17) | 3-indolyl (NH) | H | CH₃ | H | CH₂-phenyl |

-continued
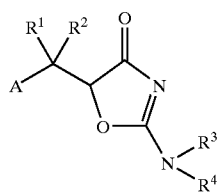
| Compound Number | A | R¹ | R² | R³ | R⁴ |
|---|---|---|---|---|---|
| 18) | indol-3-yl | H | CH₃ | H | (CH₂)₂–C₆H₅ |
| 19) | indol-3-yl | H | CH₃ | CH₃ | CH₃ |
| 20) | indol-3-yl | H | CH₃ | CH₂CH₃ | CH₂CH₃ |
| 21) | indol-3-yl | H | CH₃ | H | CH₂CH₂OH |
| 22) | indol-3-yl | H | CH₃ | H | CH₂CH₂OCH₃ |
| 23) | indol-3-yl | H | CH₃ | H | CH₂CH₂CN |
| 24) | indol-3-yl | CH₃ | CH₃ | H | CH₃ |
| 25) | indol-3-yl | CH₃ | CH₃ | CH₃ | CH₃ |
| 26) | indol-3-yl | H | CH₂CH₃ | H | CH₃ |
| 27) | indol-3-yl | H | CH₂CH₃ | H | CH₃ |

-continued
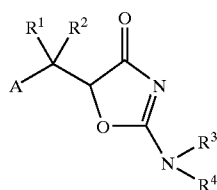
| Compound Number | A | R¹ | R² | R³ | R⁴ |
|---|---|---|---|---|---|
| 28) | indol-3-yl | H | (CH$_2$)$_2$CH$_3$ | H | CH$_3$ |
| 29) | indol-3-yl | H | (CH$_2$)$_2$CH$_3$ | CH$_3$ | CH$_3$ |
| 30) | indol-3-yl | H | CH(CH$_3$)$_2$ | H | CH$_3$ |
| 31) | indol-3-yl | H | CH(CH$_3$)$_2$ | CH$_3$ | CH$_3$ |
| 32) | indol-3-yl | H | CH$_3$ | CH$_3$ | COCH$_3$ |
| 33) | indol-3-yl | H | CH$_3$ | CH$_3$ | COCH$_2$CH$_3$ |
| 34) | indol-3-yl | H | CH$_3$ | CH$_3$ | CO(CH$_2$)$_2$CH$_3$ |
| 35) | indol-3-yl | H | CH$_3$ | CH$_3$ | COCH(CH$_3$)$_2$ |
| 36) | indol-3-yl | H | CH$_3$ | CH$_3$ | CO(CH$_2$)$_3$CH$_3$ |
| 37) | indol-3-yl | H | CH$_3$ | CH$_3$ | CO(CH$_2$)$_4$CH$_3$ |

-continued
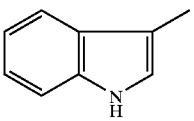
| Compound Number | A | R¹ | R² | R³ | R⁴ |
|---|---|---|---|---|---|
| 38) | 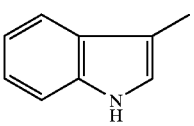 | H | CH₃ | CH₃ | CO(CH₂)₅CH₃ |
| 39) | 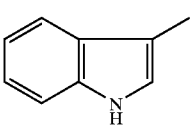 | H | CH₃ | CH₃ | 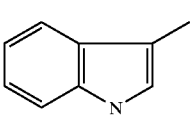 |
| 40) | 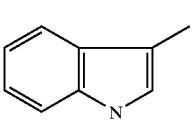 | H | CH₃ | CH₃ | 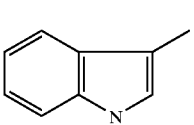 |
| 41) | 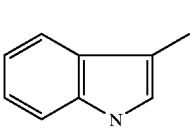 | H | CH₃ | CH₃ | 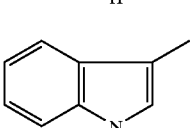 |
| 42) | 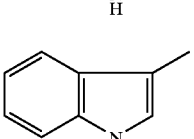 | H | CH₃ | CH₃ | 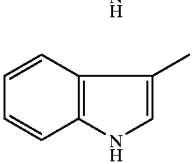 |
| 43) | | H | CH₃ | CH₃ | |
| 44) | | H | CH₃ | CH₃ | |
| 45) | | H | CH₃ | CH₃ | |
| 46) | | H | CH₃ | CH₃ | |
| 47) | | H | CH₃ | CH₃ | |

-continued
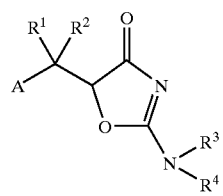
| Compound Number | A | R¹ | R² | R³ | R⁴ |
|---|---|---|---|---|---|
| 48) | 3-indolyl | H | H | H | COCH$_3$ |
| 49) | 3-indolyl | H | H | H | CO—C$_6$H$_5$ |
| 50) | 3-indolyl | H | H | H | CONHCH$_3$ |
| 51) | 3-indolyl | H | H | H | CONHCH$_2$CH$_3$ |
| 52) | 3-indolyl | H | H | H | CONH(CH$_2$)$_2$CH$_3$ |
| 53) | 3-indolyl | H | H | H | CONHCH(CH$_3$)$_2$ |
| 54) | 3-indolyl | H | H | H | CONH(CH$_2$)$_3$CH$_3$ |
| 55) | 3-indolyl | H | H | H | CONH(CH$_2$)$_5$CH$_3$ |
| 56) | 3-indolyl | H | H | H | CONH-cyclohexyl |
| 57) | 3-indolyl | H | H | H | CONHCH$_2$-C$_6$H$_5$ |

-continued
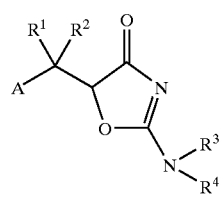
| Compound Number | A | $R^1$ | $R^2$ | $R^3$ | $R^4$ |
|---|---|---|---|---|---|
| 58) | 3-indolyl | H | H | H | CONH-phenyl |
| 59) | 3-indolyl | H | H | H | CONH-(4-F-phenyl) |
| 60) | 3-indolyl | H | $CH_3$ | H | $CONHCH_3$ |
| 61) | 3-indolyl | H | $CH_3$ | H | $CONHCH_2CH_3$ |
| 62) | 3-indolyl | H | $CH_3$ | H | $CONH(CH_2)_2CH_3$ |
| 63) | 3-indolyl | H | $CH_3$ | H | $CONHCH(CH_3)_2$ |
| 64) | 3-indolyl | H | $CH_3$ | H | $CONH(CH_2)_3CH_3$ |
| 65) | 3-indolyl | H | $CH_3$ | H | $CONH(CH_2)_5CH_3$ |
| 66) | 3-indolyl | H | $CH_3$ | H | CONH-cyclohexyl |
| 67) | 3-indolyl | H | $CH_3$ | H | $CONHCH_2$-phenyl |

-continued
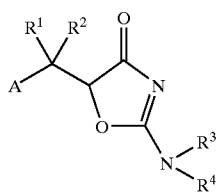
| Compound Number | A | R¹ | R² | R³ | R⁴ |
|---|---|---|---|---|---|
| 68) | 3-indolyl | H | CH₃ | H | CONH-phenyl |
| 69) | 3-indolyl | H | CH₃ | H | CONH-(4-fluorophenyl) |
| 70) | 3-indolyl | H | CH₃ | CH₃ | CONHCH₃ |
| 71) | 3-indolyl | H | CH₃ | CH₃ | CONHCH₂CH₃ |
| 72) | 3-indolyl | H | CH₃ | CH₃ | CONHCH(CH₃)₂ |
| 73) | 3-indolyl | H | CH₃ | CH₃ | CONH(CH₂)₂CH₃ |
| 74) | 3-indolyl | H | CH₃ | CH₃ | CONH(CH₂)₃CH₃ |
| 75) | 3-indolyl | H | CH₃ | CH₃ | CONH(CH₂)₄CH₃ |
| 76) | 3-indolyl | H | CH₃ | CH₃ | CONH(CH₂)₅CH₃ |
| 77) | 3-indolyl | H | CH₃ | CH₃ | CONH-cyclopropyl |

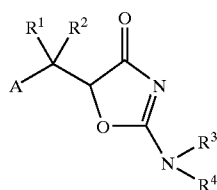

| Compound Number | A | R¹ | R² | R³ | R⁴ |
|---|---|---|---|---|---|
| 78) | 3-indolyl | H | $CH_3$ | $CH_3$ | CONH-cyclobutyl |
| 79) | 3-indolyl | H | $CH_3$ | $CH_3$ | CONH-cyclohexyl(H) |
| 80) | 3-indolyl | H | $CH_3$ | $CH_3$ | $CONHCH_2$-phenyl |
| 81) | 3-indolyl | H | $CH_3$ | $CH_3$ | CONH-phenyl |
| 82) | 3-indolyl | H | $CH_3$ | $CH_3$ | CONH-(4-Cl-phenyl) |
| 83) | 3-indolyl | H | $CH_3$ | $CH_3$ | CONH-(4-Br-phenyl) |
| 84) | 3-indolyl | H | $CH_3$ | $CH_3$ | CONH-(4-F-phenyl) |
| 85) | 3-indolyl | H | $CH_3$ | $CH_3$ | CONH-(4-$CH_3$-phenyl) |
| 86) | 3-indolyl | H | $CH_3$ | $CH_3$ | CONH-(4-$OCH_3$-phenyl) |
| 87) | 3-indolyl | H | $CH_3$ | $CH_3$ | CONH-(4-$CF_3$-phenyl) |

-continued
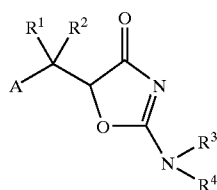
| Compound Number | A | R¹ | R² | R³ | R⁴ |
|---|---|---|---|---|---|
| 88) | 3-indolyl | CH₃ | CH₃ | CH₃ | CONHCH₃ |
| 89) | 3-indolyl | CH₃ | CH₃ | CH₃ | CONHCH₂CH₃ |
| 90) | 3-indolyl | CH₃ | CH₃ | CH₃ | CONH-phenyl |
| 91) | 3-indolyl | CH₃ | CH₃ | CH₃ | CONH-(4-chlorophenyl) |
| 92) | 3-indolyl | H | H | H | CO-(2-thienyl) |
| 93) | 3-indolyl | H | H | H | CO-(3-thienyl) |
| 94) | 3-indolyl | H | H | H | CO-(2-furyl) |
| 95) | 3-indolyl | H | H | H | CO-(3-furyl) |
| 96) | 3-indolyl | H | H | H | CO-(2-pyridyl) |
| 97) | 3-indolyl | H | H | H | CO-(3-pyridyl) |

-continued
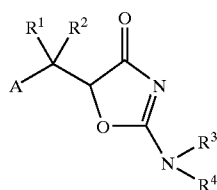
| Compound Number | A | R¹ | R² | R³ | R⁴ |
|---|---|---|---|---|---|
| 98) | 3-indolyl | H | H | H | CO-(4-pyridyl) |
| 99) | 3-indolyl | H | CH₃ | CH₃ | CO-(2-thienyl) |
| 100) | 3-indolyl | H | CH₃ | CH₃ | CO-(3-thienyl) |
| 101) | 3-indolyl | H | CH₃ | CH₃ | CO-(2-furyl) |
| 102) | 3-indolyl | H | CH₃ | CH₃ | CO-(3-furyl) |
| 103) | 3-indolyl | H | CH₃ | CH₃ | CO-(2-pyridyl) |
| 104) | 3-indolyl | H | CH₃ | CH₃ | CO-(3-pyridyl) |
| 105) | 3-indolyl | H | CH₃ | CH₃ | CO-(4-pyridyl) |
| 106) | 3-indolyl | H | CH₃ | CH₃ | COCH₂-(2-thienyl) |
| 107) | 3-indolyl | H | CH₃ | CH₃ | COCH₂-(3-thienyl) |

-continued
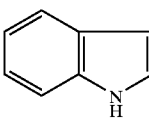
| Compound Number | A | R¹ | R² | R³ | R⁴ |
| --- | --- | --- | --- | --- | --- |
| 108) | 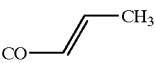 | H | CH₃ | CH₃ | 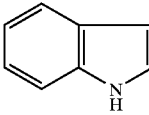 |
| 109) | 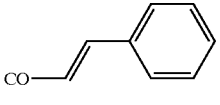 | H | CH₃ | CH₃ | 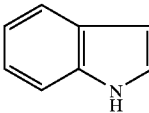 |
| 110) | 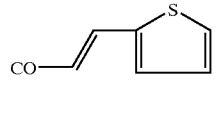 | H | CH₃ | CH₃ | 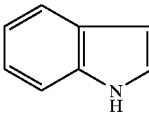 |
| 111) | 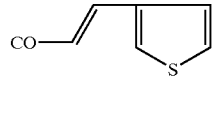 | H | CH₃ | CH₃ | 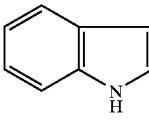 |
| 112) | 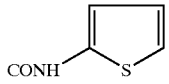 | H | CH₃ | CH₃ | 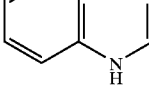 |
| 113) | 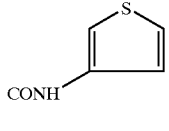 | H | CH₃ | CH₃ | 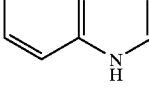 |
| 114) | 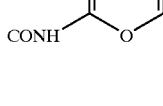 | H | CH₃ | CH₃ | 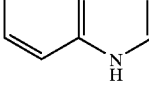 |
| 115) | 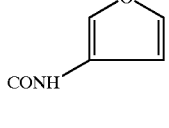 | H | CH₃ | CH₃ | 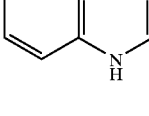 |
| 116) | 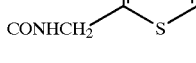 | H | CH₃ | CH₃ | 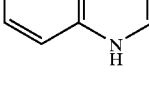 |
| 117) | 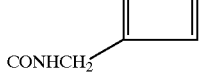 | H | CH₃ | CH₃ | |

-continued

| Compound Number | A | R¹ | R² | R³ | R⁴ |
|---|---|---|---|---|---|
| 118) | benzothiophen-3-yl | H | H | H | H |
| 119) | benzothiophen-3-yl | H | H | H | CO-phenyl |
| 120) | benzothiophen-3-yl | H | H | H | CONH-phenyl |
| 121) | benzothiophen-3-yl | H | CH₃ | CH₃ | H |
| 122) | benzothiophen-3-yl | H | CH₃ | CH₃ | CO-phenyl |
| 123) | benzothiophen-3-yl | H | CH₃ | CH₃ | CO-thiophen-2-yl |
| 124) | benzothiophen-3-yl | H | CH₃ | CH₃ | CONH-phenyl |
| 125) | benzothiophen-3-yl | H | CH₃ | CH₃ | CONH-thiophen-2-yl |
| 126) | benzofuran-3-yl | H | H | H | H |
| 127) | benzofuran-3-yl | H | H | H | CO-phenyl |
| 128) | benzofuran-3-yl | H | H | H | CONH-phenyl |

-continued

| Compound Number | A | R¹ | R² | R³ | R⁴ |
|---|---|---|---|---|---|
| 129) | benzofuran-3-yl | H | CH₃ | CH₃ | H |
| 130) | benzofuran-3-yl | H | CH₃ | CH₃ | CO-phenyl |
| 131) | benzofuran-3-yl | H | CH₃ | CH₃ | CO-(thiophen-2-yl) |
| 132) | benzofuran-3-yl | H | CH₃ | CH₃ | CONH-phenyl |
| 133) | benzofuran-3-yl | H | CH₃ | CH₃ | CONH-(thiophen-2-yl) |
| 134) | 1H-indazol-3-yl | H | H | H | H |
| 135) | 1H-indazol-3-yl | H | H | H | CO-phenyl |
| 136) | 1H-indazol-3-yl | H | H | H | CONH-phenyl |
| 137) | 1H-indazol-3-yl | H | CH₃ | CH₃ | H |
| 138) | 1H-indazol-3-yl | H | CH₃ | CH₃ | CO-phenyl |
| 139) | 1H-indazol-3-yl | H | CH₃ | CH₃ | CO-(thiophen-2-yl) |

-continued
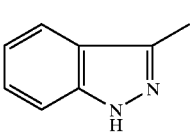
| Compound Number | A | R¹ | R² | R³ | R⁴ |
|---|---|---|---|---|---|
| 140) | 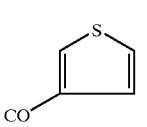 | H | CH₃ | CH₃ | 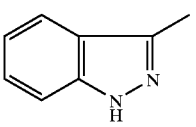 |
| 141) | 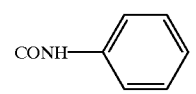 | H | CH₃ | CH₃ | 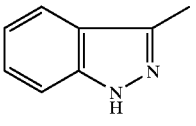 |
| 142) | 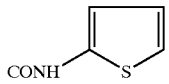 | H | CH₃ | CH₃ | 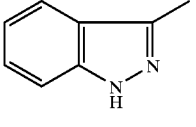 |
| 143) | 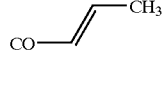 | H | CH₃ | CH₃ | 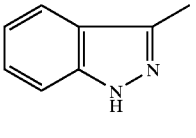 |
| 144) | 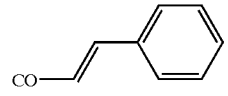 | H | CH₃ | CH₃ | 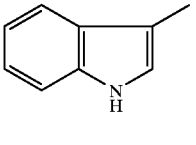 |
| 145) | 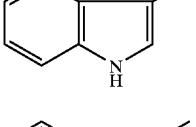 | H | CH₃ | CH₃ | COOCH₃ |
| 146) | 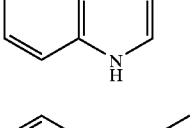 | H | CH₃ | CH₃ | COOCH₂CH₃ |
| 147) | 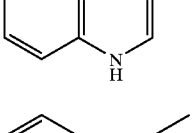 | H | CH₃ | CH₃ | COO(CH₂)₂CH₃ |
| 148) | 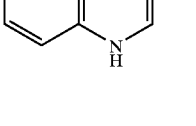 | H | CH₃ | CH₃ | COOCH(CH₃)₂ |
| 149) | 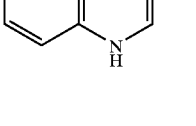 | H | CH₃ | CH₃ | COO(CH₃)₃CH₃ |

-continued
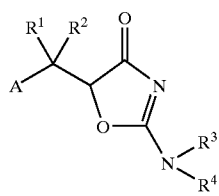
| Compound Number | A | R¹ | R² | R³ | R⁴ |
|---|---|---|---|---|---|
| 150) | 3-indolyl | H | CH₃ | CH₃ | COOCH₂CH(CH₃)₃ |
| 151) | 3-indolyl | H | CH₃ | CH₃ | COOC(CH₃)₃ |
| 152) | 3-indolyl | H | CH₃ | CH₃ | COO(CH₂)₄CH₃ |
| 153) | 3-indolyl | H | CH₃ | CH₃ | COO(CH₂)₅CH₃ |
| 154) | 3-indolyl | H | CH₃ | CH₃ | COOCH₂—C₆H₅ |
| 155) | 3-indolyl | H | CH₃ | CH₃ | SO₂CH₃ |
| 156) | 3-indolyl | H | CH₃ | CH₃ | SO₂CH₂CH₃ |
| 157) | 3-indolyl | H | CH₃ | CH₃ | SO₂(CH₂)₂CH₃ |
| 158) | 3-indolyl | H | CH₃ | CH₃ | SO₂(CH₂)₃CH₃ |
| 159) | 3-indolyl | H | CH₃ | CH₃ | SO₂(CH₂)₄CH₃ |

-continued

| Compound Number | A | R¹ | R² | R³ | R⁴ |
|---|---|---|---|---|---|
| 160) | 3-indolyl | H | CH₃ | CH₃ | SO₂(CH₂)₅CH₃ |
| 161) | 3-indolyl | H | CH₃ | CH₃ | SO₂-cyclopropyl |
| 162) | 3-indolyl | H | CH₃ | CH₃ | SO₂-cyclohexyl |
| 163) | 3-indolyl | H | CH₃ | CH₃ | SO₂-phenyl |
| 164) | 3-indolyl | H | CH₃ | CH₃ | SO₂-(4-Cl-phenyl) |
| 165) | 3-indolyl | H | CH₃ | CH₃ | SO₂-(4-CH₃-phenyl) |
| 166) | 3-indolyl | H | CH₃ | CH₃ | SO₂-(2-naphthyl) |

The above compounds may be racemates or optical isomers.

Compound (I) or a salt thereof, used for the present invention, is effective as an antibacterial agent in the prevention or treatment of "duodenal ulcer, gastric ulcer, gastritis (including chronic gastritis), gastric cancer etc." caused by *Helicobacter pylori* infection as described above, because it possesses antibacterial activity, especially potent antibacterial activity against the bacteria of the genus Helicobacter, represented by *Helicobacter pylori*.

The preparation of the present invention, containing compound (I) or a pharmacologically acceptable salt thereof, can be orally or non-orally administered as an antibacterial or antiulcer agent to mammals (e.g., humans, dogs, cats, monkeys, rats, mice, horses, bovines), oral administration being normally preferred.

Examples of dosage forms for oral administration include tablets (including sugar-coated tablets and film-coated tablets), pills, granules, powders, capsules (including soft capsules), syrups, emulsions and suspensions. Examples of dosage forms for non-oral administration include injectable preparations, infusions, drip infusions and suppositories.

The content of compound (I) or a salt thereof in the preparation of the present invention is normally 2 to 85% by weight, preferably 5 to 70% by weight.

For preparing compound (I) or a salt thereof in the above-mentioned dosage forms, known production methods in common use in relevant fields are applicable. In producing the above-mentioned dosage forms, excipients, binders, disintegrants, lubricants, sweetening agents, surfactants, suspending agents, emulsifiers etc. in common use in the field of pharmaceutical making may be added in appropriate amounts as necessary.

When compound (I) or a salt thereof is prepared as tablets, for example, excipients, binders, disintegrants, lubricants etc. may be contained; when compound (I) or a salt thereof is prepared as pills or granules, excipients, binders, disintegrants etc. may be contained. When, compound (I) or a salt thereof is prepared as powders or capsules, excipients etc. may be contained; when compound (I) or a salt thereof is prepared as syrups, sweetening agents etc. may be contained; when compound (I) or a salt thereof is prepared as emulsions or suspensions, suspending agents, surfactants, emulsifiers etc. may be contained. Examples of excipients include lactose, saccharose, glucose, starch, sucrose, microcrystalline cellulose, powdered glycyrrhiza, mannitol, sodium hydrogen carbonate, calcium phosphate and calcium sulfate. Examples of binders include 5–10% by weight starch glue solutions, 10–20% by weight gum arabic solutions or gelatin solutions, 1–5% by weight tragacanth solutions, carboxymethyl cellulose solutions, sodium alginate solutions and glycerol. Examples of disintegrants include starch and calcium carbonate. Examples of lubricants include magnesium stearate, stearic acid, calcium stearate and purified talc. Examples of sweetening agents include glucose, fructose, invert sugar, sorbitol, xylitol, glycerol and simple syrups. Examples of surfactants include sodium lauryl sulfate, polysorbate 80, sorbitan monofatty acid ester and stearic acid polyoxyl 40. Example of suspending agents include gum arabic, sodium alginate, carboxymethyl cellulose sodium, methyl cellulose and bentonite. Examples of emulsifiers include gum arabic, tragacanth, gelatin and polysorbate 80.

For preparing compound (I) or a salt thereof in the above-mentioned dosage forms, coloring agents, preservatives, flavoring agents, correctives, stabilizers, thickening agents etc. in common use in the field of pharmaceutical making may be added in appropriate amounts as desired. The preparation of the present invention, which contains a compound represented by general formula (I) or a pharmaceutically acceptable salt thereof, is stable and of low toxicity, and can be safely used. Varying depending on patient condition and body weight, kind of compound, route of administration etc., the daily dose of the preparation of the present invention is normally 1 to 500 mg, preferably about 10 to 200 mg, based on active ingredient content (compound (I) or a salt thereof), per adult (weighing about 60 kg) for oral administration in patients with gastric ulcer caused by *Helicobacter pylori* infection.

Within the above-described dose range, no toxicity is seen.

Also, in the preparation of the present invention, compound (I) or a salt thereof can be used in combination with other antibacterial agents and antiulcer agents.

Other antibacterial agents that can be used in combination with compound (I) or a salt thereof include, for example, nitroimidazole antibiotics (e.g., tinidazole and metronidazole), tetracyclines (e.g., tetracycline, doxycycline and minocycline), penicillins (e.g., amoxicillin, ampicillin and mezlocillin), cephalosporins (e.g., cefaclor, cefadroxil, cefazolin, cefuroxime, cefuroxime axetil, cephalexin, cefpodoxime proxetil, ceftazidime and ceftriaxone), carbapenems (e.g., imipenem and meropenem), aminoglycosides (e.g., paromomycin), macrolide antibiotics (e.g., erythromycin, clarithromycin and azithromycin), lincosamide antibiotics (e.g., clindamycin), rifamycins (e.g., rifampicin) and quinolone antibiotics (e.g., ciprofloxacin, ofloxacin) nitrofurantoin. Antiulcer agents that can be used in combination with compound (I) or a salt thereof include, for example, proton pump inhibitors (e.g., omeprazole, lansoprazole, pantoprazole, rabeprazole) Histamine $H_2$ antagonists (e.g., ranitidine, cimetidine and famotidine), and mucosa-protecting antiulcer agents (e.g., sofalcone, plaunotol, teprenone, sucralfate).

The above-described other antibacterial agents and antiulcer agents may be used in combination of two or more kinds. In this case, the dose of antibacterial agent is normally 1 to 500 mg, preferably 5 to 200 mg, per adult per day in oral administration; the dose of antiulcer agent is normally 0.5 to 1,000 mg, preferably 1 to 500 mg, per adult per day in oral administration.

The compound of formula (I) or a salt thereof can, for example, be produced by methods A through E below.

Method A

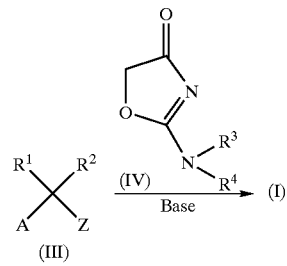

In the above formulas, Z represents a halogen atom or —O—$SO_2R^6$ ($R^6$ represents a lower alkyl group or a substituted phenyl group); the other symbols have the same definitions as those shown above.

The halogen atom represented by Z in formula (III) is exemplified by fluorine, chlorine, bromine and iodine. The lower alkyl group represented by $R^6$ is exemplified by alkyl groups having 1 to 6 carbon atoms, such as methyl, ethyl, propyl, isopropyl, butyl, isobutyl, sec-butyl, tert-butyl, pentyl, isopentyl, neopentyl, tert-pentyl, 1-ethylpropyl, hexyl, isohexyl, 1,1-dimethylbutyl, 2,2-dimethylbutyl, 3,3-dimethylbutyl and 2-ethylbutyl, with preference given to those having 1 to 4 carbon atoms, such as methyl, ethyl, propyl, isopropyl, butyl and isobutyl.

Useful substituents for the substituted phenyl group represented by $R^6$ include, for example, lower alkyl groups (same as those mentioned to exemplify the lower alkyl group represented by $R^6$ above), lower alkoxy groups (e.g., those having 1 to 4 carbon atoms, such as methoxy, ethoxy, propoxy, isopropoxy and butoxy), halogen atoms (e.g., fluorine, chlorine, bromine, iodine), nitro groups, cyano groups and carboxyl groups.

This method is conducted by reacting compound (III) or a salt thereof with compound (IV) in the presence of a base. The salt of compound (III) is exemplified by the acid addition salts mentioned to exemplify acids that form an acid addition salt with compound (I). This reaction is normally carried out in a solvent; a solvent that does not interfere with the reaction is chosen as appropriate. Such solvents include, for example, alcohols such as methanol, ethanol, propanol, isopropanol, butanol and tert-butanol; ethers such as dioxane, tetrahydrofuran, diethyl ether, tert-butyl methyl ether, diisopropyl ether and ethylene glycol-dimethyl ether; esters such as ethyl formate, ethyl acetate and n-butyl acetate; halogenated hydrocarbons such as dichloromethane, chloroform, carbon tetrachloride, trichlene and 1,2-dichloroethane; hydrocarbons such as n-hexane, benzene and toluene; amides such as formamide, N,N-dimethylformamide and N,N-dimethylacetamide; ketones such as acetone, methyl ethyl ketone and methyl isobutyl ketone; nitriles such as acetonitrile and propionitrile; dimethyl sulfoxide, sulfolane, hexamethylphosphoramide and water; these solvents are used as simple or mixed solvents.

Useful bases include, for example, $C_{1-6}$ alkyl or aryl lithiums such as methyl lithium, ethyl lithium, n-butyl lithium, sec-butyl lithium, tert-butyl lithium and phenyl lithium; lithium alkylamides having 2 to 6 carbon atoms, such as lithium dimethylamide, lithium diethylamide and lithium diisopropylamide; metal hydrides such as lithium hydride and sodium hydride; metal alkoxides having 1 to 6 carbon atoms, such as lithium ethoxide, lithium tert-butoxide, sodium methoxide, sodium ethoxide and potassium tert-butoxide; amides such as lithium amide, potassium amide and sodium amide; inorganic bases such as lithium hydroxide, potassium hydroxide, sodium hydroxide, sodium carbonate, potassium carbonate and sodium hydrogen carbonate; and tertiary amines such as triethylamine, tri(n-propyl)amine, tri(n-butyl)amine, diisopropylethylamine, cyclohexyldimethylamine, pyridine, lutidine, γ-collidine, N,N-dimethylaniline, N-methylpiperidine, N-methylpyrrolidine and N-methylmorpholine. The reaction is carried out using 1 to 5 mol, preferably 1 to 3 mol, of compound (IV) per mol of compound (III). Reaction temperature is normally about −80 to 100° C., preferably −50 to 60° C. Reaction time is normally 1 minute to 72 hours, preferably 15 minutes to 24 hours, depending on the kinds of compounds (III) and (IV), the kind of solvent, reaction temperature etc.

Method B

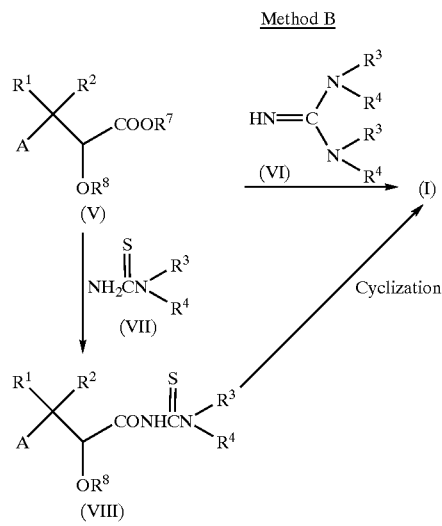

In the above formulas, $R^7$ represents hydrogen or a lower alkyl group; $R^8$ represents hydrogen or a hydroxyl group-protecting group; the other symbols have the same definitions as those shown above.

The lower alkyl group represented by $R^7$ is exemplified by the same lower alkyl groups as those mentioned to exemplify the lower alkyl group used for $R^6$ in method A.

The hydroxyl group-protecting group represented by $R^8$ may be any one, as long as it does not interfere with the reaction; preferable examples thereof include ether-forming protecting groups such as methoxymethyl, benzyloxymethyl, tert-butoxymethyl, 2-methoxyethoxymethyl, 2-(trimethylsilyl)ethoxymethyl, methylthiomethyl, 2-tetrahydropyranyl, 4-methoxy-4-tetrahydropyranyl, 2-tetrahydrofranyl, benzyl, p-methoxybenzyl, p-nitrobenzyl, o-nitrobenzyl and trityl; silyl ether-forming protecting groups such as trimethylsilyl, triethylsilyl, triisopropylsilyl, isopropyldimethylsilyl, diethylisopropylsilyl, tert-butyldimethylsilyl, tert-butyldiphenylsilyl, tribenzylsilyl, triphenylsilyl and methyldiphenylsilyl; and ester-forming protecting groups such as formyl, acetyl, chloroacetyl, dichloroacetyl, trichloroacetyl, pivaloyl and benzoyl.

When $R^8$ in formula (V) is hydrogen, compound (V) or a salt thereof is reacted with compound (VI). The salt of compound (V) is exemplified by acid adduct salts with the acids mentioned to exemplify acids that form an acid adduct salt with compound (I). This reaction is normally carried out in a solvent and, if necessary, in the presence of a base. Such solvents and bases are identical to the solvents and bases mentioned for method A above. The reaction is carried out using 1 to 10 mol, preferably 1 to 5 mol, of compound (VI) per mol of compound (V) or salt thereof. Reaction temperature is normally about −30 to 200° C., preferably −10 to 150° C. Reaction time is normally 1 minute to 120 hours, preferably 15 minutes to 48 hours, depending on the kinds of compounds (V) and (VI), the kinds of solvent and base, reaction temperature etc.

Compound (I) can also be produced by producing compound (VIII) from compounds (V) and (VII) and cyclizing compound (VIII). This method involves the acylation of compound (VII) or a salt thereof with compound (V), a salt thereof or a reactive derivative thereof.

Specifically, free acid (V), a salt thereof (inorganic salt, organic salt) or a reactive derivative thereof (e.g., acid halide, acid azide, acid anhydride, mixed acid anhydride, active amide, active ester, active thioester etc.) is subjected to acylation reaction. Inorganic salts include alkali metal salts (e.g., sodium salt, potassium salt) and alkaline earth metal salts (e.g., calcium salt). Organic salts include, for example, trimethylamine salt, triethylamine salt, tert-butyldimethylamine salt, dibenzylmethylamine salt, benzyldimethylamine salt, N,N-dimethylaniline salt, pyridine salt and quinoline salt. Acid halides include, for example, acid chloride and acid bromide. Mixed acid anhydrides include mono-$C_{1-4}$ alkylcarbonic acid mixed acid anhydrides (e.g., mixed acid anhydrides of free acid (V) and monomethylcarbonic acid, monoethylcarbonic acid, monoisopropylcarbonic acid, monoisobutylcarbonic acid, mono-tert-butylcarbonic acid, monobenzylcarbonic acid, mono(p-nitrobenzyl)carbonic acid, monoallylcarbonic acid etc.), $C_{1-6}$ aliphatic carboxylic acid mixed acid anhydrides (e.g., mixed acid anhydrides of free acid (V) and acetic acid, cyanoacetic acid, propionic acid, butyric acid, isobutyric acid, valeric acid, isovaleric acid, pivalic acid, trifluoroacetic acid, trichloroacetic acid, acetoacetic acid etc.), $C_{7-11}$ aromatic carboxylic acid mixed acid anhydrides (e.g., mixed acid anhydrides of free acid (V) and benzoic acid, p-toluic acid, p-chlorobenzoic acid etc.) and organic sulfonic acid mixed acid anhydrides (e.g., mixed acid anhydrides with methanesulfonic acid, ethanesulfonic acid, benzenesulfonic acid, p-toluenesulfonic acid etc.). Active amides include amides with nitrogen-containing heterocyclic compounds [e.g., acid amides of free acid (V) and pyrazole, imidazole, benzotriazole etc.; these nitrogen-containing heterocyclic compounds may be substituted for by $C_{1-4}$ alkyls (e.g., methyl, ethyl, propyl, isopropyl, butyl, isobutyl, sec-butyl, tert-butyl), $C_{1-6}$ alkoxys (e.g., methoxy, ethoxy, propoxy, isopropoxy, butoxy, tert-butoxy), halogen atoms (e.g., fluorine, chlorine, bromine), oxo, thioxo, $C_{1-6}$ alkylthios (e.g., methylthio, ethylthio, propylthio, butylthio) etc.].

Active esters include, for example, organic phosphoric acid esters (e.g., diethoxyphosphoric acid esters, diphenoxyphosphoric acid esters), p-nitrophenyl ester, 2,4-dinitrophenyl ester, cyanomethyl ester, pentachlorophenyl ester, N-hydroxysuccinimide ester, N-hydroxyphthalimide ester, 1-hydroxybenzotriazole ester, 6-chloro-1-hydroxybenzotriazole ester and 1-hydroxy-1H-2-pyridone ester. Active thioesters include esters with aromatic heterocyclic thiol compounds [their heterocyclic rings may be substituted for by $C_{1-4}$ alkyls (e.g., methyl, ethyl, propyl, isopropyl, butyl, isobutyl, sec-butyl, tert-butyl), $C_{1-6}$ alkoxys (e.g., methoxy, ethoxy, propoxy, isopropoxy, butoxy, tert-butoxy), halogen atoms (e.g., fluorine, chlorine, bromine), $C_{1-6}$ alkylthios (e.g., methylthio, ethylthio, propylthio, butylthio) etc.] [e.g., 2-pyridylthiol ester, 2-benzothiazolylthiol ester].

The salt of compound (VII) is exemplified by salts with alkali metals (e.g., potassium, sodium, lithium), salts with alkaline earth metals (e.g., calcium, magnesium) and acid addition salts (acid adduct salts with the acids mentioned to exemplify acids that form an acid addition salt with compound (I)).

This reaction is normally carried in a solvent; a solvent that does not interfere with the reaction is chosen as appropriate. Such solvents include, for example, ethers such as dioxane, tetrahydrofuran, diethyl ether, tert-butyl methyl ether, diisopropyl ether and ethylene glycol-dimethyl ether; esters such as ethyl formate, ethyl acetate and butyl acetate; halogenated hydrocarbons such as dichloromethane, chloroform, carbon tetrachloride, trichlene and 1,2-dichloroethane; hydrocarbons such as n-hexane, benzene and toluene; amides such as formamide, N,N-dimethylformamide and N,N-dimethylacetamide; ketones such as acetone, methyl ethyl ketone and methyl isobutyl ketone; nitriles such as acetonitrile and propionitrile; dimethyl sulfoxide, sulfolane, hexamethylphosphoramide and water; these solvents are used as simple or mixed solvents. The amount of compound (VII) used is normally 1 to 10 mol, preferably 1 to 5 mol, per mol of compound (V). The reaction is normally carried out in the temperature range from −80 to 200° C., preferably from −40 to 150° C., and most preferably from −30 to 100° C. Reaction time is normally 1 minute to 72 hours, preferably 15 minutes to 24 hours, depending on the kinds of compounds (V) and (VII), the kind of solvent (also mixing ratio in the case of a mixed solvent), reaction temperature etc. When compound (V) is used as an acid halide, the reaction can be carried out in the presence of a deoxidizer to remove the released hydrogen halide from the reaction system. Such deoxidizers include, for example, inorganic bases such as sodium carbonate, potassium carbonate, calcium carbonate and sodium hydrogen carbonate; tertiary amines such as triethylamine, tripropylamine, tributylamine, cyclohexyldimethylamine, pyridine, lutidine, γ-collidine, N,N-dimethylaniline, N-methylpiperidine, N-methylpyrrolidine and N-methylmorpholine; and alkylene oxides such as propylene oxide and epichlorohydrin.

Compound (VIII) can be then cyclized to yield compound (I) after the hydroxyl group-protecting group $R^8$ is removed as necessary. Depending on the kind of protecting group, this deprotection reaction can be carried out by a known method chosen as appropriate. For example, deprotection can be achieved with an acid (e.g., formic acid, acetic acid, propionic acid, hydrochloric acid, sulfuric acid, hydrobromic acid, phosphoric acid, methanesulfonic acid, ethanesulfonic acid, p-toluenesulfonic acid) or by catalytic reduction [Raney nickel, platinum, palladium, rhodium, or the like, for example, used as a catalyst at normal pressure or increased pressure (2 to 100 atm)] in the case of ether-forming protecting groups, with one of the above-mentioned acids or a Lewis acid (e.g., zinc chloride, zinc bromide, aluminum chloride, titanium chloride) or a fluoride (e.g., potassium fluoride, sodium fluoride, tetraethylammonium fluoride, tetra-n-butylammonium fluoride) in the case of silyl ether-forming protecting groups, or with a base (e.g., potassium hydrogen carbonate, sodium hydrogen carbonate, potassium carbonate, sodium carbonate, lithium hydroxide, potassium hydroxide, sodium hydroxide) in the case of ester-forming protecting groups. The reaction is normally carried out in a solvent; such solvents are exemplified by the solvents used for method A.

In the case of ether-forming protecting groups or silyl ether-forming protecting groups, the amount of acid or Lewis acid used is normally 0.001 to 100 mol, preferably 0.01 to 50 mol. per mol of compound (V). Reaction temperature is normally −50 to 150° C., preferably −20 to 100° C. Reaction time is normally 1 minute to 72 hours, preferably 15 minutes to 48 hours.

In the case of ester-forming protecting groups, the amount of base used is normally 0.01 to 50 mol, preferably 0.1 to 20 mol, per mol of compound (V). Reaction temperature is normally −20 to 150° C., preferably −10 to 100° C. Reaction time is normally 1 minute to 72 hours, preferably 15 minutes to 48 hours.

Compound (VIII) thus deprotected is cyclized to compound (I). This reaction is normally carried out in a solvent. Such solvents are exemplified by the solvents used for method A. Reaction temperature is normally −10 to 200° C., preferably −5 to 150° C. In this reaction, a base may be used as a catalyst; such bases are exemplified by the bases used for method A. To promote the reaction, there may be used, for example, 2-chloro-3-methylbenzoxazolium tetrafluoroborate, 2-chloro-3-ethylbenzoxazolium tetrafluoroborate, 2-chloro-3-methylbenzothiazolium tetrafluoroborate, 2-chloro-3-ethylbenzothiazolium fluoroborate, 2-chloro-1-methylpyridinium tetrafluoroborate and 2-chloro-1-ethylpyridinium tetrafluoroborate. The amount of reaction promoter used is normally 1 to 10 mol, preferably 1 to 3 mol, per mol of compound (VIII). A base is also used when a reaction promoter is used. Such bases are exemplified by the bases used for method A. Reaction temperature is normally −30 to 150° C., preferably −20 to 100° C. Reaction time is normally 1 minute to 72 hours, preferably 15 minutes to 48 hours.

When one of $R^3$ and $R^4$ is an acyl group, an esterified carboxyl group or a carbamoyl group that may have a substituent, compound (I) can be produced by methods C, D and E below.

Of the compounds of formula (I), compound (Ib), which has an acyl group for $R^3$ or $R^4$, can be produced by method C.

Method C

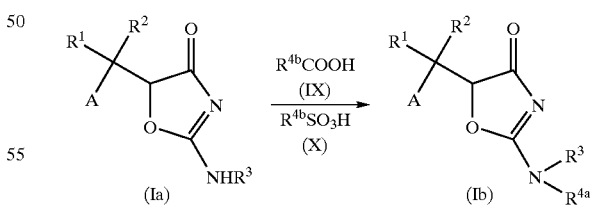

In these formulas, $R^{4a}$ represents an acyl group; $R^{4b}$ represents a group resulting from removal of the carbonyl group or sulfonyl group from an acyl group; the other symbols have the same definitions as those shown above.

The acyl group represented by $R^{4a}$ means an acyl group represented by $R^4$; the "acyl group" in the "group resulting from removal of the carbonyl group or sulfonyl group from an acyl group" represented by $R^{4b}$ means an acyl group represented by $R^4$.

In this reaction, compound (Ia) or a salt thereof can be acylated with compound (IX) or (X) or a reactive derivative thereof to yield compound (Ib). The salt of compound (Ia) is exemplified by the same acid adduct salts as those mentioned to exemplify the salt of compound (I). The reactive derivative of compound (IX) is exemplified by the reactive derivatives mentioned for method B. The reactive derivative of compound (X) is exemplified by sulfonic acid halides (e.g., sulfonyl bromide, sulfonyl chloride) and sulfonic anhydride; the reaction is carried out by the method described for method B or a modification thereof.

In the compounds of formula (I), compound (Ic), which has an esterified carboxyl group for $R^4$, can be produced by method D.

Method D

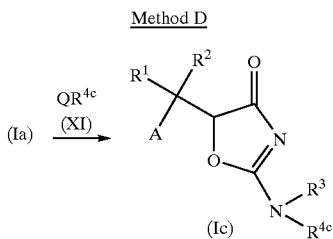

In these formulas, $R^{4c}$ represents an esterified carboxyl group; Q represents a halogen atom; the other symbols have the same definitions as those shown above.

$R^{4c}$ is any one of the carboxyl groups that may be esterified, represented by $R^4$, except the free carboxyl group.

The halogen represented by Q is exemplified by fluorine, chlorine, bromine and iodine. This reaction is carried out by reacting compound (Ia) or a salt thereof and compound (XI). The salt of compound (Ia) is exemplified by the acid adduct salts mentioned to exemplify the acid adduct salt of compound (Ia) for reaction D above. This reaction is normally carried out in a solvent; such solvents are exemplified by the solvents used for method B. In this reaction, a hydrogen halide is released. To remove the hydrogen halide, the reaction can be carried out in the presence of an acid scavenger. Such acid scavenger includes, for example, inorganic bases such as sodium carbonate, potassium carbonate, calcium carbonate and sodium hydrogen carbonate; tertiary amines such as triethylamine, tripropylamine, tributylamine, cyclohexyldimethylamine, pyridine, lutidine, γ-collidine, N,N-dimethylaniline, N-methylpiperidine, N-methylpyrrolidine and N-methylmorpholine; and alkylene oxides such as propylene oxide and epichlorohydrin.

The amount of compound (XI) used is normally 1 to 20 moll preferably 1 to 10 mol, per mol of compound (Ia). Reaction temperature is normally −30 to 120° C., preferably −20 to 80° C. Reaction time is normally 1 minute to 72 hours, preferably 15 minutes to 48 hours.

Of the compounds of formula (I), compound (Id), which has a carbamoyl group which may be substituted, can be produced by method E.

Method E

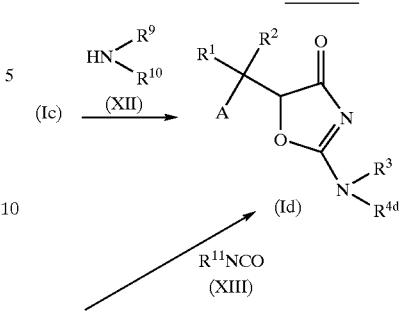

In these formulas, $R^{4d}$ represents a carbamoyl group which may be substituted; $R^9$, $R^{10}$ and $R^{11}$, whether identical or not, represent hydrogen or one of the substituents mentioned to exemplify the substituent for the carbamoyl group represented by $R^4$, which may be substituted; the other symbols have the samel definitions as those shown above.

In this method, compound (Ic) or a salt thereof can be reacted with compound (XII) to yield compound (Id). The salt of compound (Ic) is exemplified by the same acid addition salts as those mentioned to exemplify the salt of compound (I). This reaction is normally carried out in a solvent; such solvents are exemplified by the solvents used for method A. The amount of compound (XII) used is normally 1 to 100 mol, preferably 1 to 30 mol, per mol of compound (Ic). Reaction temperature is normally −30 to 200° C., preferably −10 to 100° C. Reaction time is normally 1 minute to 72 hours, preferably 15 minutes to 48 hours.

Compound (Id) can also be produced by reacting compound (Ia) with isocyanate derivative (XIII). The reaction is normally carried out in a solvent. Said solvent may be any one, as long as it does not interfere with the reaction. For example, ethers such as dioxane, tetrahydrofuran, diethyl ether, tert-butyl ether, diisopropyl ether and ethylene glycoldimethyl ether; esters such as ethyl formate, ethyl acetate and n-butyl acetate; halogenated hydrocarbons such as dichloromethane, chloroform, carbon tetrachloride, trichlene and 1,2-dichloroethane; hydrocarbons such as n-hexane, benzene and toluene; amides such as formamide, N,N-dimethylformamide and N,N-dimethylacetamide; ketones such as acetone, methyl ethyl ketone and methyl isobutyl ketone; nitriles such as acetonitrile and propionitrile; dimethyl sulfoxide, sulfolane, hexamethylphosphoramide are used as simple or mixed solvents.

The amount of compound (XIII) used is normally 1 to 30 mol, preferably 1 to 15 mol, per mol of compound (Ia). Reaction temperature is normally −20 to 150° C., preferably −10 to 100° C. Reaction time is normally 1 minute to 72 hours, preferably 15 minutes to 48 hours.

Method F

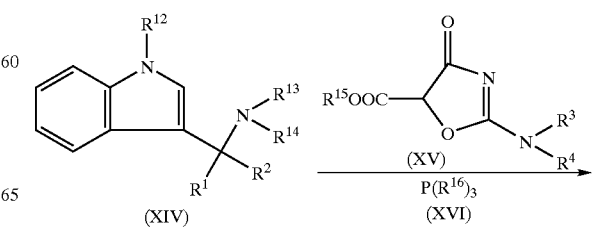

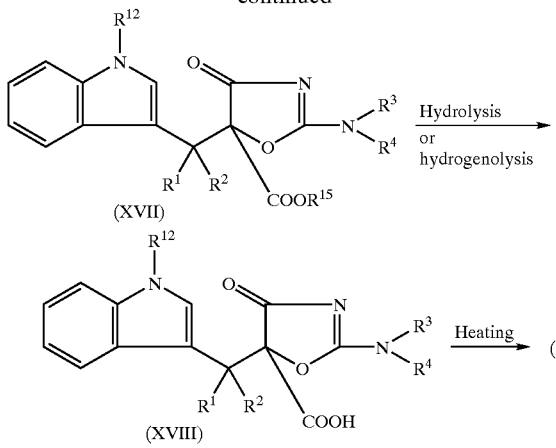

In these formulas, $R^{12}$ represents hydrogen, a lower alkyl group, a cycloalkyl group, an aralkyl group or an acyl group; $R^{13}$ and $R^{14}$, whether identical or not, represent hydrogen or a lower alkyl group; $R^{15}$ represents hydrogen, a lower alkyl group or an aralkyl group; $R^{16}$ represents a lower alkyl group or an aryl group; the other symbols have the same definitions as those shown above.

The lower alkyl group represented by $R^{12}$ in formula (XIV) is exemplified by alkyl groups having 1 to 6 carbon atoms, such as methyl, ethyl, propyl, isopropyl, butyl, isobutyl, sec-butyl, tert-butyl, pentyl, isopentyl, neopentyl, tert-pentyl, 1-ethylpropyl, hexyl, isohexyl, 1,1-dimethylbutyl, 2,2-dimethylbutyl, 3,3-dimethylbutyl and 2-ethylbutyl, with preference given to those having 1 to 4 carbon atoms, such as methyl, ethyl, propyl, isopropyl, butyl and isobutyl. The cycloalkyl group represented by $R^{12}$ is exemplified by cyclopropyl, cyclobutyl, cyclopentyl, cyclohexyl, cycloheptyl, cyclooctyl and cyclononyl, with preference given to cyclopropyl, cyclobutyl, cyclopentyl and cyclohexyl. The aralkyl group represented by $R^{12}$ is exemplified by benzyl, phenethyl and phenylpropyl.

The acyl group represented by $R^{12}$ is exemplified by aliphatic acyl groups such as alkanoyl groups, alkenoyl groups, cycloalkanecarbonyl groups and alkanesulfonyl groups; aromatic acyl groups such as aroyl groups, arylalkanoyl groups, arylalkenoyl groups and arenesulfonyl groups; heterocyclic aromatic acyl groups such as aromatic heterocyclic carbonyl groups and aromatic heterocyclic alkanoyl groups; and non-aromatic heterocyclic carbonyl groups (aliphatic heterocyclic carbonyl groups).

"Alkanoyl groups" mean alkylcarbonyl groups, preferable examples thereof including lower alkanoyl groups having 1 to 8 carbon atoms, such as formyl, acetyl, propionyl, butyryl, isobutyryl, valeryl, isovaleryl, pivaloyl and hexanoyl.

"Alkenoyl groups" mean alkenylcarbonyl groups, preferable examples thereof including $C_{3-6}$ alkenoyl groups such as acryloyl, methacryloyl, crotonoyl and isocrotonoyl.

"Cycloalkanecarbonyl groups" mean cycloalkylcarbonyl groups, preferable examples thereof including those having 4 to 7 carbon atoms, such as cyclopropanecarbonyl groups, cyclobutanecarbonyl groups, cyclopentanecarbonyl groups and cyclohexanecarbonyl groups.

"Alkanesulfonyl groups" mean alkylsulfonyl groups, preferable examples thereof including those having 1 to 4 carbon atoms, such as mesyl, ethanesulfonyl and propanesulfonyl.

"Aroyl groups" mean arylcarbonyl groups, preferable examples thereof including those having 7 to 11 carbon atoms, such as benzoyl, p-toluoyl, 1-naphthoyl and 2-naphthoyl.

"Arylalkanoyl groups" mean alkylcarbonyl groups, substituted for by an aryl group, preferable examples thereof including $C_{6-8}$ aryl-$C_{2-5}$ alkanoyl groups such as phenylacetyl, phenylpropionyl hydroatropoyl and phenylbutyryl.

"Arylalkenoyl groups" mean alkenylcarbonyl groups substituted for by an aryl group, preferable examples thereof including $C_{6-8}$ aryl-$C_{3-5}$ alkenoyl groups such as cinnamoyl and atropoyl.

"Arenesulfonyl groups" mean arylsulfonyl groups, preferable examples thereof including those having 6 to 8 carbon atoms, such as benzenesulfonyl and p-toluenesulfonyl.

Preferable examples of "aromatic heterocyclic carbonyl groups" include furoyl, thenoyl, nicotinoyl, isonicotinoyl, pyrrolecarbonyl, oxazolecarbonyl, thiazolecarbonyl, imidazolecarbonyl and pyrazolecarbonyl.

"Aromatic heterocyclic alkanoyl groups" mean alkylcarbonyl groups substituted for by an aromatic heterocyclic group, preferable examples thereof including aromatic heterocyclic ring-$C_{2-5}$ alkanoyl groups such as thienylacetyl, thienylpropanoyl, furylacetyl, thiazolylacetyl, 1,2,4-thiadiazolylacetyl and pyridylacetyl.

Preferable examples of "non-aromatic heterocyclic carbonyl groups" include aliphatic heterocyclic carbonyls such as azetidinylcarbonyl, pyrrolidinylcarbonyl and piperidinylcarbonyl.

The lower alkyl group represented by $R^{13}$, $R^{14}$, $R^{15}$ or $R^{16}$ in formulas (XIV), (XV) and (XVI) is exemplified by lower alkyl groups represented by $R^{12}$. The aralkyl group represented by $R^{15}$ is exemplified by aralkyl groups represented by $R^{12}$. The aryl group represented by $R^{16}$ is exemplified by phenyl, naphthyl, anthryl, phenanthryl and acenaphthylenyl groups, with preference given to phenyl and naphthyl. These aryl groups may have 1 to 5 substituents. Such substituents include alkyl groups having 1 to 3 carbon atoms (e.g., methyl, ethyl, propyl), alkoxy groups having 1 to 3 carbon atoms (e.g., methoxy, ethoxy, propoxy) and halogen atoms (e.g., fluorine, chlorine, bromine, iodine).

In this method, compounds (XIV) and (XV) are reacted in the presence of compound (XVI) to yield compound (XVII).

This reaction is normally carried out in a solvent; a solvent that does not interfere with the reaction is chosen as appropriate. Such solvents include, for example, alcohols such as methanol, ethanol, propanol, isopropanol, butanol and tert-butanol; ethers such as dioxane, tetrahydrofuran, diethyl ether, tert-butyl methyl ether, diisopropyl ether and ethylene glycol-dimethyl ether; esters such as ethyl formate, ethyl acetate and n-butyl acetate; halogenated hydrocarbons such as dichloromethane, chloroform, carbon tetrachloride, trichlene and 1,2-dichloroethane; hydrocarbons such as n-hexane, benzene and toluene; amides such as formamide, N,N-dimethylformamide and N,N-dimethylacetamide; ketones such as acetone, methyl ethyl ketone and methyl isobutyl ketone; nitriles such as acetonitrile and propionitrile; dimethyl sulfoxide, sulfolane, hexamethylphosphoramide and water; these solvents are used as simple or mixed solvents.

Reaction temperature is normally −80 to 150° C., preferably −50 to 120° C. The amount of each of compounds (XV) and (XVI) used is normally 1 to 5 mol, preferably 1 to 3 mol, per mol of compound (XIV).

The ester of compound (XVII) is then subjected to hydrolysis, hydrogenolysis, or the like, to yield compound (XVIII).

This hydrogenolysis reaction is normally carried out in a solvent; a solvent that does not interfere with the reaction is chosen as appropriate. Such solvents include, for example, alcohols such as methanol, ethanol, propanol, isopropanol, butanol and tert-butanol; ethers such as dioxane, tetrahydrofuran, diethyl ether, tert-butyl methyl ether, diisopropyl ether and ethylene glycol-dimethyl ether; halogenated hydrocarbons such as dichloromethane, chloroform, carbon tetrachloride, trichlene and 1,2-dichloroethane; hydrocarbons such as n-hexane, benzene and toluene; amides such as formamide, N,N-dimethylformamide and N,N-dimethylacetamide; ketones such as acetone, methyl ethyl ketone and methyl isobutyl ketone; nitrites such as acetonitrile and propionitrile; dimethyl sulfoxide, sulfolane, hexamethylphosphoramide and water; these solvents are used as simple or mixed solvents.

This reaction is carried out in the presence of a base. Preferably used bases include metal hydroxides such as lithium hydroxide, potassium hydroxide, sodium hydroxide and barium hydroxide, and metal carbonates such as potassium carbonate, sodium carbonate and barium carbonate. The amount of base used is normally 1 to 30 mol, preferably 1 to 10 mol, per mol of compound (XVII). Reaction temperature is normally −30 to 150° C., preferably −10 to 120° C. Reaction time is normally 15 minutes to 48 hours, preferably 30 minutes to 24 hours.

When compound (XVIII) is produced by a hydrogenolysis reaction, the reaction is normally carried out using a catalyst. This catalyst is preferably one for catalytic reduction reaction, exemplified by platinum catalysts (e.g., platinum oxide, platinum black, platinum-carbon), palladium catalysts (e.g., palladium chloride, palladium-carbon, palladium-calcium carbonate, palladium-barium sulfate), rhodium catalysts (e.g., rhodium-carbon, rhodium-alumina) and ruthenium catalysts (e.g., ruthenium oxide, ruthenium-carbon), with greater preference given to palladium catalysts. The reaction is normally carried out in a solvent; a solvent that does not interfere with the reaction is chosen as appropriate. Such solvents include, for example, alcohols such as methanol, ethanol, propanol, isopropanol, butanol and tert-butanol; ethers such as dioxane, tetrahydrofuran, diethyl ether, tert-butyl methyl ether, diisopropyl ether and ethylene glycol-dimethyl ether; esters such as ethyl formate, ethyl acetate and n-butyl acetate; hydrocarbons such as n-hexane, benzene and toluene; amides such as formamide, N,N-dimethylformamide and N,N-dimethylacetamide; and water; these solvents are used as simple or mixed solvents.

Reaction temperature is normally −10 to 120° C., preferably 0 to 100° C. Although this reaction is normally carried out at normal pressure, it may be carried out at increased pressure in some cases. Such pressure is preferably 1 to 200 atm.

Compound (XVIII) can be decarbonized by heating to yield compound (I). This reaction is normally carried out in a solvent; a solvent that does not interfere with the reaction is chosen as appropriate. Such solvents include, for example, alcohols such as methanol, ethanol, propanol, isopropanol, butanol and tert-butanol; ethers such as dioxane, tetrahydrofuran, diethyl ether, tert-butyl methyl ether, diisopropyl ether and ethylene glycol-dimethyl ether; esters such as ethyl formate, ethyl acetate and n-butyl acetate; halogenated hydrocarbons such as dichloromethane, chloroform, carbon tetrachloride, trichlene and 1,2-dichloroethane; hydrocarbons such as n-hexane, benzene and toluene; amides such as formamide, N,N-dimethylformamide and N,N-dimethylacetamide; ketones such as acetone, methyl ethyl ketone and methyl isobutyl ketone; nitriles such as acetonitrile and propionitrile; dimethyl sulfoxide, sulfolane, hexamethylphosphoramide and water; these solvents are used as simple or mixed solvents.

Reaction temperature is normally 0 to 180° C., preferably 10 to 150° C. Reaction time is normally 5 minutes to 24 hours, preferably 10 minutes to 12 hours.

When a compound involved in each reaction described above has an amino group, a carboxyl group or a hydroxyl group as a substituent, the group may incorporate a protecting group in common use in peptide chemistry and other fields; the desired compound can be obtained by removing the protecting group as necessary after reaction.

Useful amino group-protecting groups include, for example, formyl group, $C_{1-6}$ alkylcarbonyl groups (e.g., acetyl, ethylcarbonyl), benzyl group, tert-butyloxycarbonyl group, benzyloxycarbonyl group, 9-fluorenylmethyloxycarbonyl group, allyloxycarbonyl group, phenylcarbonyl group, $C_{1-6}$ alkyloxycarbonyl groups (e.g., methoxycarbonyl, ethoxycarbonyl), $C_{7-10}$ aralkylcarbonyl groups (e.g., benzylcarbonyl), trityl group, phthaloyl group and N,N-dimethylaminomethylene group. These groups may be substituted by 1 to 3 halogen atoms (e.g., fluorine, chlorine, bromine), nitro group etc.

Useful carboxyl group-protecting groups include $C_{1-6}$ alkyl groups (e.g., methyl, ethyl, propyl, isopropyl, butyl, tert-butyl), phenyl group, silyl group, benzyl group and allyl group. These groups may be substituted for by 1 to 3 halogen atoms (e.g., fluorine, chlorine, bromine), nitro group etc.

Useful hydroxyl group-protecting groups include methoxymethyl group, allyl group, tert-butyl group, $C_{7-10}$ aralkyl groups (e.g., benzyl), formyl group, $C_{1-6}$ alkylcarbonyl groups (e.g., acetyl, ethylcarbonyl), benzoyl group, $C_{7-10}$ aralkylcarbonyl groups (e.g., benzylcarbonyl), pyranyl group, furanyl group and trialkylsilyl groups. These groups may be substituted by 1 to 3 halogen atoms (e.g., fluorine, chlorine, bromine), $C_{1-6}$ alkyl groups (e.g., methyl, ethyl, propyl, isopropyl, butyl, tert-butyl), phenyl group, $C_{7-10}$ aralkyl groups (e.g., benzyl), nitro group etc.

These protecting groups can be removed by commonly known methods or modifications thereof, including those using acids, bases, reduction, ultraviolet rays, hydrazine, phenylhydrazine, sodium N-methyldithiocarbamate, tetrabutylammonium fluoride, palladium acetate etc.

When a compound is obtained in a free form by each of the above-described reactions of the present invention, it may be converted to a salt by a conventional method; when it is obtained as a salt, it may be converted to a free form or another salt by a conventional method.

Compound (I) thus obtained can be isolated and purified from the reaction mixture by commonly known means such as extraction, concentration, neutralization, filtration, recrystallization, column chromatography and thin-layer chromatography.

A salt of compound (I) can be produced by, for example, adding one of the above-described inorganic acids or organic acids to compound (I) by a commonly known means.

Compounds (III) and (IV), used as starting compounds in method A above, can be produced by, for example, the method described in U.S. Pat. No. 4,584,385 or a method based thereon.

Compound (V), used as a starting compound in method B above, can be produced by, for example, the method described in the Journal of Medicinal Chemistry, 21, 82 (1978) or Chemistry Letters, 166 (1980) or a method based thereon; compound (VI) can be produced by, for example, the method described in the Journal of Organic Chemistry, 42, 3608 (1977) or a method based thereon; compound (VII) can be produced by the method described in the Journal of the Chemical Society, 95, 132 (1909) or a method based thereon.

In addition to the above-mentioned processes, compound (I) can also be produced by the method described in U.S. Pat. No. 4,584,385 or a method based thereon.

Although compound (I) can be produced by chemical processes as described above, it can also be produced using microorganisms. Of the compounds of formula (I), indolmycin, can be produced by, for example, the methods described in the literature [K.V. Rao, Antibiotics and Chemotherapy (Washington, D.C.), 10, 312 (1960); W.S. Marsh et al., ibid., 10, 316 (1960); Schach von Wittenau, M. et al., J. Am. Chem. Soc. 83, 4678 (1961), ibid., 85, 3425 (1963)], using as producer strains *Streptomyces griseus* subsp. *griseus* ATCC 1264 (American Type Culture Collection Catalogue of Bacteria & Bacteriophages, 18th edition, 1992) etc. Streptomyces sp. HC-21, a new strain, can also be used as a producer strain.

The microorganism used for the method of indolmycin production of the present invention is the Streptomyces sp. HC-21 strain (hereinafter also referred to as "HC-21 strain") isolated from a soil sample from Tenninkyo, Asahikawa-shi, Hokkaido, Japan.

According to the method described in the International Journal of Systematic Bacteriology, 16(3), 313–340 (1960), the EC-21 strain is characterized as follows: All findings on medium were obtained during 14 days of cultivation and observation at 28° C., unless otherwise stated.

(I) Morphological Characteristics

The aerial mycelia elongate in simple branches from well elongated and branched substrate mycelia, with gently waved or key-shaped spore chains (normally 10 to 50 spores or more) on their tips. No whirls are noted. Spores are cylindrical (1.1 to 1.2×1.4 to 1.5 μm) and have a spiny surface.

(II) Nature in Culture

Degree of growth (G), growth and color tone of aerial mycelia (AM), back face color tone (R), presence or absence and color tone of soluble pigment (SP) etc. on various media are described below. For the description of color, standard color tone symbols in parentheses are based on the Color Harmony Manual of Container Corporation of America, 4th edition, 1958.

TABLE 1

| (a) | Sucrose-nitrate-agar medium | G | Poor, light ivory (2ca) |
|---|---|---|---|
| | | AM | None |
| | | R | Light ivory (2ca) |
| | | SP | None |
| (b) | Glucose-aspara-gine-agar medium | G | Good, ivory (2ea) |
| | | AM | Good, ivory (2ea) |
| | | R | Light yellowish brown (2ia) to yellowish brown (3na) |
| | | SP | None |
| (c) | Glycerol-aspara-gine-agar medium | G | Good, yellowish brown (3ic) |
| | | AM | Good, Light yellowish gray (2gc) |
| | | R | Yellowish brown (31a) to brown (41a) |
| | | SP | None |
| (d) | Starch-inorganic salt-agar medium | G | Moderate, ivory (2ec) |
| | | AM | Moderate, light greenish gray (2cb) |
| | | R | Light yellowish brown (2ga) to light yellowish gray (2gc) |
| | | SP | None |
| (e) | Tyrosine-agar medium | G | Good, light yellowish brown (2ga) |
| | | AM | Ivory (2ea) |
| | | R | Light yellowish brown (21a) to yellowish brown (31c) |
| | | SP | None |
| (f) | Enriched agar medium | G | Moderate, light grayish reddish brown (5ic) |
| | | AM | Poor, white |

TABLE 1-continued

| | | R | Light grayish brown (4ga) to reddish brown (61a) |
|---|---|---|---|
| | | SP | None |
| (g) | Yeast extract-malt extract-agar medium | G | Good, yellowish brown (4ia) |
| | | AM | Moderate, light grayish brown (5ga) to grayish yellowish brown (4ge) |
| | | R | Yellowish brown (3ia) to reddish yellowish brown (5pa) |
| | | SP | None |
| (h) | Oatmeal-agar medium | G | Good, light grayish brown (4gc) |
| | | AM | Moderate, light reddish white (5ea) to grayish brown (5gc) |
| | | R | Bright reddish brown (6ia) to grayish brown (5gc) |
| | | SP | None |
| (i) | Peptone-yeast extract-iron-agar medium | G | Moderate, ivory (2ea), localized |
| | | AM | None |
| | | R | Light yellowish brown (2ga) to yellowish grayish brown (3ia) |
| | | SP | None |

(III) Physiological nature

| (a) | Growth temperature range | 11 to 29° C. |
|---|---|---|
| | Optimal growth temperature range | 18 to 24° C. |
| (b) | Nitrate reduction | Weakly positive |
| (c) | Gelatin liquefaction (glucose-peptone-gelatin medium) | Negative |
| (d) | Starch hydrolysis | Negative |
| (e) | Defatted milk coagulation | Negative |
| | Defatted milk peptonization | Negative |
| (f) | Melanin-like pigment formation | |
| | Tyrosine-agar medium | Negative |
| | Peptone-yeast extract-iron-agar medium | Negative |
| (g) | Carbon source assimilation (agar medium containing pridham and gottlieb) | |
| | L-arabinose | − |
| | D-xylose | − |
| | D-glucose | ++ |
| | D-fructose | + |
| | Sucrose | − |
| | Inositol | − |
| | L-rhamnose | ++ |
| | Raffinose | − |
| | D-mannitol | − |
| | Control | − |

(Note)
++: relatively good growth
+: growth noted
±: + or − indeterminable
−: no growth (IV) Cell Analysis Analysis in accordance with the method of Hasegawa et al. [Journal of General Applied Microbiology 29, 319–322 (1983)] identified the diaminopimelic acid in the hydrochloric acid hydrolyzate of cells as the LL-configuration.

Judging from the results shown above, specifically the light yellowish brown to grayish brown aerial mycelia, gently waved or key-shaped spore chains, spiny spore surfaces, diaminopimelic acid in the LL-configuration, and other findings, it is evident that this strain belongs to the genus Streptomyces; the strain was designated Streptomyces sp. HC-21.

The Streptomyces sp. HC-21 strain as such is characterized by the capability of L-rhamnose assimilation and spiny spore surfaces.

The Streptomyces sp. HC-21 strain as such has been deposited under accession number IFO-15984 at the Institute for Fermentation, Osaka (foundation), since June 12, 1996, and under accession number FERM BP-5571 at the National Institute of Bioscience and Human-Technology, Agency of Industrial Science and Technology, Ministry of International Trade and Industry of the Japan (1–3, Higashi 1-chome, Yatabe, Tsukuba City, Ibaraki Prefecture), since Jun. 25, 1996.

The bacteria of the genus Streptomyces can undergo variation, naturally or by mutagens, as a general nature of microorganisms. Even the various variants obtained by, for example, irradiation with radiations such as X rays, gamma rays and ultraviolet rays, single spore separation, treatment with various chemicals, cultivation on drug-containing media, and other means, or naturally-occurring mutants, are all usable for the method of the present invention, as long as they are capable of producing indolmycin.

Although the culture medium for the method of the present invention may be liquid or solid, as long as it contains nutrient sources usable by the strain used, a liquid medium is preferred for large-scale treatment. The medium is supplemented as appropriate with assimilable nutrient sources, digestible nitrogen sources, inorganic substances, and trace nutrients.

Carbon sources include, for example, glucose, lactose, sucrose, maltose, dextrin, starch, glycerol, mannitol, sorbitol, oils and fats (e.g., soybean oil, olive oil, rice bran oil, sesame oil, lard oil, chicken oil); nitrogen sources include, for example, meat extract, yeast extract, dry yeasts, soybean flour, corn steep liquor, peptone, cottonseed flour, blackstrap molasses, urea, ammonium salts (e.g., ammonium sulfate, ammonium chloride, ammonium nitrate, ammonium acetate) and others. Also used as appropriate are salts containing sodium, potassium, calcium, magnesium etc., metal salts such as those of iron, manganese, zinc, cobalt, nickel etc., salts of phosphoric acid, boric acid etc., and salts of organic acids such as acetic acid and propionic acid. Additionaliy, amino acids (e.g., glutamic acid, aspartic acid, alanine, lysine, valine, methionine, proline), vitamins (e.g., $B_1$, $B_2$, nicotinic acid, $B_{12}$, C), nucleic acids (e.g. purine, pyrimidine and derivatives thereof) etc. may be contained. It is of course common practice to add inorganic or organic acids, alkalis, buffers etc. for regulation of the medium's pH, and appropriate amounts of oils and fats, surfactants etc. for defoaming.

Cultivation may be achieved by standing culture, shaking culture, spinner culture, or the like. For large-scale treatment, submerged spinner culture is of course desirable.

Although culturing conditions vary depending on the condition and composition of the medium, the kind of strain, and the means of cultivation, it is normally recommended that temperature and initial pH be 15 to 26° C. and about 5 to 9, respectively. It is desirable that temperature in the middle stage of cultivation and initial pH be 20 to 25° C. and about 6 to 8, respectively. Duration of cultivation also varies depending on the above-mentioned conditions but it is recommended that cultivation be continued until the concentration of the desired bioactive substance reaches maximum. It normally takes about 1 to 10 days in the case of shaking culture or spinner culture using a liquid medium.

The resulting bioactive substance indolmycin can be extracted and purified from the culture on the basis of its chemical nature.

Because indolmycin is produced in the culture broth and cells, it can be purified by separating the culture broth and cells by filtration or centrifugation from the culture, extracting it from the resulting filtrate or centrifugal supernatant using an organic solvent, or extracting it from cells using an organic solvent, and isolating it from each extract or the combined extract.

For industrial purposes, it is advantageous to purify indolmycin from the extract obtained by adding an organic solvent such as methanol, acetone, butanol or ethyl acetate directly to the culture, with the cell separation operation omitted.

Because indolmycin is a weakly basic oil-soluble substance, its collection from the culture broth permits the use of means of separation and purification in common use for collection of related microbial metabolites. For example, methods based on solubility differences from impurity substances and chromatographies using various carriers such as activated charcoal nonionic high porous resin, silica gel, alumina and dextran gel can be used singly or in combination.

The method of isolating and collecting indolmycin from the culture is hereinafter described specifically. First, cells are removed by filtration from the culture broth; the resulting supernatant is adjusted to appropriate pH; a solvent such as ethyl acetate is added, followed by vigorous stirring, to yield an ethyl acetate layer. The organic layer obtained is sequentially washed with alkali, acid and water, after which it is concentrated; the resulting concentrate is subjected to silica gel column chromatography. Useful developing solvents include, for example, chloroform-methanol or hexane-acetone mixed solvents. After the effective fractions are combined and concentrated, the concentrate is subjected to Sephadex LH-20 chromatography. Useful developing solvents are methanol and mixed solvents such as hexane-toluene-methanol and hexane-methylene chloride-methanol. After concentration, the eluate containing the effective fractions is purified by preparative high performance liquid chromatography. The column packing used here is ODS-SH343 S-15 (produced by Yamamura Kagaku Kenkyujo); the solvent system used is a combination of 0.02 M phosphate buffer (pH 6.3) and 26% $CH_3CN$.

BEST MODE FOR CARRYING OUT THE INVENTION

The present invention is hereinafter described in more detail by means of, but not limited to, the following working examples, experimental examples and preparation example. In the description below, "room temperature" means about 15 to 30° C.

EXAMPLES

Example 1

A platinum loopful of Streptomyces sp. HC-21 strain, previously sufficiently grown on a slant medium consisting of yeast extract-maltose extract-agar, was inoculated to a sterile 2 l Sakaguchi flask containing 500 ml of a seed medium of pH 7.0 consisting of 2% glucose, 3% soluble starch, 1% corn steep liquor, 1% fresh soybean flour, 0.5% polypeptone, 0.3% sodium chloride and 0.5% precipitating calcium carbonate, and cultured at 24° C. on a reciprocal shaker for 2 days. To this 500 ml culture broth was injected 120 l of a principal medium of pH 7.0 consisting of 2.0% glucose, 3.0% soluble starch, 1.0% defatted soybean flour, 0.3% corn steep liquor, 0.1% yeast extract, 0.5% polypeptone, 0.2% oatmeal agar, 0.3% sodium chloride, 0.5% precipitating calcium carbonate, 0.05% ACTCOL 31-56 (produced by Takeda Chemical Industries, Ltd., Japan) and 0.05% silicone, followed by transplantation to a sterile 200 l fermentation jar and 90 hours of cultivation under conditions of 24° C. temperature, 1.1 $kg/cm^2$ internal pressure, 120 l/min aeration rate and 120 rpm stirring rate.

The 120 l of the culture broth thus obtained was filtered using Hyflo Super Cel to yield 110 l of a filtrate. This filtrate was adjusted to pH 3.0 with dilute sulfuric acid; an equal amount of ethyl acetate was added, followed by vigorous stirring, to yield 80 l of an ethyl acetate layer. This ethyl acetate layer was washed with 30 l of a 2% NaHCO$_3$ solution, then with 30 l of a 0.02 N.HCl solution, and thoroughly washed with water, after which it was concentrated under reduced pressure to yield about 30 g of a concentrate. This concentrate was passed through a silica gel column (0.8 l) to adsorb the active ingredient, followed by sequential elution with 4 l of hexane-acetone (80:20), 4 l of hexane-acetone (50:50) and 4 l of hexane-acetone (20:80). The effective fractions were combined and concentrated under reduced pressure to yield 1.53 g of a concentrate. This concentrate was dissolved in methanol; the resulting solution was passed through a column (2 l) of Sephadex LH-20 (produced by Pharmacia, Sweden), thoroughly washed previously; the effective eluted fractions from 1.3 l to 1.7 l were combined and concentrated under reduced pressure to yield 490 mg of a powder. This powder was further developed (20 ml/min, 20 ml fractions) with a solvent system of 0.02 M phosphate buffer (pH 6.3) and 26% CH$_3$CN, using preparative liquid chromatography (Hitachi model L-6250, detector L-4000, YMC-Pack, ODS SH343 S-15 120 A, 214 nm), to yield effective fractions (fraction Nos. 30 through 39). After the CH$_3$CN was removed, the effective fractions were washed with water and again extracted with ethyl acetate; the ethyl acetate layer was concentrated under reduced pressure to yield 315 mg of crystalline indolmycin.

Elemental analysis (for $C_{14}H_{15}N_3O_2$): Calculated: C, 65.35; H, 5.88; N, 16.33; Found : C, 65.14; H, 5.87; N, 16.07;

The physicochemical properties also agreed well with those of indolmycin.

Example 2

(5S)-2-(N-Benzyloxycarbonyl-N-methyl)amino-5[(1R)-1-(indol-3-yl)ethyl]-2-oxazolin-4-one A solution of indolmycin (100 mg) in tetrahydrofuran (5 ml) was cooled to −30° C. To this cooled solution, triethylamine (0.217 ml) and carbobenzoxychloride (0.167 ml) was subsequently added dropwise at −30° C. The whole was allowed to warm up to 0° C. and was stirred for 80 minutes. Ethyl acetate was added to the reaction mixture. The mixture was washed with water, saturated aqueous sodium hydrogen carbonate solution and brine respectively and then the ethyl acetate solution was dried over MgSO$_4$. Removal of the organic solvent gave a residue, which was recrystalized with isopropylether to afford the titled compound (115 mg, 75.5%). m.p. 136–138° C.

IR (KBr) cm$^{-1}$: 3299, 1748. $^1$H-NMR (CDCl$_3$) δ: 1.39 (3H,d,J=7.2 Hz), 3.34(3H,s), 3.81–3.93(1H,m), 5.10(1H,d, J=2.8 Hz), 5.31(2H,s), 6.97–7.40(8H,m), 7.62(1H,d,J=7.4 Hz), 7.95(1H,bs).

Example 3

Following the same procedure as described in the Example 2, the following compounds were prepared.

(5S)-2-(N-ethoxycarbonyl-N-methyl)amino-5[(1R)-1-(indol-3-yl)ethyl]-2-oxazolin-4-one, IR (KBr) cm$^{-1}$: 3293, 1769, 1738. $^1$H-NMR (CDCl$_3$) δ: 1.34(3H,d,J=7.0 Hz), 1.41(3H,t,J=7.2 Hz), 3.32(3H,s), 3.88 (1H,m), 4.35(2H,q,J=7.2 Hz), 5.10(1H,d,J=2.6 Hz), 7.07–7.26(3H,m), 7.36(1H,d,J=8.2 Hz), 7.67(1H,d,J=8.2 Hz), 8.15(1H,bs).

(5S)-5-[(1R)-1-(indol-3-yl)ethyl]-2-(N-isopropoxycarbonyl-N-methyl)amino-2-oxazolin-4-one, IR (KBr) cm$^{-1}$: 3272, 1732. $^1$H-NMR (CDCl$_3$) δ: 1.36 (6H,d,J=6.4 Hz), 1.43(3H,d,J=7.4 Hz), 3.31(3H,s), 3.91(1H, m), 5.08(1H,m), 5.12(1H,d,J=2.6 Hz), 7.07–7.35(3H,m), 7.37(1H,d,J=8.0 Hz), 7.67(1H,d,J=7.8 Hz), 8.17(1H,bs).

(5S)-2-[N-(2-ethylhexyloxycarbonyl)-N-methyl]amino-5-[(1R)-1-(indol-3-yl)ethyl]-2-oxazolin-4-one, IR (KBr) cm$^{-1}$: 3298, 1769, 1742. $^1$H-NMR (CDCl$_3$) δ: 0.90(6H,t,J=7.6 Hz), 1.26–1.60(9H,m), 3.29(3H,s), 3.90 (1H,m), 4.19(2H,d,J=5.8 Hz), 5.12(1H,d,J=3.0 Hz), 7.06–7.38(4H,m), 7.66(1H,d,J=7.6 Hz), 8.14(1H,bs).

(5S)-2-[N-(4-acetoxybenzyloxycarbonyl)-N-methyl] amino-5-[(1R)-1-(indol-3-yl)ethyl]-2-oxazolin-4-one, IR (KBr) cm$^{-1}$: 3333, 1746. $^1$H-NMR (CDCl$_3$) δ: 1.24 (3H,d,J=7.4 Hz), 2.41(3H,s), 3.50(3H,s), 3.80(1H,m), 5.09 (1H,d,J=2.8 Hz), 5.30(2H,s), 6.52(1H,d,J=2.2 Hz), 7.03–7.46(7H,m), 7.57(1H,d,J=7.6 Hz), 8.56(1H,bs).

(5S)-5-[(1R)-1-(indol-3-yl)ethyl]-2-[N-(4-nitrobenzyloxycarbonyl)-N-methyl]amino-2-oxazolin-4-one, IR (KBr) cm$^{-1}$: 3299, 1773, 1746. $^1$H-NMR (CDCl$_3$) δ: 1.44(3H,d,J=7.2 Hz), 3.35(3H,s), 3.90(1H,m), 5.15(1H,d,J= 2.6 Hz), 5.37(2H,s), 7.03–7.24(3H,m), 7.37(1H,d,J=8.2 Hz), 7.47(2H,d,J=8.8 Hz), 7.64(1H,d,J=8.4 Hz), 8.10(1H,bs), 8.14(2H,d,J=8.8 Hz).

(5S)-5-[(1R)-1-(indol-3-yl)ethyl]-2-(N-methyl-N-phenoxycarbonyl)amino-2-oxazolin-4-one, IR (KBr) cm$^{-1}$: 3281, 1779, 1746. $^1$H-NMR (CDCl$_3$) δ: 1.45(3H,d,J=7.2 Hz), 3.47(3H,s), 3.91(1H,m), 5.15(1H,d,J= 3.0 Hz), 7.03–7.49(9H,m), 7.67(1H,d,J=7.4 Hz), 8.05(1H, bs).

Example 4

(5S)-5-[(1R)-1-(Indol-3-yl)ethyl]-2-[N-(N-(4-methoxyphenyl)carbamoyl)-N-methyl]amino-2-oxazolin-4-one To a mixture of indolmycin (150 mg) and dichloromethane (3 ml) was added 4-methoxyphenylisocyanate (261 mg) under ice cooling. After the mixture was sitrred for 2 hours at room temperature, the solvent was distilled off to give a residue. After isopropylether was added to the residue, the titled compound was obtained as a crystal (213 mg, 89.9%).

IR (KBr) cm$^{-1}$: 3382, 1717. $^1$H-NMR (CDCl$_3$) δ: 1.48 (3H,d,J=7.0 Hz), 3.34(3H,s), 3.78(3H,s), 3.95(1H,m), 5.08 (1H,d,J=3.0 Hz), 6.83(2H,d,J=9.2 Hz), 7.11–7.40(6H,m), 7.67(1H,d,J=8.4 Hz), 8.21(1H,bs), 11.21(1H,bs).

Example 5

Following the same procedure as described in the Example 4, the following compounds were prepared.

(5S)-2-[N-(N-(4-chlorophenyl)carbamoyl)-N-methyl] amino-5-[(1R)-2-(indol-3-yl)ethyl]-2-oxazolin-4-one, IR (KBr) cm$^{-1}$: 3372, 1713. $^1$H-NMR (CDCl$_3$) δ: 1.49 (3H,d,J=7.4 Hz), 3.34(3H,s), 3.97(1H,m), 5.09(1H,d,J=3.2 Hz), 7.15–7.47(8H,m), 7.67(1H,d,J=7.4 Hz), 8.17(1H,bs), 11.48(1H,bs).

(5S)-5-[(1R)-1-(indol-3-yl)ethyl]-2-[N-(N-(2-phenylethyl)carbamoyl)-N-methyl]amino-2-oxazolin-4-one, IR (KBr) cm$^{-1}$: 3243, 1713. $^1$H-NMR (CDCl$_3$) δ: 1.44 (3H,d,J=7.4 Hz), 2.82(2H,t,J=8.0 Hz), 3.28(3H,s), 3.47(2H, m), 3.91(1H,m), 5.02(1H,d,J=3.0 Hz), 7.11–7.40(9H,m), 7.65(1H,d,J=7.8 Hz), 8.15(1H,bs), 9.33(1H,bs).

(5S)-2-[N-(N-(2,4-dimethoxyphenyl)carbamoyl)-N-methyl]amino-5-[(1R)-1-(indol-3-yl)ethyl]-2-oxazolin-4-one, IR (KBr) cm$^{-1}$: 3397, 1711. $^1$H-NMR (CDCl$_3$) δ: 1.45 (3H,d,J=7.2 Hz), 3.37(3H,s), 3.79(3H,s), 3.89(3H,s), 3.92 (1H,m), 5.07(1H,d,J=2.8 Hz), 6.42–6.47(2H,m), 7.14–7.26 (3H,m), 7.39(1H,d,J=7.4 Hz), 7.69(1H,d,J=6.8 Hz), 7.90 (1H,d,J=9.2 Hz), 8.14(1H,bs), 11.45(1H,bs).

(5S)-2-[N-(N-(7-ethoxycarbonylheptyl)carbamoyl)-N-methyl]amino-5-[(1R)-1-(indol-3-yl)ethyl]-2-oxazolin-4-one, IR (KBr) cm$^{-1}$: 3235, 1716. $^1$H-NMR (CDCl$_3$) δ: 1.17–1.32(9H,m), 1.45(3H,d,J=7.4 Hz), 1.50–1.72(4H,m), 2.30(2H,t,J=7.4 Hz), 3.20(2H,m), 3.28(3H,s), 4.13(2H,q,J=7.0 Hz), 5.02(1H,d,J=3.0 Hz), 7.10–7.25(3H,m), 7.38(1H, d,J=7.6 Hz), 7.65(1H,d,J=7.8 Hz), 8.34(1H,bs), 9.18(1H,bs).

Example 6
(5S)-5-[(1R)-1-(Indol-3-yl)ethyl]-2-(N-(4-trifluromethylbenzoyl)-N-methyl]amino-2-oxazolin-4-one To a well stirred mixture of indolmycin (150 mg), triethylamine (325 μl), 4-dimethylaminopyridine (39.8 mg), and tetrahydrofuran (10 ml) under the ice cooling, 4-trifluoromethylbenzoylchloride (260 μl) was added. The mixture was stirred for 30 minutes at 0° C. and ethyl acetate was added. The whole was washed with water, saturated aqueous sodium hydrogen carbonate solution and brine respectively and then the ethyl acetate solution was dried over MgSO$_4$. Removal of the organic solvent gave a residue, which was subjected to silica-gel chromatography. Elution with hexane-acetone (4:1) provided the titled compound (176 mg, 70.4%). m.p. 146–148° C.

IR (KBr) cm$^{-1}$: 3390, 1749, 1714. $^1$H-NMR (CDCl$_3$) δ: 1.42(3H,d,J=7.2 Hz), 3.41(3H,s), 3.77–3.89(1H,m), 4.92 (1H,d,J=2.8 Hz), 6.64(1H,d,J=2.0 Hz), 7.13–7.56(8H,m), 8.03(1H,bs).

Example 7
Following the same procedure as described in the Example 6, the following compounds were prepared.

(5S)-5-[(1R)-1-(indol-3-yl)ethyl]-2-(N-(2-trifluoromethylbenzoyl)-N-methyl]amino-2-oxazolin-4-one, IR (KBr) cm$^{-1}$: 3287, 1748, 1717. $^1$H-NMR (CDCl$_3$) δ: 1.23(3H,d,J=7.2 Hz), 3.51(3H,s), 3.68(1H,m), 4.87(1H,d,J=2.8 Hz), 6.60(1H,d,J=1.8 Hz), 7.08–7.26(3H,m), 7.36–7.61 (5H,m), 8.02(1H,bs).

(5S)-5-[(1R)-1-(indol-3-yl)ethyl]-2-[N-(3-trifluoromethylbenzoyl)-N-methyl]amino-2-oxazolin-4-one, IR (KBr) cm$^{-1}$: 3335, 1715. $^1$H-NMR (CDCl$_3$) δ: 1.37 (3H,d,J=7.2 Hz), 3.41(3H,s), 3.78(1H,m), 4.91(1H,d,J=3.4 Hz), 6.62(1H,d,J=2.2 Hz), 7.11–7.40(5H,m), 7.51(1H,d,J=8.0 Hz), 7.73(1H,d,J=7.4 Hz), 7.78(1H,s), 8.00(1H,bs).

(5S)-2-[N-(4-fluorobenzoyl)-N-methyl]amino-5-[(1R)-1-(indol-3-yl)ethyl]-2-oxazolin-4-one, IR (KBr) cm$^{-1}$: 3300, 1741, 1707. $^1$H-NMR (CDCl$_3$) δ: 1.44(3H,d,J=7.4 Hz), 3.38(3H,s), 3.76–3.90(1H,m), 4.93 (1H,d,J=3.0 Hz), 6.76(1H,d,J=2.4 Hz), 6.92–7.00(2H,m), 7.09–7.27(4H,m), 7.40(1H,d,J=8.0 Hz), 7.56(1H,d,J=7.2 Hz), 8.13(1H,bs).

(5S)-2-[N-(4-chlorobenzoyl)-N-methyl]amino-5-[(1R)-1-(indol-3-yl)ethyl]-2-oxazolin-4-one, IR (KBr) cm$^{-1}$: 3296, 1746, 1705. $^1$H-NMR (CDCl$_3$) δ: 1.42(3H,d,J=7.4 Hz), 3.38(3H,s), 3.75–3.86(1H,m), 4.93 (1H,d,J=3.0 Hz), 6.70(1H,d,J=2.6 Hz), 7.09–7.28(6H,m), 7.40(1H,d,J=7.8 Hz), 7.55(1H,d,J=8.0 Hz), 8.09(1H,bs).

(5S)-5-[(1R)-1-(indol-3-yl)ethyl]-2-[N-(4-methylbenzoyl)-N-methyl]amino-2-oxazolin-4-one, IR (KBr) cm$^{-1}$: 3300, 1744, 1703. $^1$H-NMR (CDCl$_3$) δ: 1.36(3H,d,J=7.4 Hz), 2.39(3H,s), 3.38(3H,s), 3.71–3.83(1H, m), 4.89(1H,d,J=3.0 Hz), 6.59(1H,d,J=2.2 Hz), 7.06–7.38 (7H,m), 7.50(1H,d,J=8.4 Hz), 8.00(1H,bs).

(5s)-5-[(1R)-1-(indol-3-yl)ethyl]-2-[N-(4-methoxybenzoyl)-N-methyl]amino-2-oxazolin-4-one, IR (KBr) cm$^{-1}$: 3299, 1744, 1701. $^1$H-NMR (CDCl$_3$) δ: 1.39(3H,d,J=7.4 Hz), 3.38(3H,s), 3.82(3H,s), 4.91(1H,d,J=2.8 Hz), 6.67(1H,d,J=2.2 Hz), 6.81(2H,d,J=8.8 Hz), 7.06–7.26(3H,m), 7.36(2H,d,J=8.8 Hz), 7.52(1H,d,J=7.4 Hz), 8.01(1H,bs).

(5S)-2-(N-cinnamoyl-N-methyl)amino-5-[(1R)-1-(indol-3-yl)ethyl]-2-oxazolin-4-one, IR (KBr) cm$^{-1}$: 3395, 1753, 1682, 1615. $^1$H-NMR (CDCl$_3$) δ: 1.46(3H,d,J=7.2 Hz), 3.38(3H,s), 3.88–3.99(1H, m), 5.14(1H,d,J=3.0 Hz), 7.06–7.82(12H,m), 7.96(1H,bs).

(5S)-5-[(1R)-1-(indol-3-yl)ethyl]-2-(N-methyl-N-nicotinoyl)amino-2-oxazolin-4-one, IR (KBr) cm$^{-1}$: 3277, 1748, 1703. $^1$H-NMR (CDCl$_3$) δ: 1.48(3H,d,J=7.4 Hz), 3.37(3H,s), 3.79–3.92(1H,m), 4.95 (1H,d,J=3.4 Hz), 6.80(1H,d,J=2.2 Hz), 7.09–7.58(6H,m), 8.12(1H,d,J=2.2 Hz), 8.40(1H,bs), 8.63(1H,dd,J=1.8&4.8 Hz).

(5S)-5-[(1R)-1-(indol-3-yl)ethyl]-2-(N-methyl-N-phenylacetyl)amino-2-oxazolin-4-one, IR (KBr) cm$^{-1}$: 3300, 1724. $^1$H-NMR (CDCl$_3$) δ: 1.45 (3H,d,J=7.0 Hz), 3.25(3H,s), 3.85–3.99(1H,m), 4.10(1H,d,J=16.6 Hz), 4.25(1H,d,J=16.6 Hz), 5.05(1H,d,J=2.8 Hz), 6.98–7.39(9H,m), 7.63(1H,d,J=8.6 Hz), 8.18(1H,bs).

(5S)-5-[(1R)-1-(indol-3-yl)ethyl]-2-(N-methyl-N-(2-thiophene)carbonyl]amino-2-oxazolin-4-one, IR (KBr) cm$^{-1}$: 3289, 1739, 1672. $^1$H-NMR (CDCl$_3$) δ: 1.48(3H,d,J=7.4 Hz), 3.37(3H,s), 3.81–3.90(1H,m), 4.99 (1H,d,J=3.0 Hz), 6.87–7.66(8H,m), 8.08(1H,bs).

(5S)-5-[(1R)-1-(indol-3-yl)ethyl]-2-(N-methyl-N-(2-thienyl)acetyl]amino-2-oxazolin-4-one, IR (KBr) cm$^{-1}$: 3298, 1726. $^1$H-NMR (CDCl$_3$) δ: 1.49 (3H,d,J=7.2 Hz), 3.26(3H,s), 3.88–3.99(1H,m), 4.34(1H,d,J=17.6 Hz), 4.51(1H,d,J=17.6 Hz), 5.09(1H,d,J=3.2 Hz), 6.80–7.22(6H,m), 7.38(1H,d,J=7.4 Hz), 7.64(1H,d,J=7.6 Hz), 8.17(1H,bs).

(5S)-2-(N-heptanoyl-N-methyl)amino-5-[(1R)-1-(indol-3-yl)ethyl]-2-oxazolin-4-one, IR (KBr) cm$^{-1}$: 3275, 1732. $^1$H-NMR (CDCl$_3$) δ: 0.88 (3H,t,J=6.2 Hz), 1.18–1.33(6H,m), 1.47(3H,d,J=7.2 Hz), 1.55–1.63(2H,m), 2.84(2H,q,J=5.4 Hz), 3.26(3H,s), 3.87–3.99(1H,m), 5.07(1H,d,J=3.0 Hz), 7.09–7.25(3H,m), 7.38(1H,d,J=7.4 Hz), 7.65(1H,d,J=7.4 Hz), 8.14(1H,bs).

(5S)-2-(N-cyclohexylcarbonyl-N-methyl)amino-5-[(1R)-1-(indol-3-yl)ethyl]-2-oxazolin-4-one, IR (KBr) cm$^{-1}$: 3320, 1717. $^1$H-NMR (CDCl$_3$) δ: 1.11–1.39(6H,m), 1.50(3H,d,J=7.2 Hz), 1.53–1.83(4H,m), 3.23(3H,s), 3.46–3.60(1H,m), 3.85–3.99(1H,m), 5.06(1H,d, J=3.0 Hz), 7.09–7.24(3H,m), 7.37(1H,d,J=7.0 Hz), 7.65(1H, d,J=7.6 Hz), 8.11(1H,bs).

(5S)-5-[(1R)-1-(indol-3-yl)ethyl]-2-(N-methyl-N-pivaloyl)amino-2-oxazolin-4-one, IR (KBr) cm$^{-1}$: 3287, 1736, 1624. $^1$H-NMR (CDCl$_3$) δ: 1.12(9H,s), 1.47(3H,d,J=7.4 Hz), 3.16(3H,s), 3.90(1H,m), 5.02(1H,d,J=3.0 Hz), 7.08–7.26(3H,m), 7.36(1H,d,J=7.2 Hz), 7.64(1H,d,J=7.2 Hz), 8.27(1H,bs).

(5S)-2-(N-acetyl-N-methyl)amino-5-[(1R)-1-(indol-3-yl) ethyl]-2-oxazolin-4-one,

IR (KBr) cm$^{-1}$: 3378, 1750, 1722. $^1$H-NMR (CDCl$_3$) δ: 1.47(3H,d,J=7.0 Hz), 2.48(3H,s), 3.25(3H,s), 3.94(1H,m), 5.08(1H,d,J=3.4 Hz), 7.09–7.22(3H,m), 7.38(1H,d,J=7.4 Hz), 7.65(1H,d,J=8.0 Hz), 8.15(1H,bs).

(5S)-5-[(1R)-1-(indol-3-yl)ethyl]-2-(N-isobutyl-N-methyl)amino-2-oxazolin-4-one, IR (KBr) cm$^{-1}$: 3300, 1736, 1725. $^1$H-NMR (CDCl$_3$) δ: 0.86(3H,d,J=7.0 Hz), 1.07(3H,d,J=6.8 Hz), 1.50(3H,d,J=7.4 Hz), 3.24(3H,s), 3.86(1H,m), 3.94(1H,m), 5.05(1H,d,J=3.0 Hz), 7.09–7.23(3H,m), 7.36(1H,d,J=7.4 Hz), 7.64(1H,d,J=7.4 Hz), 8.13(1H,bs).

(5S)-5-[(1R)-1-(indol-3-yl)ethyl]-2-(N-methyl-N-propionyl)amino-2-oxazolin-4-one, IR (KBr) cm$^{-1}$: 3381, 1736, 1723. $^1$H-NMR (CDCl$_3$) δ: 1.05(3H,t,J=7.2 Hz), 1.47(3H,d,J=7.2 Hz), 2.87(2H,m), 3.26(3H,s), 3.88–4.00(1H,m), 5.06(1H,d,J=3.0 Hz), 7.09–7.25(3H,m), 7.38(1H,d,J=7.4 Hz), 7.64(1H,d,J=7.4 Hz), 8.13(1H,bs).

(5S)-5-[(1R)-1-(indol-3-yl)ethyl]-2-(N-methyl-N-palmitoyl)amino-2-oxazolin-4-one, IR (KBr) cm$^{-1}$: 3370, 1726. $^1$H-NMR (CDCl$_3$) δ: 0.88 (3H,t,J=6.6 Hz), 1.16–1.19(26H,m), 1.46(3H,d,J=7.2 Hz), 2.82(2H,m), 3.25(3H,s), 3.91(1H,m), 5.06(1H,d,J=3.2 Hz), 7.09–7.21(3H,m), 7.37(1H,d,J=7.4 Hz), 7.64(1H,d,J=7.8 Hz), 8.12(1H,bs).

Example 8

(5S)-2-[N-(2-Benzyloxybenzoyl)-N-methyl]amino-5-[(1R)-1-(indol-3-yl)ethyl]-2-oxazolin-4-one To a well stirred mixture of indolmycin (400 mg), triethylamine (868 μl) and 4-dimethylaminopyridine (106 mg) in tetrahydrofuran (20 ml) was added 2-benzyloxybenzoylchloride (1.15 g) under the ice cooling. The mixture was stirred for 40 minutes at 0° C. and ethyl acetate was added. The whole was washed with water, saturated aqueous sodium hydrogen carbonate solution and brine respectively and then the ethyl acetate solution was dried over MgSO$_4$. Removal of the organic solvent gave a residue, which was subjected to silica-gel chromatography. Elution with hexane-acetone (5:1) provided the titled compound (534 mg, 73.3%).

IR (KBr) cm$^{-1}$: 3303, 1744, 1701. $^1$H-NMR (CDCl$_3$) δ: 1.15(3H,d,J=7.0 Hz), 3.40(3H,s), 3.65(1H,m), 4.68(1H,d,J=2.6 Hz), 4.97(2H,s), 6.28(1H,d,J=2.6 Hz), 6.89(1H,d,J=8.4 Hz), 7.04–7.50(12H,m), 7.85(1H,bs).

Example 9

(5S)-2-[N-(2-Hydroxybenzoyl)-N-methyl]amino-5-[(1R)-1-(indol-3-yl)ethyl]-2-oxazolin-4-one To a solution of (5S)-2-[N-(2-benzyloxybenzoyl)-N-methyl]amino-5-[(1R)-1-(indol-3-yl)ethyl]-2-oxazolin-4-one (420 mg) in tetrahydrofuran (10 ml) was added 10% palladium-carbon (300 mg). The whole was subjected to hydrogenation and then filtered to remove the catalyst. The filtrate was distilled off to give a residue, which was treated with ether to provide the titled compound (104 mg, 30.7%) as a crystal.

IR (KBr) cm$^{-1}$: 3430, 3250, 1752, 1649. $^1$H-NMR (DMSO-d$_6$) δ: 1.38(3H,d,J=7.4 Hz), 2.59(3H,s), 3.56(1H,m), 4.77(1H,d,J=3.0 Hz), 6.89–7.84(9H,m), 10.62(1H,bs), 10.87(1H,bs).

Example 10

(5S)-5-[(1R)-1-(Indol-3-yl)ethyl]-2-[N-(1-piperidinocarbonyl)-N-methyl]amino-2-oxazolin-4-one To a mixture of indolmycin (150 mg) and triethylamine (324 μl) in tetrahydrofuran (7.0 ml) was added 4-nitrophenyl chloroformate (353 mg) at 0° C. The mixture was stirred for 15 minutes at 0° C. and then piperidine (173 μl) was added. After the whole was further stirred for 8 minutes at 0° C., ethyl acetate was added. The whole was washed with water, saturated aqueous sodium hydrogen carbonate solution and brine respectively and then the ethyl acetate solution was dried over MgSO$_4$. Removal of the organic solvent gave a residue, which was subjected to silica-gel chromatography. Elution with hexane-acetone (3:1) provided the titled compound (154 mg, 71.6%).

IR (KBr) cm$^{-1}$: 3279, 1698. $^1$H-NMR (CDCl$_3$) δ: 1.20–1.75(9H,m), 3.09–3.35(5H,m), 3.40–3.70(2H,m), 3.88 (1H,m), 4.99(1H,d,J=2.6 Hz), 7.10–7.19(3H,m), 7.34(1H,d, J=7.4 Hz), 7.67(1H,d,J=8.4 Hz), 8.17(1H,bs).

Example 11

(5S)-2-[N-(N-Benzyloxycarbonyl-L-alanyl)-N-methyl] amino-5-[(1R)-1-(indol-3-yl)ethyl]-2-oxazolin-4-one To a mixture of N-benzyloxycarbonyl-L-alanine (893 mg) and triethylamine (1.11 ml) in tetrahydrofuran (10 ml) was added ethyl chloroformate (381 μl) at −15° C. The mixture was stirred for 5 minutes at −15° C. and then indolmycin (257 mg) was added. After the whole was further stirred for 8 minutes at 0° C., ethyl acetate was added. The whole was warmed up to room temperature and stirred for 40 minutes. Ethyl acetate was added to the mixture. The mixture was washed with water, saturated aqueous sodium hydrogen carbonate solution and brine respectively and then the ethyl acetate solution was dried over MgSO$_4$. Removal of the organic solvent gave a residue, which was subjected to silica-gel chromatography. Elution with hexane-acetone (4:1) provided the titled compound (387 mg, 83.3%).

IR (KBr) cm$^{-1}$: 3233, 1715. $^1$H-NMR (CDCl$_3$) δ: 1.26–1.60(6H,m), 2.20(3H,s), 4.14(1H,m), 5.05–5.24(4H, m), 6.69(1H,s), 7.11–7.36(9H,m), 7.64(1H,bs), 8.11(1H,s).

Example 12

Following the same procedure as described in the Example 11, the following compounds were prepared.

(5S)-2-[N-(N-benzyloxycarbonylglycyl)-N-methyl] amino-5-[(1R)-1-(indol-3-yl)ethyl]-2-oxazolin-4-one, IR (KBr) cm$^{-1}$: 3277, 1717. $^1$H-NMR (CDCl$_3$) δ: 1.55 (3H,d,J=7.8 Hz), 2.44(3H,s), 3.91(1H,d,J=15.8 Hz), 4.01 (1H,d,J=15.8 Hz), 4.53(1H,m), 5.11(2H,s), 5.20(1H,m), 6.61(1H,s), 7.15–7.34(9H,m), 7.62(1H,m), 8.13(1H,bs).

(5S)-2-[N-(N-benzyloxycarbonyl-L-leucyl)-N-methyl] amino-5-[(1R)-1-(indol-3-yl)ethyl]-2-oxazolin-4-one, IR (KBr) cm$^{-1}$: 3300, 1717. $^1$H-NMR (CDCl$_3$) δ: 0.75 (6H,m), 1.44–1.81(6H,m), 2.19(3H,s), 4.14(1H,m), 5.01–5.27(4H,m), 6.67(1H,s), 7.07–7.22(4H,m), 7.33(5H, m), 7.60(1H,m), 8.11(1H,bs).

(5S)-2-[N-(N-benzyloxycarbonyl-L-phenylalanyl)-N-methyl]amino-5-[(1R)-1-(indol-3-yl)ethyl]-2-oxazolin-4-one, IR (KBr) cm$^{-1}$: 3375, 1719. $^1$H-NMR (CDCl$_3$) δ: 1.31 (1H,d,J=7.4 Hz), 1.45(2H,d,J=7.2 Hz), 3.13(3H,s), 3.50(2H, m), 4.42(1H,m), 4.52(1H,m), 5.08–5.44(3H,m), 6.70–7.60 (15H,m), 8.04(1H,s).

(5S)-2-[N-(N-benzyloxycarbonyl-L-prolyl)-N-methyl] amino-5-[(1R)-1-(indol-3-yl)ethyl]-2-oxazolin-4-one, IR (KBr) cm$^{-1}$: 3324, 1701. $^1$H-NMR (CDCl$_3$) δ: 1.28 (1.5H,d,J=7.2 Hz), 1.42(1.5H,d,J=5.2 Hz), 1.90(3H,m), 2.39 (1H,m), 3.11(1.5H,s), 3.30(1.5H,s), 3.51–3.66(2H,m), 3.89 (1H,m), 4.89–5.21(3H,m), 5.40–5.52(1H,m), 7.01–7.36(9H, m), 8.01(0.5H,bs), 8.19(0.5H,bs).

(5S)-2-[N-(N-benzyloxycarbonyl-L-γ-benzylglutaminyl)-N-methyl]amino-5-[(1R)-1-(indol-3-yl)ethyl]-2-oxazolin-4-one, IR (KBr) cm$^{-1}$: 3354, 1719. $^1$H-NMR (CDCl$_3$) δ: 1.56 (3H,m), 1.75(2H,m), 2.17(3H,s), 2.40(2H,m), 3.73(1H,m), 4.25(1H,m), 5.00–5.22(5H,m), 7.11–7.34(14H,m), 7.64(1H, m), 8.10(1H,bs)

Example 13

(5S)-2-[N-(N-(L-Alanyl)-N-methyl]amino-5-[(1R)-1-(indol-3-yl)ethyl]-2-oxazolin-4-one To a solution of (5S)-2-[N-(N-benzyloxycarbonyl-L-alanyl)-N-methyl]amino-5-[(1R)-1-(indol-3-yl)ethyl]-2-oxazolin-4-one (387 mg) in tetrahydrofuran (4 ml) was added 10% palladium-carbon (100 mg). The whole was subjected to hydrogenation and then filtered to remove the catalyst. The filtrate was distilled off to give a residue, which was treated with ether to provide the titled compound (141 mg, 51.6%) as a crystal.

IR (KBr) cm$^{-1}$: 3372, 3287, 1736, 1633. $^1$H-NMR (CDCl$_3$) δ: 1.26(3H,d,J=7.0 Hz), 1.52(3H,d,J=7.0 Hz), 3.13 (3H,s), 3.80(1H,m), 4.22(1H,q,J=7.0 Hz), 4.53(1H,bs), 7.07–7.22(2H,m), 7.36(1H,d,J=7.2 Hz), 7.72(1H,d,J=7.0 Hz), 8.02(1H,bs), 9.09(1H,bs).

Example 14

Following the same procedure as described in Example 13, the following compounds were prepared.

(5S)-2-(N-glycyl-N-methyl)amino-5-[(1R)-1-(indol-3-yl)ethyl]-2-oxazolin-4-one,

IR (KBr) cm$^{-1}$: 3333, 1748, 1630. $^1$H-NMR (CDCl$_3$) δ: 1.27(3H,d,J=7.2 Hz), 3.14(3H,s), 3.80(1H,m), 4.15(2H,s), 4.54(1H,d,J=2.8 Hz), 7.08–7.22(2H,m), 7.36(1H,d,J=7.2 Hz), 7.72(1H,d,J=7.4 Hz), 8.03(1H,bs), 9.02(1H,bs).

(5S)-5-[(1R)-1-(indol-3-yl)ethyl]-2-(N-L-leucyl-N-methyl)amino-2-oxazolin-4-one, IR (KBr) cm$^{-1}$: 3368, 1759, 1644. $^1$H-NMR (CDCl$_3$) δ: 1.00(6H,d,J=4.8 Hz), 1.27(3H,d,J=7.0 Hz), 1.63(1H,m), 1.77(2H,m), 3.13(3H,s), 3.80(1H,m), 4.18(1H,dd,J=3.8&9.2 Hz), 4.52(1H,d,J=2.6 Hz), 7.07–7.21(2H,m), 7.36(1H,d,J= 7.4 Hz), 7.72(1H,d,J=7.4 Hz), 8.02(1H,bs), 9.18(1H,bs).

(5S)-5-[(1R)-1-(indol-3-yl)ethyl]-2-(N-L-phenylalanyl-N-methyl)amino-2-oxazolin-4-one, IR (KBr) cm$^{-1}$: 3380, 1707, 1637. $^1$H-NMR (CDCl$_3$) δ: 1.22(3H,d,J=7.0 Hz), 2.93(1H,dd,J=14.0&8.4 Hz), 3.04(3H, s), 3.32(1H,d,J=14.0&4.0 Hz), 3.95(1H,m), 4.37(1H,dd,J= 8.4&4.0 Hz), 7.07–7.41(9H,m), 7.70(1H,d,J=8.0 Hz), 8.01 (1H,bs).

(5S)-5-[(1R)-1-(indol-3-yl)ethyl]-2-(N-L-prolyl-N-methyl)amino-2-oxazolin-4-one, IR (KBr) cm$^{-1}$: 3289, 1707. $^1$H-NMR (CDCl$_3$) δ: 1.51 (3H,d,J=7.4 Hz), 1.89(2H,m), 2.06(2H,m), 2.78(3H,s), 3.00 (1H,m), 3.25(1H,m), 3.80(2H,m), 4.83(1H,d,J=3.2 Hz), 6.59 (1H,s), 7.09–7.21(3H,m), 7.38(1H,d,J=7.4 Hz), 7.64(1H,d, J=7.8 Hz), 8.13(1H,bs).

(5S)-2-(N-L-glutaminyl-N-methyl)amino-5-[(1R)-1-(indol-3-yl)ethyl]-2-oxazolin-4-one, IR (KBr) cm$^{-1}$: 3299, 1724, 1623. $^1$H-NMR (DMSO-d$_6$) δ: 1.18(3H,d,J=6.8 Hz), 2.03(2H,m), 2.22(2H,m), 2.99(3H, s), 3.66(1H,m), 4.27(2H,m), 6.91–7.12(3H,m), 7.32(1H,d, J=7.4 Hz), 7.58(1H,d,J=6.6 Hz), 9.57(1H,bs).

Example 15

(5S)-5-[(1R)-1-(Indol-3-yl)ethyl-2-(N-methanesulfonyl-N-methyl)amino-2-oxazolin-4-one To a mixture of indolmycin (100 mg) and triethylamine (217 μl) in tetrahydrofuran (5 ml) was added methanesulfonylchloride (90.3 μl) at −30° C. The whole was stirred for 5 minutes at −30° C. and then further stirred at 0° C. for 1 hour. Ethyl acetate was added to the mixture. The mixture was washed with water, saturated aqueous sodium hydrogen carbonate solution and brine respectively and then the ethyl acetate solution was dried over MgSO$_4$. Removal of the organic solvent gave a residue, to which was added isopropylether to provide the titled compound (74 mg, 57.0%).

IR (KBr) cm$^{-1}$: 3303, 1748. $^1$H-NMR (CDCl$_3$) δ: 1.53 (3H,d,J=7.4 Hz), 2.88(3H,s), 3.33(3H,s), 3.88–3.97(1H,m), 5.06(1H,d,J=3.4 Hz), 7.10–7.25(3H,m), 7.37(1H,d,J=7.0 Hz), 7.67(1H,d,J=7.8 Hz), 8.28(1H,bs).

Example 16

Following the same procedure as described in Example 15, the following compounds were prepared.

(5S)-2-(N-benzenesulfonyl-N-methyl)amino-5-[(1R)-1-(indol-3-yl)ethyl]-2-oxazolin-4-one IR (KBr) cm$^{-1}$: 3300, 1748. $^1$H-NMR (CDCl$_3$) δ: 1.23 (3H,d,J=7.2 Hz), 3.54(3H,s), 3.76–3.89(1H,m), 4.99(1H,d, J=2.6 Hz), 7.15–7.78(10H,m), 8.12(1H,bs).

Example 17

5-[1-(6-Fluoroindol-3-yl)ethyl]-2-methylamino-2-oxazolin-4-one

To a solution of acetoaldehyde (1.0 g) in toluene (7 ml) was added isopropylamine (1.3 g). The mixture was dried over magnesium sulfate and filtered. The filtrate was added to a solution of 6-fluoroindole (3.32 g) in acetic acid (20 ml) under ice cooling. The whole was stored at freezer for 3 days and was poured into the ice water. The mixture was neutralized with 25% ammonia water. The whole was extracted with ethyl acetate. The extract was washed with brine and then dried over MgSO$_4$. Removal of the solvent gave a residue, to which a mixture of ethyl acetate and ethyl ether was added to provide 6-fluoro-3-(1-isopropylamino)ethylindole (1.31 g) as a crystal.

$^1$H-NMR (CDCl$_3$) δ: 1.07(6H,m), 1.49(3H,d,J=6.6 Hz), 2.85(1H,m), 4.23(1H,q,6.6 Hz), 6.80–7.10(3H,m), 7.62(1H, dd,J=5.4&8.4 Hz), 8.12(1H,bs).

To a mixture of 6-fluoro-3-(1-isopropylamino)ethylindole (435 mg), benzyl 2-dimethylamino-4-oxo-2-oxazolin-5-carboxylate (518 mg) in acetonitrile (15 ml) was added tri-n-butylphosphine (492 μl). The mixture was refluxed for 2.5 hours. Removal of the solvent gave a residue, to which a mixture of ethyl acetate and ethyl ether in a ration of 10:1 was added to provide benzyl 2-dimethylamino-5-[1-(6-fluoroindol-3-yl)ethyl]-4-oxo-2-oxazolin-5-carboxylate (509 mg) as a crystal.

$^1$H-NMR (CDCl$_3$) δ: 1.28(2H,d,J=7.2 Hz), 1.51(1H,d,J= 7.2 Hz), 2.84–3.26(6H,m), 4.24(1H,m), 4.99(1.4H,ABq,J= 4.8 Hz), 5.32(0.7H,ABq,J=4.8 Hz), 6.70–7.70(9H,m), 8.14 (0.7H,bs), 8.45(0.35H,bs).

Benzyl 2-dimethylamino-5-[1-(6-fluoroindol-3-yl)ethyl]-4-oxo-2-oxazolin-5-carboxylate (500 mg) was dissolved into 15 ml of a solution of ethanol and tetrahydrofuran in a ration of 5:1. 10% palladium-carbon (170 mg) was added. The whole was subjected to hydrogenation under normal temperature and normal pressure for 1.5 hours. The whole was stirred at 80° C. under nitrogen atmosphere for 1 hour and then filtered to remove the catalyst. The filtrate was concentrated to give 2-dimethylamino-5-[1-(6-fluoroindol-3-yl)ethyl]-2-oxazolin-4-one (340 mg).

$^1$H-NMR (CDCl$_3$) δ: 1.43(1.2H,d,J=7.2 Hz), 1.62(1.8H, d,J=7.2 Hz), 2.97–3.06(6H,m), 3.60–3.80(1H,m), 4.90

(0.6H,d,J=1.5 Hz), 4.97(0.4H,d,J=1.5 Hz)I 6.85(1H,m), 6.90–7.30(2H,m), 7.58(1H,m), 8.66(0.4H,bs), 8.67(0.6H, bs).

2-Dimethylamino-5-[1-(6-fluoroindol-3-yl)ethyl]-2-oxazolin-4-one (340 mg) was dissolved into methylamine (5 ml) at −10° C. The mixture was stirred for 3 hours at the same temperature. The mixture was concentrated to give a residue, which was subjected to column chromatography. Elution with hexane-acetone (1:1) provided the titled compound (254 mg).

IR (KBr) cm$^{-1}$: 3195, 1733, 1644, 1627. $^1$H-NMR (DMSO-d$_6$) δ: 1.18(0.9H,d,J=7.2 Hz), 1.27(0.4H,d,J=7.4 Hz), 1.43(1.1H,d,J=7.2 Hz), 1.49(0.6H,d,J=7.2 Hz), 2.60–2.80(3H,m), 3.40–3.60(1H,m), 4.80–5.00(1H,m), 6.81 (1H,m), 7.00–7.20(2H,m), 7.55(1H,m), 8.50–8.70(1H,bs), 10.9–11.0(1H,m).

Example 18

Following the same procedure as described in Example 11, the following compounds were prepared.

(5S)-2-[N-(3-benzyloxycarbonylaminopropionyl)-N-methylamino]-5-[(1R)-1-(indol-3-yl)ethyl]-2-oxazolin-4-one, IR (KBr) cm$^{-1}$: 3327, 2971, 1715, 1557, 1539, 1456, 1397, 1316, 1246, 1200, 1138. $^1$H-NMR (CDCl$_3$) δ: 1.48 (3H,d,J=7.4 Hz), 2.76–3.07(2H,m), 3.20(3H,s), 3.30–3.42 (2H,m), 3.93(1H,m), 5.06(1H,d,J=3.2 Hz), 5.11(2H,s), 7.07–7.22(3H,m), 7.30–7.40(6H,m), 7.62(1H,d,J=7.8 Hz), 8.24(1H,bs).

(5S)-5-[(1R)-1-(indol-3-yl)ethyl]-2-[N-[3-(N-benzyloxycarbonyl-N-methyl)amino]propionyl-N-methylamino]-2-oxazolin-4-one, IR (KBr) cm$^{-1}$: 3296, 1700–1750, 1646. $^1$H-NMR (CDCl$_3$) δ: 1.38–1.50(3H,m), 2.86(1.2H,s), 2.90(1.8H,s), 2.97–3.11(2H,m), 3.16(1.8H,s), 3.22(1.2H,s), 3.4–3.6(2H, m), 3.92(1H,m), 5.04(1H,d,J=2.8 Hz), 5.13(2H,s), 6.9–7.4 (9H,m), 7.61(1H,d,J=7.4 Hz), 8.1–8.3(1H,bs).

(5S)-2-[N-(4-benzyloxycarbonylaminobutyryl)-N-methylamino]-5-[(1R)-1-(indol-3-yl)ethyl]-2-oxazolin-4-one, IR (KBr) cm$^{-1}$: 3337, 2969, 2940, 1711, 1561, 1537, 1454, 1433, 1397, 1314, 1252, 1192. $^1$H-NMR (CDCl$_3$) δ: 1.48(3H,d,J=7.4 Hz), 1.64(2H,m), 2.76(2H,m), 3.12(2H,m), 3.23(3H,s), 3.93(1H,m), 4.82(1H,bs), 5.05(1H,d,J=3.2 Hz), 5.12(2H,s), 7.00–7.41(9H,m), 7.62(1H,d,J=6.8 Hz), 8.35 (1H,bs).

(5S)-2-[N-(4-benzylsuccinyl)-N-methylamino]-5-((1R)-1-(indol-3-yl)ethyl]-2-oxazolin-4-one, IR (KBr) cm$^{-1}$: 3400, 1733, 1558, 1456, 1432, 1394, 1209, 1166. $^1$H-NMR (CDCl$_3$) δ: 1.46(3H,d,J=7.3 Hz), 2.52–2.66(2H,m), 2.99–3.34(2H,m), 3.24(3H,s), 3.93 (1H,dq,J=7.3&3.0 Hz), 5.06(1H,d,J=3.0 Hz), 5.12(2H,s), 7.07–7.38(9H,m), 7.63(1H,d,J=7.2 Hz), 8.10(1H,bs).

(5S)-2-[N-[(2S)-2,5-bis(N-benzyloxycarbonylamino)-pentanoyl]-N-methylamino-5-[(1R)-1-(indol-3-yl)ethyl-2-oxazolin-4-one, IR (KBr) cm$^{-1}$: 3327, 3064, 3033, 2968, 2939, 2877, 1718, 1523, 1455, 1388, 1345, 1263, 1220. $^1$H-NMR (CDCl$_3$) δ: 1.25–1.55(4H,m), 1.57(3H,d,J=6 Hz), 2.33(3H, s), 2.70–2.90(2H,m), 4.15–4.30(2H,m), 4.83–5.29(7H,m), 7.07–7.68(15H,m), 8.12(1H,bs).

(5S)-2-[N-[(S)-4-benzyl(N-benzylcarbonylamino)-aspartyl]-N-methylamino]-5-[(1R)-1-(indol-3-yl)ethyl]-2-oxazolin-4-one, IR (KBr) cm$^{-1}$: 3396, 3064, 3035, 2970, 2937, 1722, 1455, 1423, 1386, 1344, 1311. $^1$H-NMR (CDCl$_3$) δ: 1.36, 1.60(total 3H,d,J=7.8 Hz), 2.19(3H,s), 2.28–3.18(2H,m), 3.78(!H,m), 4.21(1H,m), 4.29–4.47(1H,m), 4.99–5.32(5H, m), 6.70–7.47(14H,m), 7.68(1H,d,J=8.2 Hz), 8.10(1H,bs).

(5S)-5-[(1R)-1-(indol-3-yl)ethyl]-2-[N-[(S)-4-methyl[N-benzyloxycarbonylamino)-aspartyl]-N-methylamino]-2-oxazolin-4-one, IR (KBr) cm$^{-1}$: 3402, 3060, 3037, 2954, 2937, 1722, 1457, 1436, 1376, 1344, 1313. $^1$H-NMR (CDCl$_3$) δ: 1.36, 1.61(total 3H,d,J=7.6 Hz), 2.20(3H,s), 2.82–3.82(3H,m), 3.57,3.60(total 3H,s), 4.18–4.50(2H,m), 5.02–5.32(3H,m), 6.85–7.36(9H,m), 7.45,7.68(total 1H,d,J=7.2 Hz), 8.14(1H, bs).

(5S)-2-[N-(2-tert-butyldimethylsilyloxyoctanoyl)-N-methylamino]-5-[(1R)-1-(indol-3-yl)ethyl]-2-oxazolin-4-one, $^1$H-NMR (CDCl$_3$) δ: −0.1–0.1(6H,m), 0.85(4.5H,s), 0.87 (4.5H,s), 1.0–1.2(10H,m), 1.46(3H,t,J=7.0 Hz), 3.25(1.5H, s), 3.26(1.5H,s), 3.93(1H,dq,J=3.0&7.0 Hz), 5.05(0.5H,d,J= 3.0 Hz), 5.07(0.5H,d,J=3.0 Hz), 5.40–5.48(1H,m), 7.1–7.7 (5H,m), 8.13(1H,bs).

(5S)-2-[N-(2-benzyloxyoctanoyl)-N-methylamino]-5-((1R)-1-(indol-3-yl)ethylI-2-oxazolin-4-one, IR (KBr) cm$^{-1}$: 1810, 1733, 1704, 1634. $^1$H-NMR (CDCl$_3$) δ: 0.8–0.9(3H,m), 1.1–1.4(9H,m), 1.45(3H,d,J=7.2 Hz), 1.5–1.83(1H,m), 3.2–3.3(3H,m), 3.89(1H,dq,J= 3.0&7.2 Hz), 3.97–4.73(3H,m), 5.03(0.5H,m), 5.11–5.17 (0.5H,m), 6.9–7.7(10H,m), 8.11(0.5H,bs), 8.16(0.5H,bs).

(5S)-2-(N-benzyloxyacetyl-N-methylamino)-5-[(1R)-1-(indol-3-yl)ethyl]-2-oxazolin-4-one, IR (KBr) cm$^{-1}$: 3347, 1733, 1627, 1557. $^1$H-NMR (CDCl$_3$) δ: 1.46(3H,d,J=7.2 Hz), 3.26(3H,s), 3.92(1H,dq,J= 3.4&7.2 Hz), 4.42,4.66(2H,ABq,J=18.0 Hz), 4.55(2H,s), 5.05(1H,d,J=3.4 Hz), 7.0–7.7(10H,m), 8.09(1H,bs).

(5S)-2-[N-(2-benzyloxy-4-methylpentanoyl)-N-methylamino]-5-[(1R)-1-(indol-3-yl)ethyl]-2-oxazolin-4-one, IR (KBr) cm$^{-1}$: 1742, 1729, 1557, 1538. $^1$H-NMR (CDCl$_3$) δ: 0.66,0.78(each 3H,d,J=6.6 Hz), 0.88,0.93(3H,d, J=7.0 Hz), 1.3–1.6(3H,m), 3.2–3.3(3H,m), 3.91(1H,m), 3.8–4.6(2.5H,m), 5.00–5.05(1H,m), 5.25(0.5H,m), 7.0–7.7 (10H,m), 8.09–8.2(1H,m).

Example 19

Following the same procedure as described in Example 6, the following compounds were prepared.

(5S)-5-[(1R)-1-(indol-3-yl)ethyl]-2-[N-lauroyl-N-methylamino]-2-oxazolin-4-one,

IR (KBr) cm$^{-1}$: 3298, 2925, 2854, 1729, 1558, 1538, 1455, 1394, 1195. $^1$H-NMR (CDCl$_3$) δ: 0.83(3H,t,J=6.6 Hz), 1.23–1.35(16H,m), 1.46(3H,d,J=7.2 Hz), 1.51–1.64 (2H,m), 2.85(2H,m)r 3.25(3H,s), 3.93(1H,m), 5.06(1H,d,J= 3.0 Hz), 7.09–7.25(3H,m), 7.37(1H,d,J=7.8 Hz), 7.64(1H, d,J=7.8 Hz), 8.14(1H,bs).

(5S)-2-[N-chloroacetyl-N-methylamino]-5-((1R)-1-(indol-3-yl)ethyl]-2-oxazolin-4-one, IR (KBr) cm$^{-1}$: 3383, 2972, 1733, 1558, 1455, 1436, 1398, 1340, 1317, 1203. $^1$H-NMR (CDCl$_3$) δ: 1.52(3H,d,J= 7.3 Hz), 3.28(3H,s), 3.95(1H,m), 4.48(1H,d,J=16.5 Hz), 4.72(1H,d,J=16.5 Hz), 5.08(1H,d,J=3.3 Hz), 7.08–7.26(3H, m), 7.38(1H,d,J=7.4 Hz), 7.62(1H,d,J=7.6 Hz), 8.25(1H,bs).

(5S)-2-[N-[2-(5-amino-1,2,4-thiodiazol-3-yl)-2(Z)-ethoxyiminoacetyl]-N-methylamino]-5-(1R)-1-(indol-3-yl) ethyl]-2-oxazolin-4-one, IR (KBr) cm$^{-1}$: 3400, 2976, 1747, 1714, 1616, 1538, 1455, 1403, 1245, 1224. $^1$H-NMR (CDCl$_3$) δ: 1.14(3H,t,J=

7.1 Hz), 1.23(3H,m), 3.56(3H,s), 3.79(1H,m), 5.08(1H,m), 6.85–7.25(5H,m), 7.33(1H,d,J=8.2 Hz), 7.56(1H,d,J=7.0 Hz), 8.60(1H,bs).

(5S)-2-(N-allyloxalyl-N-methylamino)-5-[(1R)-1-(indol-3-yl)ethyl]-2-oxazolin-4-one, IR (KBr) cm$^{-1}$: 1746, 1704, 1634, 1615. $^1$H-NMR (CDCl$_3$) δ: 1.25–1.45(3H,m), 3.00–3.11(3H,m), 3.76(1H, dq,J=3.4&7.2 Hz), 4.90–5.01(3H,m), 5.40(1H,d,J=11.2 Hz), 5.51(1H,dd,J=1.2 &17.0 Hz), 5.95–6.15(1H,m), 7.1–7.7 (5H,m), 8.46(1H,bs).

Example 20

Following the same procedure as described in Example 13, the following compounds were prepared.

(5S)-2-[N-(3-aminopropionyl)-N-methylamino]-5-[(1R)-1-(indol-3-yl)ethyl]-2-oxazolin-4-one, IR (KBr) cm$^{-1}$: 3266, 2969, 2928, 1705, 1622, 1584, 1495, 1456, 1399, 1341, 1308, 1236. $^1$H-NMR (CDCl$_3$) δ: 1.27(3H,d,J=7.0 Hz), 2.78(2H,t,J=7.0 Hz), 3.30(3H,s), 3.56 (2H,t,J=7.0 Hz), 3.65(2H,bs), 3.77(1H,m), 4.48(1H,m), 7.06–7.21(3H,m), 7.35(1H,d,J=7.6 Hz), 7.71(1H,d,J=7.0 Hz), 8.08(1H,bs).

(5S)-5-[(1R)-1-(indol-3-yl)ethyl]-2-[N-[(S)-4-methylaspartyl]-N-methylamino]-2-oxazolin-4-one, IR (KBr) cm$^{-1}$: 3352, 2966, 1735, 1643, 1577, 1488, 1457, 1438, 1403, 1322, 1255, 1099. $^1$H-NMR (CDCl$_3$) δ: 1.27(3H,d,J=7.1 Hz), 2.73(1H,dd,J=17.6&9.0 Hz), 3.07(1H, dd,J=17.6&3.4 Hz), 3.15(3H,s), 3.57(1H,bs), 3.76(3H,s), 3.82(1H,m), 4.46(1H,dd,J=9.0&3.4 Hz), 4.54(1H,m), 7.03–7.27(3H,m), 7.36(1H,d,J=7.0 Hz), 7.73(1H,d,J=7.4 Hz), 8.07(1H,bs), 9.12(1H,bs).

(5S)-2-[N-[(S)-aspartyl]-N-methylamino]-5-[(1R)-1-(indol-3-yl)ethyl]-2-oxazolin-4-one, IR (KBr) cm$^{-1}$: 3400, 1720, 1629, 1560, 1425, 1399, 1342. $^1$H-NMR (DMSO-d$_6$) δ: 1.17(3H,d,J=7.0 Hz), 2.30–2.70(2H,m), 2.99(3H,s), 3.64(1H,m), 4.24–4.38(2H, m), 6.93–7.36(4H,m), 7.60(1H,d,J=8.0 Hz), 10.78(1H,bs).

(5S)-5-[(1R)-1-(indol-3-yl)ethyl]-2-[N-methyl-N-(3-methylaminopropionyl)amino]-2-oxazolin-4-one, IR (KBr) cm$^{-1}$: 3244, 1733, 1607. $^1$H-NMR (CDCl$_3$) δ: 1.49(2.0H,d,J=7.4 Hz), 1.54(1.0H,d,J=7.4 Hz), 1.9–2.5(2H, m), 2.59(1.0H,d,J=2.4 Hz), 2.71(2.0H,d,J=2.4 Hz), 2.97 (2.0H,s), 3.00(1.0H,s), 3.4–3.6(1H,m), 3.6–3.8(1H,m), 3.86 (1H,dq,J=3.0&7.4 Hz), 4.80(0.33H,bs), 4.98(1H,d,J=3.0 Hz), 6.08(0.67H,bs), 7.0–7.7(5H,m), 8.64(0.67H,bs), 8.70 (0.33H,bs).

Example 21

(5S)-2-(N-(2-Benzylphthaloyl)-N-methylaminol-5-[(1R)-1-(indoly-3-yl)ethyl]-2-oxazolin-4-one To a solution of mono-benzyl phthalic ester (1.60 g) in toluene (20 ml) was added thionyl chloride (1 ml). After being stirred for one hour at 80° C., the mixture was concentrated under the reduced pressure to afford a residue. Tetrahydrofuran (20 ml) was added to the residue and then indolmycin (400 mg) was added at −15° C. After triethylamine (1.74 ml) was added, the mixture was stirred for 21 hours at room temperature. The whole was diluted with ethyl acetate (100 ml). The mixture was washed with water (35 ml), saturated aqueous sodium hydrogen carbonate solution (35 ml×3) and brine (35 ml) respectively and the dried over MgSO$_4$. Concentration of the solution under the reduced pressure gave a residue, which was subjected to column-chromatography. Eluent with ethyl acetate-hexane was collected and concentrated. The content was solidified from hexane. The solid product was collected by filtration and dried to provide the titled compound (161 mg).

IR (KBr) cm$^{-1}$: 3400, 1714, 1538, 1455, 1399, 1278, 1222. $^1$H-NMR (CDCl$_3$) δ: 1.07(3H,d,J=7.1 Hz), 3.44(3H, s), 3.60(1H,m), 4.72(1H,d,J=2.6 Hz), 5.17(1H,d,J=12.0 Hz), 5.26(1H,d,J=12.0 Hz), 6.31(1H,d,J=2.4 Hz), 7.06–7.52 (12H,m), 7.86(1H,bs), 7.95(1H,dd,J=7.6&1.4 Hz).

Example 22

(5S)-5-[(1R)-1-(Indol-3-yl)ethyl]-2-(N-methyl-N-trifluoroacetylamino)-2-oxazolin-4-one Indolmycin (401 mg) was dissolved into tetrahydrofuran (38 ml). To this solution were added triethylamine (1.5 ml) and trifluoroacetic anhydride (1.0 ml). The whole was stirred for 1 hour at room temperature. The mixture was diluted with ethyl acetate (100 ml). The whole was washed with water, brine and dried over magnesium sulfate. The solution was concentrated to give a residue, which was subjected to silica gel chromatography. Elution with hexane-acetone (1:1) gave the titled compound (375 mg).

IR (KBr) cm$^{-1}$: 1733, 1652, 1634, 1615. $^1$H-NMR (CDCl$_3$) δ: 1.33(0.45H,d,J=7.0 Hz), 1.34(2.55H,d,J=7.0 Hz), 2.97–3.13(3H,m), 3.77(1H,dq,J=2.2&7.0 Hz), 4.85 (0.15H,d,J=2.2 Hz), 4.97(0.85H,d,J=2.2 Hz), 7.3–7.7(5H, m), 8.4–8.51(1H,bs).

Example 23

2-Methylamino-5-[(5-chloroindol-3-yl)methyl]-2-oxazolin-4-one

To a solution of 5-chloro-3-formylindole (5.00 g) in tetrahydrofuran (135 ml) was added sodium hydride (60% oil suspension, 3.53 g). The mixture was stirred for 20 minutes at room temperature. Carbobenzoxychloride (6.64 ml) was added to the mixture. After being stirred for 1 hour at room temperature, the whole was poured into ice water. The mixture was extracted with ethyl acetate. The extract was washed with brine and dried over magnesium sulfate. The solution was concentrated to give a residue, which was subjected to silica gel chromatography. Elution with hexane-ethyl acetate (5:1) provided 1-benzyloxycarbonyl-5-chloro-3-formylindol (5.74 g) as a crystal.

$^1$H-NMR (CDCl$_3$) δ: 5.51(2H,s), 7.36–7.52(6H,m), 8.10 (1H,d,J=9.2 Hz), 8.27(1H,s), 8.30(1H,d,J=2.2 Hz), 10.06 (1H,s).

To a solution of 1-benzyloxycarbonyl-5-chloro-3-formylindol (2.00 g) in methanol (13 ml) was added sodium borohydride (241 mg) at 0° C. After the mixture was stirred for 15 minutes at the same temperature, ice water was added to the mixture. Potassium carbonate was added to make the mixture saturate. The whole was extracted with ether and the extract was dried over magnesium sulfate. Concentration of the mixture gave a residue, to which hexane was added. 1-benzyloxycarbonyl-5-chloro-3-hydroxymethylindol (1.80 g) was obtained as a crystal.

$^1$H-NMR (CDCl$_3$) δ: 1.63(1H,t,J=5.0 Hz), 4.79(2H,d,J= 5.0 Hz), 5.44(2H,s), 7.26–7.45(6H,m), 7.63(2H,s), 8.09(1H, d,J=8.8 Hz).

To a solution of 1-benzyloxycarbonyl-5-chloro-3-hydroxymethylindole (1.45 g) in dichloromethane (23 ml) was added thionylchloride (0.797 μl) at −78° C. After the mixture was stirred for 1.5 hours at room temperature, the reaction mixture was concentrated under the reduced pressure to give a residue. Hexane was added to the residue. 1-benzyloxycarbonyl-5-chloro-3-chloromethylindole (1.43 g) was obtained as a crystal.

$^1$H-NMR (CDCl$_3$) δ: 4.70(2H,s), 5.44(2H,s), 7.32(1H,dd, J=8.8&1.8 Hz), 7.39–7.46(5H,m), 7.64(1H,d,J=1.8 Hz), 7.69(1H,s), 8.10(1H,d,J=8.8 Hz).

To a solution of diisopropylamine (1.18 ml) in tetrahydrofuran (24 ml) was added a 1.6 M solution (5.24 ml) of n-butyllithium in hexane under ice cooling. The mixture was cooled to −78° C., to which was added 2-dimethylamino-2-oxazolin-4-one (1.07 g). The mixture was stirred for 30 minutes at room temperature and cooled again to −78° C. 1-benzyloxycarbonyl-5-chloro-3-chloromethylindol (1.40 g) was added. The whole was stirred at −78° C. to −40° C. for 30 minutes, at 0° C. for 2 hours and at room temperature for 40 minutes respectively. To the reaction mixture was added water and the whole was extracted with ethyl acetate. The extract was dried over magnesium sulfate and concentrated to give a residue, which was subjected to silica gel chromatography. Elution with hexane-ethyl acetate (1:1) gave 5-[(5-chloroindol-3-yl)methyl-2-dimethylamino-2-oxazolin-4-one (232 mg) as a crystal.

$^1$H-NMR (CDCl$_3$) δ; 2.96(3H,s), 2.98(3H,s), 3.22(1H,dd, J=15.8&4.0 Hz), 3.45(1H,dd,J=15.8&4.0 Hz), 4.98(1H,t,J= 4.0 Hz), 7.07(1H,s), 7.09(1H,d,J=8.8 Hz), 7.29(1H,d,J=8.8 Hz), 7.59(1H,s), 8.64(1H,bs).

To [(5-chloroindol-3-yl)methyl]-2-dimethylamino-2-oxazolin-4-one (200 mg) was added methylamine (20 ml). The mixture was refluxed at −6° C. for 1 hour. Removal of methylamine gave a residue, to which was added ether. The titled compound (120 mg) was obtained as a crystal.

IR (KBr) cm$^{-1}$: 2986, 1641, 1413, 1390, 1304, 1242, 1103. $^1$H-NMR (DMSO-d$_6$) δ: 2.73(3H,s), 3.01(1H,m), 3.19 (1H,m), 4.95(1H,m), 7.03(1H,d,J=8.8 Hz), 7.20(1H,s), 7.34 (1H,dd,J=8.8&1.8 Hz), 7.58(1H,d,J=1.8 Hz), 8.31(1H,bs).

Example 24

Following the same procedure as described in Example 23, the following compounds were prepared.

2-methylamino-5-[(2-methylindol-3-yl)methyl]-2-oxazolin-4-one,

IR (KBr) cm$^{-1}$: 2912, 1655, 1508, 1408, 1305, 1251, 1238, 746. $^1$H-NMR (DMSO-d$_6$) δ: 2.50(3H,s), 2.70(3H,s), 2.93–3.20(2H,m), 4.86(1H,m), 6.86–7.00(2H,m), 7.20(1H, d,J=7.2 Hz), 7.40(1H,d,J=6.9 Hz), 8.48(1H,bs), 10.76(1H, bs).

5-[(5-benzyloxyindol-3-yl)methyl]-2-methylamino-2-oxazolin-4-one,

IR (KBr) cm$^{-1}$: 1667, 1640, 1485, 1412, 1304. $^1$H-NMR (DMSO-d$_6$) δ: 2.68(1.5H,s), 2.99(1H,m), 3.21(1H,m), 4.95 (1H,dd,J=7.0&3.4 Hz), 6.79(1H,d,J=8.8 Hz), 7.08–7.52(8H, m), 10.78(1H,bs).

2-methylamino-5-[(5,6-methylenedioxyindoly-3-yl) methyl]-2-oxazolin-4-one, $^1$H-NMR (DMSO-d$_6$) δ: 2.73 (3H,d,J=5.0 Hz), 2.96–3.15(2H,m), 4.89–4.91(1H,m), 5.92 (2H,s), 6.85(1H,s), 6.96(1H,s), 6.99(1H,s), 8.58(1H,bs).

Example 25
2-Methylamino-5-(1H-pyrro[2,3-b]pyridin-3-yl)methyl-2-oxazolin-4-one

To a solution of diisopropylamine (0.75 ml) in tetrahydrofuran (35 ml) was added 1.6M solution (3.35 ml) of n-butyllithium in hexane under ice cooling. The whole was cooled to −78° C. 2-dimethylamino-2-oxazolin-4-one (686 mg) was added and then the whole was stirred for 30 minutes at room temperature. The mixture was cooled again to −78° C., to which was added 3-chloromethyl-1H-pyrro [2,3-b]pyridine (230 mg). The whole was stirred for 4 hours at room temperature. To the reaction mixture was added water and the whole was extracted with ethyl acetate. The extract was dried over magnesium sulfate and concentrated to give a residue, which was subjected to silica gel chromatography. Elution with ethyl acetate-ethanol (10:1) provided 2-dimethylamino-5-(1H-pyrro[2,3-b]pyridin-3-yl) methyl-2-oxazolin-4-one (51 mg).

$^1$H-NMR (CDCl$_3$) δ: 2.95(3H,s); 3.03(3H,s), 3.26(1H,dd, J=15.9&5.5 Hz), 3.48(1H,dd,J=15.9&4.3 Hz), 4.97(1H,dd, J=5.5&4.3 Hz), 7.09(1H,dd,J=7.9&4.8 Hz), 7.24(1H,s), 7.98(1H,dd,J=7.9&1.5 Hz), 8.29(1H,J=4.8&1.5 Hz), 9.64 (1H,bs).

2-dimethylamino-5-(1H-pyrro[2,3-b]pyridin-3-yl) methyl-2-oxazolin-4-one (50 mg) was added to methylamine (1 ml). After the reaction mixture was refluxed for 1 hour, methylamine was removed to give a residue, which was subjected to silica gel chromatography. Eluent with ethyl acetate-ethanol was concentrated to give a residue, which was solidified using chloroform. The solid was washed with diethyl ether and dried under the reduced pressure to give the titled compound (32 mg).

IR (KBr) cm$^{-1}$: 3215, 1645, 1516. $^1$H-NMR (DMSO-d$_6$) δ: 2.71,2.73(total 3H,each s), 2.99–3.32(2H,m), 4.97(1H,dd, J=6.7&3.9 Hz), 7.03(1H,dd,J=7.8&4.7 Hz), 7.24(1H,d,J= 2.1 Hz), 7.96(1H,d,J=7.8 Hz), 8.18(1H,d,J=4.7 Hz), 8.58 (1H,bs), 11.43(1H,bs).

Example 26

Following the same procedure as described in Example 25, the following compounds were prepared.

5-(bezo[b]thiophen-3-yl)methyl-2-methylamino-2-oxazolin-4-one,

IR (KBr) cm$^{-1}$: 3210, 1768, 1678. $^1$H-NMR (DMSO-d$_6$) δ: 2.68,2.79(total 3H,each s), 3.18(1H,dd,J=15.7&8.4 Hz), 3.42(1H,m), 5.06(1H,m), 7.35–7.45(2H,m), 7.51(1H,s), 7.82–7.99(2H,m), 8.69(1H,bs).

5-[(1-benzylindol-3-yl)methyl]-2-methylamino-2-oxazolin-4-one,

IR (KBr) cm$^{-1}$: 1663, 1508, 1410, 1402, 1298, 729. $^1$H-NMR (DMSO-d$_6$) δ: 2.68(1H,s), 2.72(2H,s), 3.07(1H, m), 3.30(1H,m), 4.98(1H,dd,J=6.2&2.4 Hz), 5.37(2H,s), 6.96–7.38(9H,m), 7.56(1H,d,J=7.0 Hz), 8.55(1H,bs).

Example 27

Following the same procedure as described in Example 17, the following compounds were prepared.

5-[(1-(4-methylindol-3-yl)ethyl]-2-methylamino-2-oxazolin-4-one,

IR (KBr) cm$^{-1}$: 3183, 1733, 1623. $^1$H-NMR (CDCl$_3$) δ: 1.25–1.50(3H,m), 2.69–3.0(3H,m), 4.05–4.25(1H,m), 4.86 (0.5H,d,J=3.6 Hz), 4.96(0.5H,d,J=2.6 Hz), 6.84(1H,m), 6.98–7.25(3H,m), 8.29(0.5H,bs), 8.38(0.5H,bs), 9.30(1H, bs).

5-[(1-(4-benzyloxyindol-3-yl)ethyl]-2-methylamino-2-oxazolin-4-one,

IR (KBr) cm$^{-1}$: 3199, 1733, 1652, 1615. $^1$H-NMR (CDCl$_3$) δ: 1.22–1.37(3H,m), 2.82–3.0(3H,m), 4.1–4.4(1H, m), 5.08(0.5H,d,J=4.8 Hz), 5.19(1.5H,m), 5.26(1H,s), 6.56 (1H,m), 6.9–7.1(3H,m), 7.29–7.6(5H,m), 8.23(0.5H,bs), 8.37(0.5H,bs), 9.25(1H,bs).

2-methylamino-5-[1-(7-methylindol-3-yl)ethyl]-2-oxazolin-4-one,

IR (KBr) cm$^{-1}$: 3357, 3214, 1733, 1652, 1615. $^1$H-NMR (DMSO-d$_6$) δ: 1.18(0.96H,d,J=7.4 Hz), 1.25(0.45H,d,J=7.0 Hz), 1.42(0.96H,d,J=7.2 Hz), 1.50(0.63H,d,J=7.6 Hz), 2.41 (1.5H,s), 2.44(1. 5H,s), 2.65–2.8(3H,m), 3.5–3.7(1H,m), 4.8–4.95(1H,m), 6.8–6.9(2H,m), 7.0–7.15(1H,m), 7.35–7.45(1H,m), 8.55(1H,bs).

5-[1-(4-methoxycarbonylindoly-3-yl)ethyl]-2-methylamino-2-oxazolin-4-one,

IR (KBr) cm$^{-1}$: 3278, 3203, 1713, 1635. $^1$H-NMR (DMSO-d$_6$) δ: 1.06(1.33H,d,J=7.0 Hz), 1.14(0.67H,d,J=7.0 Hz), 1.32(0.67H,d,J=7.0 Hz), 1.41(0.33H,d,J=7.6 Hz), 2.7–2.85(3H,m), 3.86(1.08H,s), 3.91(1.92H,s), 3.95–4.2 (1H,m), 4.65–4.85(1H,m), 7.0–7.2(1H,m), 7.3–7.5(2H,m), 7.55–7.65(1H,m), 11.40(1H,bs).

5-[1-(4-isopropylindol-3-yl)ethyl]-2-methylamino-2-oxazolin-4-one.

IR (KBr) cm$^{-1}$: 3266, 3216, 1725, 1634. $^1$H-NMR (DMSO-d$_6$) δ: 1.1–1.5(9H,m), 2.75–2.9(3H,m), 3.6–3.9(1H, m), 4.8–4.95(1H,m), 6.8–7.1(2H,m), 7.1–7.25(2H,m), 8.67 (1H,bs).

Example 28
5-[1-(4-Hydroxyindol-3-yl)ethyl]-2-methylamino-2-oxazolin-4-one

5-[1-(4-benzyloxyindol-3-yl)ethyl]-2-methylamino-2-oxazolin-4-one (149 mg) was dissolved in a mixture of ethanol and tetrahydrofuran (5:1.6 ml). 10% palladium-carbon (45 mg) was added and the whole was hydrogenated for 24 hours at room temperature under normal pressure. The catalyst was removed from the mixture by filtration and 10% palladium-carbon (45 mg) was added again. The whole was hydrogenated for additional 24 hours at room temperature under normal pressure. The reaction mixture was filtered to remove the catalyst. The filtrate was concentrated to give a residue, which was subjected to silica gel chromatography. Elution with hexane-acetone (1:1) provided the titled compound (72 mg).

IR (KBr) cm$^{-1}$: 3189, 1733, 1698, 1615. $^1$H-NMR (DMSO-d$_6$) δ: 1.0–1.15(1.92H,m), 1.30–1.35(1.08H,m), 2.7–2.85(3H,m), 3.7–4.0(1H,m), 4.92(0.12H,d,J=6.0 Hz), 5.02(0.31H,d,J=6.0 Hz), 5.08(0.20H,d,J=2.2 Hz), 5.13 (0.37H,d,J=2.2 Hz), 6.32(1H,d,J=5.2 Hz), 6.7–7.0(3H,m), 8.58(1H,bs), 9.40(1H,bs).

Example 29
5-[1-(4-Methoxyindol-3-yl)ethyl]-2-methylamino-2-oxazolin-4-one

5-[1-(4-benzyloxyindol-3-yl)ethyl]-2-dimethylamino-2-oxazolin-4-one (268 mg) was dissolved in a mixture of ethanol and tetrahydrofuran (7:3.10 ml). 10% palladium-carbon (80 mg) was added and the whole was hydrogenated for 5 hours at room temperature under normal pressure. The catalyst was removed from the mixture and 10% palladium-carbon (80 mg) was added again. The whole was hydrogenated for additional 24 hours at room temperature under normal pressure. The reaction mixture was filtered to remove the catalyst. The filtrate was concentrated to give 2-dimethylamino-5-[1-(4-hydroxyindol-3-yl)ethyl]-2-oxazolin-4-one (125 mg).

$^1$H-NMR (DMSO-d$_6$) δ: 1.02–1.15(3H,m), 3.00–3.10 (6H,m), 3.98(1H,m), 4.97–5.16(1H,m), 6.30–6.34(1H,m), 6.77–15 6.83(2H,m), 6.95(1H,m), 9.40(1H,bs), 10.69(1H, bs).

2-dimethylamino-5-[1-(4-hydroxyindol-3-yl)ethyl]2-oxazolin-4-one (120 mg) was dissolved into dimethylformamide (3 ml). Potassium carbonate (115 mg) and indomethane (156 l) were added. The mixture was stirred for 3 hours at room temperature and additional indomethane (78 μl) was added. The mixture was stirred for 36 hours at room temperature. To the reaction mixture was added water and the whole was extracted with ethyl acetate. The extract was washed with brine and dried over magnesium sulfate. Concentration of the ethyl acetate solution gave a residue, which was subjected to silica gel chromatography. Elution with hexane-acetone (1:1) provided 2-dimethylamino-5-[1-(4-methoxyindol-3-yl)ethyl]-2-oxazolin-4-one (54 mg).

$^1$H-NMR (CDCl$_3$) δ: 1.26(2.6H,d,J=7.0 Hz), 1.45(0.4H, d,J=7.2 Hz), 2.96(0.4H,s), 3.00(2.6H,s), 3.17(2.6H,s), 3.19 (0.4H,s), 3.90(0.4H,s), 3.93(2.6H,s), 4.25(1H,m), 4.98 (0.13H,d,J=3.4 Hz), 5.24(0.87H,d,J=2.2 Hz), 6.51(d,J=7.8 Hz), 6.95–7.14(3H,m), 8.16(1H,bs).

2-dimethylamino-5-[1-(4-methoxyindol-3-yl)ethyl]-2-oxazolin-4-one (50 mg) was added to methylamine (5 ml). The mixture was refluxed for 5 hours and additional methylamine (5 ml) was added. The whole was further refluxed for 2.5 hours. The-methylamine was distilled off to give a residue, which was subjected to silica gel chromatography. Elution with hexane-acetone (1:1) provided the titled compound (32 mg).

IR (KBr) cm$^{-1}$: 3286, 3199, 1733, 1623. $^1$H-NMR (DMSO-d$_6$) δ: 1.0–1.15(3H,m), 2.7–2.85(3H,m), 3.84(3H, s), 3.7–3.9(1H,m), 4.98(0.33H,d,J=2.2 Hz), 5.01(0.67H,d,J= 2.2 Hz), 6.46(1H,m), 6.9–7.1(3H,m), 8.60(1H,bs), 10.88 (1H,bs).

Example 30
5-[1-(4-Chloroindol-3-yl)ethyl]-2-methylamino-2-oxazolin-4-one 3-chloroindole (500 mg) and ethyl trans-2,3-epoxybutyrate (472 mg) were dissolved into dichloromethane (5 ml). To this mixture was added at −9° C. over 30 minutes titanium tetrachloride. The whole was stirred for 1 hour at −9° C. Ethyl trans-2,3-epoxybutyrate (405 mg) and titanium tetrachloride (405 μl) were added. The whole was further stirred for 1 hour at −9° C. Concentration of the reaction mixture gave a residue, to which was added ethyl acetate. The mixture was washed with brine and dried over magnesium sulfate. Concentration of the solution gave a residue, which was subjected to silica gel chromatography. Elution with hexane-ethyl acetate (1:3) provided ethyl (2S*, 3R*)-3-(4-chloroindol-3-yl)-2-hydroxybutylate (200 mg).

$^1$H-NMR (CDCl$_3$) δ: 1.27(3H,d,J=7.2 Hz), 1.33(3H,t,J= 7.0 Hz), 2.81(1H,d,J=5.2 Hz), 4.25–4.40(4H,m), 4.64(1H, dd,J=5.2&2.6 Hz), 7.06–7.10(2H,m), 7.24–7.29(2H,m), 8.22(1H,bs).

Sodium (100 mg) was dissolved into ethanol (5 ml). Ethyl (2S*,3R*)-3-(4-chloroindol-3-yl)-2-hydroxybutyrate (200 mg) and N,N'-dimethyl guanidine hydrogen bromide (143 mg) were added. The whole was refluxed for 16 hours. To the reaction mixture was added water and extracted with ethyl acetate. The extract was washed with brine and dried over magnesium sulfate. Concentration of the solution gave a residue, which was subjected to silica gel chromatography. Elution with hexane-acetone (1:1) provided the titled compound (25 mg).

$^1$H-NMR (CDCl$_3$) δ: 1.27–1.44(3H,m), 2.84–3.00(3H, m), 4.36–4.58(1H,m), 4.99–5.11(1H,m), 5.88(1H,m), 7.00–7.30(4H,m), 8.60–8.80(1H,m).

Example 31

5-[1-(Indol-3-yl)-2,2,2-trifluoroethyl]-2-methylamino-2-oxazolin-4-one

Sodium ethoxide (580 mg) was added to a solution of methyl 4,4,4-trifluoro-2-hydroxy-3-(indol-3-yl)butyrate (980 mg) and N,N'-dimethyl guanidine hydrogen bromide (630 mg) in ethanol (2.5 ml). The mixture was refluxed for 1.5 hours and then cooled. To the cooled reaction mixture was added ice water (20 ml). After the pH of the mixture was adjusted to 7 using acetic acid, the whole was extracted with ethyl acetate. The extract was washed with saturated aqueous sodium hydrogen carbonate solution and then dried over magnesium sulfate. Concentration of the solution under the reduced pressure gave residue, which was subjected to silica gel chromatography. Eluent with ethyl acetate-hexane was collected and concentrated to provide the titled compound (218 mg).

IR (KBr) cm$^{-1}$: 3283, 1769, 1717, 1659, 1541. $^1$H-NMR (DMSO-d$_6$) δ: 2.38–2.54(3H,m), 3.65–4.61(2H,m), 6.24–6.33(1H,m), 6.94–7.98(5H,m), 11.10–11.18(1H,m).

Example 32

2-Diacetylamino-5-[1-(indol-3-yl)ethyl]-2-oxazolin-4-one 2-amino-5-[1-(indol-3-yl)ethyl]-2-oxazolin-4-one (300 g) was dissolved into tetrahydrofuran (2 ml). Triethylamine (344 μl) and acetyl chloride (123 μl) were added under ice cooling. The mixture was stirred for 2 hours at 0° C. Triethylamine (344 μl) and acetyl chloride (123 μl) were added again. The whole was further stirred for 2 hours. To the reaction mixture was added water and the whole was extracted with ethyl acetate. The extract was washed with brine and dried over magnesium sulfate. Concentration of the solution gave a residue, which was subjected to silica gel chromatography. The eluent with hexane-acetone (1:1) was collected and concentrated to provide the titled compound (40 mg).

$^1$H-NMR (CDCl$_3$) δ: 1.45(1.92H,d,J=7.2 Hz), 1.57 (1.08H,d,J=7.2 Hz), 2.17(6H,s), 3.7–3.9(1H,m), 4.99 (0.36H,d,J=2.4 Hz), 5.07(0.64H,d,J=2.8 Hz), 7.0–7.4(4H, m), 7.6–7.7(1H,m), 8.32(1H,bs).

Example 33

2-Acetylamino-5-[1-(indol-3-yl)ethyl]-2-oxazolin-4-one 2-amino-5-[1-(indol-3-yl)ethyl]-2-oxazolin-4-one (100 mg) was dissolved into pyridine (0.5 ml). Acetic anhydride (117 μl) was added. The mixture was stirred for 2 hours at 80° C. To the reaction mixture was added water. The mixture was made acidic using 4N hydrochloric acid. The whole was extracted with ethyl acetate. The extract was washed with brine and dried over magnesium sulfate. Concentration of the solution gave a residue, which was subjected to the silica gel chromatography. The eluent with hexane-acetone (1:1) was collected and concentrated to provide the titled compound (16 mg).

IR (KBr) cm$^{-1}$: 1742, 1698. $^1$H-NMR (CDCl$_3$) δ: 1.42 (1.95H,d,J=7.2 Hz), 1.62(1.05H,d,J=7.2 Hz), 2.1–2.3(3H, m), 3.88(1H,dq,J=2.2&7.2 Hz), 5.00(0.35H,d,J=2.2 Hz), 5.04(0.65H,d,J=2.2 Hz), 7.0–7.4(5H,m), 7.67(1H,d,J=8.4 Hz), 8.19(1H,bs).

Experimental Example 1

Invitro Antimicrobial Test:

Determination of in vitro Antimicrobial Activity Against *Helicobacter pylori* and other Microorganisms Using 5 strains of *Helicobacter pylori*, 19 other bacterial species and 2 yeast species as test strains, the antimicrobial activities of various compounds were determined by the method described below (agar dilution method). The test compound was dissolved in dimethyl sulfoxide; this solution was 2-fold diluted step by step with sterilized distilled water to yield test samples. Two milliliters of each test sample was mixed with 18 ml of Brucella agar supplemented with 7% horse blood as a medium to prepare a determination plate. *Helicobacter pylori* was subjected to shaking culture at 37° C. in a gas pack jar incorporating CampyPak™ (BBL$^R$ Beckton Dickinson Microbiology Systems) for 20 hours, using Brucella broth medium supplemented with 2.5% fetal bovine serum, to yield a seed inoculum. The other test microorganisms were each cultured at 37° C. for 20 hours, using Brucella broth medium, to yield respective seed inocula.

Five microliters of each seed inoculum, previously adjusted to about 10$^6$ CFU/ml using Brucella broth medium supplemented with 2.5% fetal bovine serum was inoculated to each determination plate, and cultured at 37° C. in a gas pack jar incorporating CampyPak™ and water-soaked cotton absorbent for 4 days. After cultivation, strain growth was macroscopically examined; the minimum concentration for the absence of strain growth was taken as the MIC value (minimum inhibitory concentration) of the test compound.

The results are shown in Tables 2 and 3.

TABLE 2

Antimicrobial Activities of Indolmycin against Various Microorganisms [MIC (μg/ml)]

| | | | |
|---|---|---|---|
| 1 | *Escherichia coli* | K12 | >100 |
| 2 | *Escherichia coli* | NIHJ JC-2 | >100 |
| 3 | *Proteus mirabilis* | ATCC 21100 | >100 |
| 4 | *Proteus vulgaris* | IFO 3045 | >100 |
| 5 | *Proteus morganii* | IFO 3168 | >100 |
| 6 | *Klebsiella pneumoniae* | IFO 3317 | >100 |
| 7 | *Serratia marcescens* | IFO 3046 | >100 |
| 8 | *Salmonella typhimurium* | IFO 12529 | >100 |
| 9 | *Salmonella enteritidis* | IFO 3313 | >100 |
| 10 | *Citrobater freundii* | IFO 12681 | >100 |
| 11 | *Pseudomonas aeruginosa* | IFO 3080 | >100 |
| 12 | *Alcaligenes faecalis* | IFO 13111 | >100 |
| 13 | *Bacillus subtilis* | PCI 219 | >100 |
| 14 | *Bacillus cereus* | IFO 3514 | >100 |
| 15 | *Bacillus pumilus* | IFO 3813 | >100 |
| 16 | *Bacillus megaterium* | IFO 12108 | >100 |
| 17 | *Staphylococcus aureus* | FDA 209P | >100 |
| 18 | *Micrococcus luteus* | IFO 12708 | 12.5 |
| 19 | *Micrococcus flavus* | IFO 3242 | >100 |
| 20 | *Helicobacter pylori* | NCTC 11637 | 0.006 |
| 21 | *Candida albicans* | IFO 0583 | >100 |
| 22 | *Saccharomyces cerevisiae* | IFO 0209 | >100 |

TABLE 3

Antimicrobial Activities against Various Strains of *Helicobacter pylori* (in vitro)

| | MIC ($\mu$g/ml) | | | | |
|---|---|---|---|---|---|
| Compound | H. pylori NCTC 11637 | H. pylori NCTC 11916 | H. pylori CPY 433 | H. pylori TN 2 | H. pylori TN 58 |
| Indolymcin | 0.006 | 0.013 | 0.013 | 0.006 | 0.025 |
| Compound of Example 2 | 0.025 | — | 0.05 | 0.025 | 0.05 |

MIC was determined by agar dilution method using Brucella agar supplemented with 7% horse blood.

As seen from Tables 2 and 3, compound (I) exhibits very selective antimicrobial activity against the bacteria of the genus Helicobacter, represented by *Helicobacter pylori*.

Experimental Example 2
(Invivo Antimicrobial Activity Test)

After mongolian gerbils (MGS/Sea, male, 6 weeks of age) were fasted for 24 hours, *Helicobacter pylori* TN2GF4 was inoculated to the stomach at $10^{7.08}$ per mongolian gerbil. Starting at 11 days after infection, a 3, 10, 30, or 100 mg/kg suspension of the test compound in a 0.5% aqueous solution of methyl cellulose was orally administered twice daily (morning and evening) for 3 days. On the day after final administration, the stomach of each infected mongolian gerbil was excised and disrupted; a series of 10-fold dilutions of the stomach homogenate were each inoculated to modified Skirrow's medium supplemented with activated charcoal and cultured under microaerophilic conditions at 37° C. for 4 days, after which clearance effect was assessed on the basis of the presence or absence of bacterial growth. The results are shown in Table 4. Bacterial cell counts are expressed in mean±standard deviation after Dunnett's test against the control group.

In Table 4, ** indicates p<0.01.

TABLE 4

| Test Compound | Dose (mg/kg) | Clearance Rate (%) | Bacterial Detection (log CFU/ gastric wall) |
|---|---|---|---|
| Control (0.5% methyl cellulose solution) | — | 0/4 (0) | 6.36 ± 0.19 |
| Indolmycin | 3 | 0/5 (0) | 4.61 ± 1.84 |
| | 10 | 0/5 (0) | 2.76 ± 1.04** |
| | 30 | 1/4 (25) | 1.96 ± 0.78** |
| | 100 | 4/5 (80) | 1.48 ± 0.00** |

As shown in Table 4, indolmycin at 10 mg/kg or higher reduced the mongolian gerbil gastric bacterial cell count with dose dependency, the clearance rates achieved being 25% at 30 mg/kg and 80% at 100 mg/kg.

These findings demonstrate that the preparation of the present invention is effective against the gastric ulcer, gastritis and gastric cancer caused by Helicobacter pyloriinfection.

Preparation Example

For use as a therapeutic agent for *Helicobacter pylori* infections, the preparation of the present invention, which contains a compound represented by formula (I) or a salt thereof, can be produced with the following formulations:

| 1. Capsules | |
|---|---|
| (1) Indolmycin | 100 mg |
| (2) Lactose | 90 mg |
| (3) Microcrystalline cellulose | 70 mg |
| (4) Magnesium stearate | 10 mg |
| Total | 270 mg per capsule |

Components (1), (2) and (3) and a half portion of component (4) were mixed and granulated. To these granules, the remaining portion of component (4) was added, and the whole mixture was packed in a gelatin capsule.

| 2. Tablets | |
|---|---|
| (1) Indolmycin | 100 mg |
| (2) Lactose | 35 mg |
| (3) Corn starch | 150 mg |
| (4) Microcrystalline cellulose | 30 mg |
| (5) Magnesium stearate | 5 mg |
| Total | 320 mg per tablet |

Components (1), (2) and (3), a two-third portion of component (4) and a half portion of component (5) were mixed and granulated. To these granules, the remaining portions of components (4) and (5) were added, and the whole mixture was tableted by compressive tableting.

Industrial Applicability

Compound (I) or a salt thereof exhibits very specific potent antibacterial activity against the bacteria of the genus Helicobacter represented by *Helicobacter pylori*. The use of compound (I) of the present invention or a salt thereof therefore provides the desired effect for an anti-*Helicobacter pylori* agent at doses much lower than the effective doses of conventional antibacterial agents for the bacteria of the genus Helicobacter (especially *Helicobacter pylori*).

Compound (I) or a salt thereof is effective in the prevention or treatment of various diseases caused by bacteria of the genus Helicobacter such as duodenal ulcer, gastric ulcer, chronic gastritis and gastric cancer, and, because *Helicobacter pylori* is a major cause of ulcer recurrence, compound (I) or a salt thereof is also effective in the prevention of ulcer recurrence.

Also, compound (I) or a salt thereof exhibits no antibacterial action against gram-positive bacteria such as those of the genera Staphylococcus and Bacillus and against gram-negative bacteria such as those of the genera Escherichia, Pseudomonas, Proteus, Klebsiella, Serratia, Salmonella, Citrobacter and Alcaligenes. Compound (I) or a salt thereof is therefore selectively effective in the prevention or treatment of diseases caused by bacteria of the genus Helicobacter, and can be used as a safe pharmaceutical without adverse effects having little influence on other bacteria and fungi.

Compound (I) or a salt thereof is stable and of low toxicity. Accordingly, the present invention provides an excellent anti-*Helicobacter pylori* agent without adverse effects.

What is claimed is:

1. A method for prevention or treatment of a disease associated with *Helicobacter pylori* infection in a mammal, which comprises:

selecting a composition comprising a pharmaceutically acceptable diluent, excipient or carrier, and a compound of the formula (I):

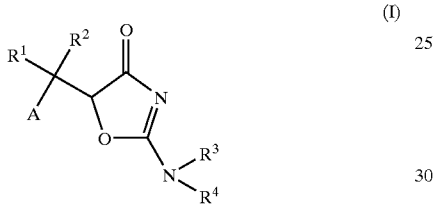

wherein:

A is an aromatic group which is unsubstituted or substituted by (1) a hydroxyl group, (2) a halogen atom, (3) a nitro group, (4) a cyano group, (5) a C1–4 alkyl group which is unsubstituted or substituted by 1 to 5 halogens, (6) a $C_{1-4}$ alkoxy group which is unsubstituted or substituted by 1 to 5 halogens, (7) a benzyloxy group, (8) a C1–4 alkoxy carbonyl group, (9) a methylene dioxo or (10) ethylene dioxo;

$R^1$ and $R^2$ are independently (1) a hydrogen atom, (2) a C1–7 alkyl group, (3) a $C_{2-6}$ alkenyl group, (4) a $C_{2-6}$ alkynyl group, (5) a $C_{3-9}$ cycloalkyl group, (6) a $C_{3-6}$ cycloalkenyl group, (7) a $C_{4-6}$ cycloalkadienyl group, or (8) an aryl group {wherein each of the above (2), (3), (4), (5), (6), (7) and (8) is unsubstituted or substituted by 1 to 5 substituents selected from the group consisting of: ① an aryl group which is unsubstituted or substituted by 1 to 2 substituents selected from the group consisting of an alkoxy group having 1 to 3 carbon atoms, a halogen atom, and an alkyl group having 1 to 3 carbon atoms, ② a $C_{3-7}$ cycloalkyl or $C_{3-6}$ cycloalkenyl group which is unsubstituted or substituted by an alkoxy group having 1 to 3 carbon atoms, a halogen atom or an alkyl group having 1 to 3 carbon atoms, ③ an aromatic heterocyclic group having at least 1 oxygen, sulfur or nitrogen ring-constituting hetero atom, which is unsubstituted or substituted by an alkyl group having 1 to 3 carbon atoms, ④ an amino group which is unsubstituted or substituted by an alkyl group having 1 to 3 carbon atoms, ⑤ a hydroxyl group which is unsubstituted or substituted by an alkyl group having 1 to 3 carbon atoms, ⑥ a thiol group which is unsubstituted or substituted by an alkyl group having 1 to 3 carbon atoms, and ⑦ a halogen;

and wherein each of the above (5), (6), (7) and (8) is unsubstituted or substituted by 1 to 5 $C_{1-3}$ alkyls}; and $R^3$ and $R^4$ are independently (1) a hydrogen atom, (2) a $C_{1-7}$ alkyl group, (3) a $C_{2-6}$ alkenyl group, (4) a $C_{2-6}$ alkynyl group, (5) a $C_{3-9}$ cycloalkyl group, (6) a $C_{3-6}$ cycloalkenyl group, (7) a $C_{3-6}$ cycloalkadienyl group, (8) an aryl group, (9) a $C_{1-8}$ alkanoyl group, (10) a $C_{3-6}$ alkenoyl group, (11) a $C_{4-7}$ cycloalkanecarbonyl group, (12) a $C_{1-4}$ alkanesulfonyl group, (13) a $C_{7-1}$ aroyl group, (14) a $C_{6-8}$ aryl-$C_{2-5}$ alkanoyl group, (15) a $C_{6-8}$ aryl-$C_{3-5}$ alkenoyl group, (16) a $C_{6-8}$ arenesulfonyl group, (17) an aromatic heterocyclic carbonyl group selected from the group consisting of furoyl, thienoyl, nicotinoyl, isonicotinoyl, pyrrolecarbonyl, oxazolecarbonyl, thiazolecarbonyl, imidazolecarbonyl and pyrazolecarbonyl, (18) an aromatic heterocyclic-$C_{2-5}$ alkanoyl group selected from the group consisting of thienylacetyl, thienylpropanoyl, furylacetyl, thiazolylacetyl, 1,2,4-thiadiazolylacetyl and pyridylacetyl, (19) an aliphatic heterocyclic carbonyl selected from the group consisting of azetidinylcarbonyl, pyrrolidinylcarbonyl and piperidinylcarbonyl, (20) carbamoyl, (21) N-monosubstitutional carbamoyl group {whose substituent is ① a $C_{1-6}$ alkyl group, ② a $C_{3-6}$ cycloalkyl group, ③ an aryl group, ④ an aralkyl group, or ⑤ an aromatic heterocyclic groups having at least 1 oxygen, sulfur or nitrogen ring-constituting hetero atom, wherein each of the above ③, ④ and ⑤ is unsubstituted or substituted by a hydroxyl group, an amino group (which is unsubstituted or substituted by 1 or 2 substituents selected from the group consisting of a $C_{1-4}$ alkyl, formyl, acetyl, propionyl and benzoyl), a halogen, a nitro, a cyano, a $C_{1-4}$ alkyl (which is unsubstituted or substituted by 1 to 5 halogens), or $C_{1-4}$ alkoxy (which is unsubstituted or substituted by 1 to 5 halogens)}, (22) N,N-disubstitutional carbamoyl group {in which one of the substituents is ① a $C_{1-6}$ alkyl, ② a $C_{3-6}$ cycloalkyl group, ③ an aryl group, ④ aralkyl group, or ⑤ an aromatic heterocyclic group having at least 1 oxygen, sulfur or nitrogen ring-constituting hetero atom, wherein each of the above ③, ④ and ⑤ is unsubstituted or substituted by a hydroxyl group, an amino group (which is unsubstituted or substituted by 1 or 2 substituents selected from the group consisting of a $C_{1-4}$ alkyl, formyl, acetyl, propionyl and benzoyl), a halogen, a nitro, a cyano, $C_{1-4}$ alkyl (which is unsubstituted or substituted by 1 to 5 halogens), or $C_{1-4}$ alkoxy (which is unsubstituted or substituted by 1 to 5 halogens), and the other substituent is a $C_{1-6}$ alkyl group, a $C_{3-6}$ cycloalkyl group, or a $C_{6-10}$ aralkyl group}, (23) a cyclic aminocarbamoyl selected from the group consisting of 1-azetidinylcarbonyl, 1-pyrrolidinylcarbonyl, piperidinocarbonyl, morpholinocarbonyl, 1-piperazinylcarbonyl, and 1-piperazinylcarbonyl having a $C_{1-6}$ alkyl group, benzyl, phenethyl, phenyl, 1-naphthyl or 2-naphthyl at the 4-position, (24) a carboxyl group, (25) a $C_{2-8}$ alkoxycarbonyl group, (26) a $C_{7-12}$ aryloxycarbonyl group, or (27) a $C_{8-10}$ aralkyloxycarbonyl group {wherein each of the above (2), (3), (4), (5), (6), (7) and (8) is unsubstituted or substituted by the group consisting of ① an aryl group which is unsubstituted or substituted by an alkoxy group having 1 to 3 carbon atoms, a halogen atom, or an alkyl group having 1 to 3 carbon atoms, ② a cycloalkyl or cycloalkenyl group which is unsubstituted or substituted by an alkoxy group having 1 to 3 carbon atoms, a halogen atom, or an alkyl group having 1 to 3 carbon atoms, ③ an aromatic heterocyclic group having at least 1 oxygen, sulfur or nitrogen ring-constituting hetero atom, which is unsubstituted or substituted by an alkyl group having 1 to 3 carbon atoms, ④ an amino group which is unsubstituted or substituted by, an alkyl group having 1 to 3 carbon atoms, ⑤ a hydroxyl group which is unsubstituted or substituted by an alkyl group having 1 to 3 carbon atoms, ⑥ a thiol group which is unsubstituted or substituted by an alkyl group having 1 to 3 carbon atoms, and ⑦ a halogen;
wherein each of the above (5), (6), (7) and (8) is unsubstituted or substituted by $C_{1-3}$ alkyl;

and wherein each of the above (26) and (27) is unsubstituted or substituted by the group consisting of ① a hydroxyl group, ② an amino group which may substituted by 1 or 2 substituents selected from the group consisting of a $C_{1-4}$ alkyl, formyl, acetyl, propionyl and benzolyl, ③ a halogen, ④ a nitro, ⑤ cyano, ⑥ a $C_{1-4}$ alkyl which is unsubstituted or substituted by 1 to 5 halogens, and ⑦ $C_{1-4}$ alkoxy which is unsubstituted or substituted by 1 to 5 halogens}, or a pharmacologically acceptable salt thereof, and administering said composition to a patient in need thereof, wherein said patient has an indication other than gastric or duodenal ulcer, gastritis or gastric cancer.

2. A method as in claim 1, wherein compound (I) is indolmycin.

* * * * *

UNITED STATES PATENT AND TRADEMARK OFFICE
CERTIFICATE OF CORRECTION

PATENT NO.      : 6,414,003 B1
DATED           : July 2, 2002
INVENTOR(S)     : Tsuneo Kanamaru et al.

It is certified that error appears in the above-identified patent and that said Letters Patent is hereby corrected as shown below:

Column 1,
Line 32, "the-respective" should read -- the respective --;
Line 62, "INFORMATION" should read -- INVENTION --.

Column 3,
Line 40, "a·hydrocarbon" should read -- a hydrocarbon --.

Column 5,
Line 22, "in-dolyl," should read -- indolyl, --.

Column 6,
Line 40, "5-hexenyll" should read -- 5-hexenyl, --.

Column 8,
Line 28, "arbonyl" should read -- carbonyl --;
Line 44, "Such" should read -- such --.

Column 9,
Line 9, "$R_4$'" should read -- $R^{4'}$ --;
Line 10, "(I')," should read -- (I"), --;
Line 25, "may" should read -- may be --;
Line 61, "phenethyll" should read -- phenethyl, --;
Line 67, "group." should read -- groups. --.

Column 11,
Line 13, "may" should read -- may be --.

Column 47,
Line 60, "methyithiomethyl," should read -- methylthiomethyl, --.

Column 50,
Line 10, "50 mol." should read -- 50 mol, --.

UNITED STATES PATENT AND TRADEMARK OFFICE
CERTIFICATE OF CORRECTION

PATENT NO. : 6,414,003 B1
DATED : July 2, 2002
INVENTOR(S) : Tsuneo Kanamaru et al.

It is certified that error appears in the above-identified patent and that said Letters Patent is hereby corrected as shown below:

Column 54,
Line 4, "phenylpropionyl" should read -- phenylpropionyl, --.

Column 55,
Line 10, "nitrites" should read -- nitriles --;
Line 43, "; and" should read -- and --.

Column 57,
Line 24, "EC-21" should read -- HC-21 --.

Column 60,
Line 60, "31+56" should read -- 31-56 --.

Column 61,
Line 31, "16.07;" should read -- 16.07. --.

Column 62,
Line 33, "(Indol" should read -- (indol --.

Column 63,
Line 16, "(Indol" should read -- (indol --.

Column 65,
Line 26, "Benzyloxybenzoyl)-" should read -- benzyloxybenzoyl)- --;
Line 46, "Hydroxybenzoyl)-" should read -- hydroxybenzoyl)- --;
Line 62, "(Indol" should read -- (indol --.

Column 66,
Line 15, "Benzyloxycarbonyl" should read -- benzyloxycarbonyl- --.

Column 67,
Line 7, "8.10(1H,bs)" should read -- 8.10(1H,bs). --;
Line 10, "Alanyl" should read -- alanyl --.

UNITED STATES PATENT AND TRADEMARK OFFICE
CERTIFICATE OF CORRECTION

PATENT NO. : 6,414,003 B1
DATED : July 2, 2002
INVENTOR(S) : Tsuneo Kanamaru et al.

It is certified that error appears in the above-identified patent and that said Letters Patent is hereby corrected as shown below:

Column 68,
Line 2, "(Indol" should read -- (indol --;
Line 27, "Fluoroindol" should read -- fluoroindol --.

Column 69,
Line 1, "4.97(0.4H,d,J=1.5 Hz)I" should read -- 4.97(0.4H,d,J=1.5 Hz), --;
Line 47, "-5-((1R)-" should read -- -5-[(1R)- --.

Column 70,
Line 2, "3.78(!H,m)," should read -- 3.78(1H,m), --;
Line 22, "((1R)" should read -- [(1R) --; and "ethyll" should read -- ethyl] --;
Line 55, "((1R)" should read -- [(1R) --.

Column 71,
Line 50, "Benzylphthaloyl" should read -- benzylphthaloyl --.

Column 72,
Line 9, "(Indol" should read -- (indol --;
Line 27, "Methylamino" should read -- methylamino --.

Column 73,
Line 57, "Methylamino" should read -- methylamino --.

Column 75,
Line 28, "Hydroxyindol" should read -- hydroxyindol --;
Line 53, "Methoxyindol" should read -- methoxyindol--.

Column 76,
Line 29, "The-methylamine" should read -- The methylamine --;
Line 40, "Chloroindol" should read -- chloroindol --.

Column 77,
Line 9, "(Indol" should read -- (indol --;
Line 31, "Diacetylamino" should read -- diacetylamino --;
Line 52, "Acetylamino" should read -- acetylamino --.

UNITED STATES PATENT AND TRADEMARK OFFICE
CERTIFICATE OF CORRECTION

PATENT NO.    : 6,414,003 B1
DATED         : July 2, 2002
INVENTOR(S)   : Tsuneo Kanamaru et al.

It is certified that error appears in the above-identified patent and that said Letters Patent is hereby corrected as shown below:

Column 79,
Line 61, "pyloriinfec-" should read -- pylori infec- --.

Column 81,
Lines 36 and 40, "C1-4" should read -- $C_{1-4}$ --;
Line 43, "C1-7" should read -- $C_{1-7}$ --.

Column 82,
Line 11, "$C_{7-1}$" should read -- $C_{7-11}$ --;
Line 29, "groups" should read -- group --;
Line 67, "of ①" should read -- of: ① --.

Column 83,
Line 12, "by," should read -- by --.

Column 84,
Line 2, "of ①" should read --of: ① --;
Line 3, "may" should read -- may be --;
Line 10, "thereof, and" should read -- thereof; and --.

Signed and Sealed this

Eighteenth Day of March, 2003

JAMES E. ROGAN
*Director of the United States Patent and Trademark Office*